(12) United States Patent
Loomas et al.

(10) Patent No.: US 9,833,354 B2
(45) Date of Patent: Dec. 5, 2017

(54) NASAL RESPIRATORY DEVICES

(71) Applicant: Theravent, Inc., San Jose, CA (US)

(72) Inventors: Bryan Loomas, Los Gatos, CA (US); Rajiv Doshi, Los Altos, CA (US); Ryan Kendall Pierce, San Francisco, CA (US); Robert A. Howard, Palo Alto, CA (US); Motohide Hatanaka, Tokyo (JP)

(73) Assignee: Theravent, Inc., San Jose, CA (US)

( * ) Notice: Subject to any disclaimer, the term of this patent is extended or adjusted under 35 U.S.C. 154(b) by 0 days.

(21) Appl. No.: 14/997,870

(22) Filed: Jan. 18, 2016

(65) Prior Publication Data

US 2016/0128863 A1 May 12, 2016

Related U.S. Application Data

(63) Continuation-in-part of application No. 12/877,836, filed on Sep. 8, 2010, now Pat. No. 9,238,113, which
(Continued)

(51) Int. Cl.
*A61F 5/56* (2006.01)
*A61M 15/08* (2006.01)
(Continued)

(52) U.S. Cl.
CPC ............. *A61F 5/56* (2013.01); *A61M 15/002* (2014.02); *A61M 15/08* (2013.01);
(Continued)

(58) Field of Classification Search
CPC .. A61M 16/0683; A61M 16/06; A61M 25/02; A61M 2210/0618; A61M 16/0666;
(Continued)

(56) References Cited

U.S. PATENT DOCUMENTS

| 69,396 A | 10/1867 | Curtis |
| 628,111 A | 7/1899 | McHatton |
| | (Continued) | |

FOREIGN PATENT DOCUMENTS

| EP | 0434258 A2 | 6/1991 |
| EP | 1157663 A1 | 11/2001 |
| | (Continued) | |

OTHER PUBLICATIONS

Witt et al.; U.S. Appl. No. 61/141,251 entitled "System, Method, and Respiration Appliance for Supporting the Airway of a Subject," filed Dec. 30, 2008.

(Continued)

*Primary Examiner* — Ophelia A Hawthorne
(74) *Attorney, Agent, or Firm* — Shay Glenn LLP

(57) ABSTRACT

Devices for altering the flow of air in a respiratory cavity such as the nostrils of the nose. These methods and devices may be useful for affecting a physiologic benefit in patients suffering from a variety of medical disorders, including snoring and sleep apnea. The devices are typically removable devices that may be placed in both nostrils to increase resistance to airflow within the respiratory cavity. Resistance to expiration may be selectively increased relative to inspiration. The nasal devices may also increases patency of the nares. Any of these devices may be configured to achieve positive end-expiratory pressure (PEEP) in a subject wearing the device.

20 Claims, 38 Drawing Sheets

Related U.S. Application Data is a continuation of application No. 11/811,401, filed on Jun. 7, 2007, now Pat. No. 7,806,120, which is a continuation-in-part of application No. 11/298,640, filed on Dec. 8, 2005, now Pat. No. 7,735,492, application No. 14/997,870, which is a continuation-in-part of application No. 14/371,392, filed as application No. PCT/US2013/022121 on Jan. 18, 2013.

(60) Provisional application No. 60/634,715, filed on Dec. 8, 2004, provisional application No. 60/811,814, filed on Jun. 7, 2006, provisional application No. 61/589,071, filed on Jan. 20, 2012.

(51) Int. Cl.
*A61M 15/00* (2006.01)
*A61M 16/00* (2006.01)
*A62B 23/06* (2006.01)

(52) U.S. Cl.
CPC ........... *A61M 2016/003* (2013.01); *A61M 2016/0027* (2013.01); *A61M 2210/0618* (2013.01); *A62B 23/06* (2013.01)

(58) Field of Classification Search
CPC .. A61M 2016/0039; A61M 2016/0036; A61M 2016/0069; A61M 2016/0021; A61M 16/00; A62B 9/02; A62B 9/022; B64D 2013/0681; B63C 11/24
See application file for complete search history.

(56) References Cited

U.S. PATENT DOCUMENTS

| | | |
|---|---|---|
| 669,098 A | 3/1901 | Overshiner |
| 675,275 A | 5/1901 | Gunning |
| 718,785 A | 1/1903 | McNary |
| 746,869 A | 12/1903 | Moulton |
| 774,446 A | 11/1904 | Moulton |
| 810,617 A | 1/1906 | Carence |
| 1,819,884 A | 8/1931 | Fores |
| 2,198,959 A | 4/1940 | Clarke |
| 2,237,954 A | 4/1941 | Wilson |
| 2,264,153 A | 11/1941 | Rowe |
| 2,274,886 A | 3/1942 | Carroll |
| 2,282,681 A | 5/1942 | Stotz |
| 2,335,936 A | 12/1943 | Hanlon |
| 2,433,565 A | 12/1947 | Korman |
| 2,448,724 A | 9/1948 | McGovney |
| 2,593,315 A | 4/1952 | Kraft |
| 2,672,138 A | 3/1954 | Carlock |
| 2,751,906 A | 6/1956 | Irvine |
| 2,777,442 A | 1/1957 | Zelano |
| 3,145,711 A | 8/1964 | Beber |
| 3,315,701 A | 4/1967 | Stilwell |
| 3,370,305 A | 2/1968 | Goott et al. |
| 3,451,392 A | 6/1969 | Cook et al. |
| 3,463,149 A | 8/1969 | Albu |
| 3,513,839 A | 5/1970 | Vacante |
| 3,556,122 A | 1/1971 | Laerdal |
| 3,616,802 A | 11/1971 | Marinaccio |
| 3,657,855 A | 4/1972 | Swezey |
| 3,695,265 A | 10/1972 | Brevik |
| 3,710,799 A | 1/1973 | Caballero |
| 3,722,509 A | 3/1973 | Nebel |
| 3,747,597 A | 7/1973 | Olivera |
| 3,802,426 A | 4/1974 | Sakamoto |
| 3,884,223 A | 5/1975 | Keindl |
| 3,902,621 A | 9/1975 | Hidding |
| 4,004,584 A | 1/1977 | Geaney |
| 4,030,491 A | 6/1977 | Mattila |
| 4,040,428 A | 8/1977 | Clifford |
| 4,054,134 A | 10/1977 | Kritzer |
| 4,062,358 A | 12/1977 | Kritzer |
| 4,094,316 A | 6/1978 | Nathanson |
| 4,143,872 A | 3/1979 | Havstad et al. |
| 4,212,296 A | 7/1980 | Schaar |
| 4,220,150 A | 9/1980 | King |
| 4,221,217 A | 9/1980 | Amezcua |
| 4,226,233 A | 10/1980 | Kritzer |
| 4,240,420 A | 12/1980 | Riaboy |
| 4,267,831 A | 5/1981 | Aguilar |
| 4,325,366 A | 4/1982 | Tabor |
| 4,327,719 A | 5/1982 | Childers |
| RE31,040 E | 9/1982 | Possis |
| 4,354,489 A | 10/1982 | Riaboy |
| 4,403,616 A | 9/1983 | King |
| 4,456,016 A | 6/1984 | Nowacki et al. |
| 4,487,207 A | 12/1984 | Fitz |
| 4,533,137 A | 8/1985 | Sonne |
| 4,582,058 A | 4/1986 | Depel et al. |
| 4,584,997 A | 4/1986 | Delong |
| 4,601,465 A | 7/1986 | Roy |
| 4,640,277 A | 2/1987 | Meyer et al. |
| 4,651,873 A | 3/1987 | Stolcenberg et al. |
| 4,702,374 A | 10/1987 | Kelner |
| 4,718,554 A | 1/1988 | Barbato |
| 4,739,987 A | 4/1988 | Nicholson |
| 4,759,356 A | 7/1988 | Muir |
| 4,822,354 A | 4/1989 | Elosegui |
| 4,854,574 A | 8/1989 | Larson et al. |
| 4,860,766 A | 8/1989 | Sackner |
| 4,862,903 A | 9/1989 | Campbell |
| 4,908,028 A | 3/1990 | Colon et al. |
| 4,913,138 A | 4/1990 | Yoshida et al. |
| 4,919,138 A | 4/1990 | Nordenstroom |
| 4,973,047 A | 11/1990 | Norell |
| 4,979,505 A | 12/1990 | Cox |
| 4,984,302 A | 1/1991 | Lincoln |
| 4,984,581 A | 1/1991 | Stice |
| 5,016,425 A | 5/1991 | Weick |
| 5,033,312 A | 7/1991 | Stupecky |
| 5,038,621 A | 8/1991 | Stupecky |
| 5,052,400 A | 10/1991 | Dietz |
| 5,059,208 A | 10/1991 | Coe et al. |
| 5,074,293 A | 12/1991 | Lott et al. |
| 5,078,739 A | 1/1992 | Martin |
| 5,092,781 A | 3/1992 | Casciotti et al. |
| 5,117,820 A | 6/1992 | Robitaille |
| 5,197,980 A | 3/1993 | Gorshkov et al. |
| 5,255,687 A | 10/1993 | McKenna |
| 5,383,470 A | 1/1995 | Kolbly |
| 5,385,542 A | 1/1995 | Rawlings |
| 5,391,205 A | 2/1995 | Knight |
| 5,392,773 A | 2/1995 | Bertrand |
| 5,394,867 A | 3/1995 | Swann |
| 5,414,627 A | 5/1995 | Wada et al. |
| 5,415,660 A | 5/1995 | Campbell et al. |
| 5,425,359 A | 6/1995 | Liou |
| 5,459,544 A | 10/1995 | Emura |
| 5,522,382 A | 6/1996 | Sullivan et al. |
| 5,535,739 A | 7/1996 | Rapoport et al. |
| 5,562,641 A | 10/1996 | Flomenblit et al. |
| 5,568,808 A | 10/1996 | Rimkus |
| 5,572,994 A | 11/1996 | Smith |
| 5,607,469 A | 3/1997 | Frey |
| 5,649,533 A | 7/1997 | Oren |
| 5,665,104 A | 9/1997 | Lee |
| 5,727,546 A | 3/1998 | Clarke et al. |
| 5,730,122 A | 3/1998 | Lurie |
| 5,740,798 A | 4/1998 | McKinney |
| 5,743,256 A | 4/1998 | Jalowayski |
| 5,763,979 A | 6/1998 | Mukherjee et al. |
| 5,775,335 A | 7/1998 | Seal |
| 5,782,896 A | 7/1998 | Chen et al. |
| 5,797,920 A | 8/1998 | Kim |
| 5,803,121 A | 9/1998 | Estes |
| 5,823,187 A | 10/1998 | Estes et al. |
| 5,848,590 A | 12/1998 | Smith |
| 5,865,170 A | 2/1999 | Moles |
| 5,876,434 A | 3/1999 | Flomenblit et al. |
| 5,878,743 A | 3/1999 | Zdrojkowski et al. |
| 5,890,998 A | 4/1999 | Hougen |

(56) References Cited

U.S. PATENT DOCUMENTS

| | | | |
|---|---|---|---|
| 5,899,832 A | 5/1999 | Hougen | |
| 5,910,071 A | 6/1999 | Hougen | |
| 5,911,756 A | 6/1999 | Debry | |
| 5,947,119 A | 9/1999 | Reznick | |
| 5,954,766 A | 9/1999 | Zadno-Azizi et al. | |
| 5,957,978 A | 9/1999 | Blom | |
| 5,992,006 A | 11/1999 | Datsikas | |
| 6,004,342 A | 12/1999 | Filis | |
| 6,058,932 A | 5/2000 | Hughes | |
| 6,083,141 A | 7/2000 | Hougen | |
| D430,667 S | 9/2000 | Rome | |
| 6,119,690 A | 9/2000 | Pantaleo | |
| 6,165,133 A | 12/2000 | Rapoport et al. | |
| 6,177,482 B1 | 1/2001 | Cinelli et al. | |
| 6,189,532 B1 | 2/2001 | Hely et al. | |
| 6,213,955 B1 | 4/2001 | Karakasoglu et al. | |
| 6,219,997 B1 | 4/2001 | Friberg et al. | |
| 6,258,100 B1 | 7/2001 | Alferness et al. | |
| 6,287,290 B1 | 9/2001 | Perkins et al. | |
| 6,293,951 B1 | 9/2001 | Alferness et al. | |
| 6,311,839 B1 | 11/2001 | Lo | |
| 6,328,038 B1 | 12/2001 | Kessler et al. | |
| 6,369,126 B1 | 4/2002 | Cinelli et al. | |
| 6,398,775 B1 | 6/2002 | Perkins et al. | |
| 6,439,233 B1 | 8/2002 | Geertsema | |
| 6,484,725 B1 | 11/2002 | Chi | |
| 6,500,095 B1 | 12/2002 | Hougen | |
| 6,510,846 B1 | 1/2003 | O'Rourke | |
| 6,527,761 B1 | 3/2003 | Soltesz et al. | |
| 6,561,188 B1 | 5/2003 | Ellis | |
| 6,562,057 B2 | 5/2003 | Santin | |
| 6,568,387 B2 | 5/2003 | Davenport et al. | |
| 6,573,421 B1 | 6/2003 | Lemaire | |
| 6,581,598 B1 | 6/2003 | Foran et al. | |
| 6,585,639 B1 | 7/2003 | Kotmel et al. | |
| 6,592,594 B2 | 7/2003 | Rimbaugh et al. | |
| 6,592,995 B2 | 7/2003 | Topolkaraev et al. | |
| 6,595,215 B2 | 7/2003 | Wood | |
| 6,609,516 B2 | 8/2003 | Hollander et al. | |
| 6,626,172 B1 | 9/2003 | Karow et al. | |
| 6,626,179 B1 | 9/2003 | Pedley | |
| 6,631,721 B1 | 10/2003 | Salter et al. | |
| 6,679,264 B1 | 1/2004 | Deem et al. | |
| 6,694,979 B2 | 2/2004 | Deem et al. | |
| 6,722,360 B2 | 4/2004 | Doshi | |
| 6,726,598 B1 | 4/2004 | Jarvis et al. | |
| 6,737,160 B1 | 5/2004 | Full et al. | |
| 6,769,432 B1 | 8/2004 | Keifer | |
| 6,776,162 B2 | 8/2004 | Wood | |
| 6,776,163 B2 | 8/2004 | Dougill et al. | |
| 6,811,538 B2 | 11/2004 | Westbrook et al. | |
| 6,841,716 B1 | 1/2005 | Tsutsumi | |
| 6,848,446 B2 | 2/2005 | Noble | |
| 6,863,066 B2 | 3/2005 | Ogle | |
| 6,866,652 B2 | 3/2005 | Bierman | |
| 6,872,439 B2 | 3/2005 | Fearing et al. | |
| 6,913,017 B2 | 7/2005 | Roberts | |
| 6,921,574 B2 | 7/2005 | Cinelli et al. | |
| 6,997,177 B2 | 2/2006 | Wood | |
| 7,011,723 B2 | 3/2006 | Full et al. | |
| 7,013,896 B2 | 3/2006 | Schmidt | |
| 7,047,969 B2 | 5/2006 | Noble | |
| 7,156,098 B2 | 1/2007 | Dolezal et al. | |
| 7,175,723 B2 | 2/2007 | Jones et al. | |
| 7,178,524 B2 | 2/2007 | Noble | |
| 7,201,169 B2 | 4/2007 | Wilkie et al. | |
| D542,407 S | 5/2007 | Stallard et al. | |
| 7,263,996 B2 | 9/2007 | Yung Ho | |
| 7,334,581 B2 | 2/2008 | Doshi | |
| D566,834 S | 4/2008 | Barton | |
| 7,422,014 B1 | 9/2008 | Smith | |
| 7,506,649 B2 | 3/2009 | Doshi et al. | |
| 7,559,326 B2 | 7/2009 | Smith et al. | |
| 7,578,294 B2 | 8/2009 | Pierro et al. | |
| 7,640,934 B2 | 1/2010 | Zollinger et al. | |
| 7,735,491 B2 | 6/2010 | Doshi et al. | |
| 7,735,492 B2 | 6/2010 | Doshi et al. | |
| 7,762,252 B2 | 7/2010 | Prete | |
| 7,798,148 B2 | 9/2010 | Doshi et al. | |
| 7,806,120 B2 | 10/2010 | Loomas et al. | |
| 7,856,979 B2 | 12/2010 | Doshi et al. | |
| 7,880,051 B2 | 2/2011 | Madsen et al. | |
| 7,987,852 B2* | 8/2011 | Doshi | A62B 23/06 128/204.11 |
| 7,992,563 B2 | 8/2011 | Doshi | |
| 7,992,564 B2 | 8/2011 | Doshi et al. | |
| 7,992,566 B2 | 8/2011 | Pflueger et al. | |
| 8,020,700 B2 | 9/2011 | Doshi et al. | |
| 8,061,357 B2 | 11/2011 | Pierce et al. | |
| 8,215,308 B2 | 7/2012 | Doshi et al. | |
| 8,235,046 B2 | 8/2012 | Doshi et al. | |
| 8,240,309 B2* | 8/2012 | Doshi | A61F 5/08 128/200.24 |
| 8,251,066 B1 | 8/2012 | Ho et al. | |
| 8,281,557 B2 | 10/2012 | Doshi et al. | |
| 8,291,909 B2 | 10/2012 | Doshi et al. | |
| 8,302,606 B2 | 11/2012 | Doshi et al. | |
| 8,302,607 B2 | 11/2012 | Pierce et al. | |
| 8,365,736 B2 | 2/2013 | Doshi et al. | |
| 8,707,955 B2 | 4/2014 | Doshi | |
| 8,875,711 B2 | 11/2014 | Sather et al. | |
| 8,985,116 B2 | 3/2015 | Doshi et al. | |
| 9,238,113 B2 | 1/2016 | Loomas et al. | |
| 2001/0051799 A1 | 12/2001 | Ingenito | |
| 2001/0056274 A1 | 12/2001 | Perkins et al. | |
| 2002/0062120 A1 | 5/2002 | Perkins et al. | |
| 2002/0077593 A1 | 6/2002 | Perkins et al. | |
| 2002/0112729 A1 | 8/2002 | DeVore et al. | |
| 2002/0157673 A1 | 10/2002 | Kessler et al. | |
| 2003/0024527 A1 | 2/2003 | Ginn | |
| 2003/0050648 A1 | 3/2003 | Alferness et al. | |
| 2003/0070682 A1 | 4/2003 | Wilson et al. | |
| 2003/0106555 A1 | 6/2003 | Tovey | |
| 2003/0106556 A1 | 6/2003 | Alperovich et al. | |
| 2003/0140925 A1 | 7/2003 | Sapienza et al. | |
| 2003/0149387 A1 | 8/2003 | Barakat et al. | |
| 2003/0154988 A1 | 8/2003 | DeVore et al. | |
| 2003/0158515 A1 | 8/2003 | Gonzalez et al. | |
| 2003/0195552 A1 | 10/2003 | Santin | |
| 2003/0209247 A1 | 11/2003 | O'Rourke | |
| 2004/0016432 A1 | 1/2004 | Genger et al. | |
| 2004/0020489 A1 | 2/2004 | Gillespie et al. | |
| 2004/0020492 A1 | 2/2004 | Dubrul et al. | |
| 2004/0020493 A1 | 2/2004 | Wood | |
| 2004/0055606 A1 | 3/2004 | Hendricksen et al. | |
| 2004/0112379 A1 | 6/2004 | Djupesland | |
| 2004/0123868 A1 | 7/2004 | Rutter | |
| 2004/0149615 A1 | 8/2004 | Eisenbraun | |
| 2004/0230108 A1 | 11/2004 | Melker et al. | |
| 2004/0254491 A1 | 12/2004 | Ricciardelli | |
| 2004/0261791 A1 | 12/2004 | Horian | |
| 2004/0261798 A1 | 12/2004 | Rimkus | |
| 2005/0010125 A1 | 1/2005 | Joy et al. | |
| 2005/0011524 A1 | 1/2005 | Thomlinson et al. | |
| 2005/0033344 A1 | 2/2005 | Dillard et al. | |
| 2005/0051170 A1 | 3/2005 | Koo | |
| 2005/0066965 A1 | 3/2005 | Cronk et al. | |
| 2005/0133039 A1 | 6/2005 | Wood | |
| 2005/0211250 A1 | 9/2005 | Dolezal et al. | |
| 2005/0279351 A1* | 12/2005 | Lewis | A61D 7/04 128/200.23 |
| 2005/0284479 A1 | 12/2005 | Schrader et al. | |
| 2006/0000472 A1 | 1/2006 | Fenton | |
| 2006/0016450 A1 | 1/2006 | Pearson et al. | |
| 2006/0085027 A1 | 4/2006 | Santin et al. | |
| 2006/0169285 A1 | 8/2006 | Bovo | |
| 2006/0180149 A1 | 8/2006 | Matarasso | |
| 2006/0266361 A1 | 11/2006 | Hernandez | |
| 2006/0283461 A1 | 12/2006 | Lubke et al. | |
| 2007/0016123 A1 | 1/2007 | Jensen | |
| 2007/0051364 A1 | 3/2007 | Jacobson et al. | |
| 2007/0095349 A1 | 5/2007 | Hansmann et al. | |
| 2007/0175478 A1 | 8/2007 | Brunst | |
| 2007/0227542 A1 | 10/2007 | Kashmakov et al. | |

(56) References Cited

U.S. PATENT DOCUMENTS

| | | |
|---|---|---|
| 2007/0287976 A1 | 12/2007 | Sherrill |
| 2008/0023007 A1 | 1/2008 | Dolezal et al. |
| 2008/0032119 A1 | 2/2008 | Feldhahn et al. |
| 2008/0041397 A1 | 2/2008 | Hirs |
| 2008/0053460 A1 | 3/2008 | Wilson |
| 2008/0087286 A1 | 4/2008 | Jones |
| 2008/0099021 A1 | 5/2008 | Moore |
| 2008/0135044 A1 | 6/2008 | Freitag et al. |
| 2008/0142014 A1 | 6/2008 | Jiang |
| 2008/0142018 A1 | 6/2008 | Doshi et al. |
| 2008/0221470 A1 | 9/2008 | Sather et al. |
| 2009/0145441 A1 | 6/2009 | Doshi et al. |
| 2009/0194100 A1 | 8/2009 | Minagi |
| 2009/0194109 A1 | 8/2009 | Doshi et al. |
| 2009/0308398 A1 | 12/2009 | Ferdinand et al. |
| 2011/0005520 A1 | 1/2011 | Doshi et al. |
| 2011/0067709 A1 | 3/2011 | Doshi et al. |
| 2011/0108041 A1 | 5/2011 | Sather et al. |
| 2011/0203598 A1 | 8/2011 | Favet et al. |
| 2011/0218451 A1 | 9/2011 | Lai et al. |
| 2011/0240038 A1 | 10/2011 | Doshi et al. |
| 2012/0285470 A9 | 11/2012 | Sather et al. |
| 2014/0109907 A1 | 4/2014 | Doshi et al. |
| 2014/0345623 A1 | 11/2014 | Pierce et al. |

FOREIGN PATENT DOCUMENTS

| | | |
|---|---|---|
| EP | 1205203 A2 | 5/2002 |
| EP | 1481702 A2 | 12/2004 |
| FR | 2862614 A1 | 5/2005 |
| GB | 2096574 A | 10/1982 |
| GB | 2324729 A | 4/1998 |
| JP | 52-123786 A | 10/1977 |
| JP | 55-122742 U | 9/1980 |
| JP | 58-136345 A | 8/1983 |
| JP | 63-189257 U | 12/1988 |
| JP | 7-47126 | 2/1995 |
| JP | 3059270 U | 3/1999 |
| JP | 2001-299916 A | 10/2001 |
| JP | 2002-153489 A | 5/2002 |
| JP | 2002-219174 A | 8/2002 |
| JP | 2002-345963 A | 12/2002 |
| JP | 2002-345966 | 12/2002 |
| JP | 2005-40589 A | 2/2005 |
| JP | 2005-505355 | 2/2005 |
| JP | 2008-136496 | 6/2008 |
| JP | 2008-522763 | 7/2008 |
| RU | 2048820 C1 | 11/1995 |
| SU | 1586709 A1 | 8/1990 |
| WO | WO 90/12614 A1 | 11/1990 |
| WO | WO 93/08777 A1 | 5/1993 |
| WO | WO 95/17220 A1 | 6/1995 |
| WO | WO 95/33520 A1 | 12/1995 |
| WO | WO 98/46310 A2 | 10/1998 |
| WO | WO 99/03395 A1 | 1/1999 |
| WO | WO 00/29066 A1 | 5/2000 |
| WO | WO 00/50121 A1 | 8/2000 |
| WO | WO 00/67848 A1 | 11/2000 |
| WO | WO 01/02042 A1 | 1/2001 |
| WO | WO 01/13839 A1 | 3/2001 |
| WO | WO 01/13908 A2 | 3/2001 |
| WO | WO 01/49371 A2 | 7/2001 |
| WO | WO 01/62342 A1 | 8/2001 |
| WO | WO 01/87170 A1 | 11/2001 |
| WO | WO 01/89381 A1 | 11/2001 |
| WO | WO 02/38038 A2 | 5/2002 |
| WO | WO 03/022124 A2 | 3/2003 |
| WO | WO 03/034927 A1 | 5/2003 |
| WO | WO 2004/084998 A1 | 10/2004 |
| WO | WO2005/000805 A2 | 1/2005 |
| WO | WO2006/040585 A2 | 4/2006 |
| WO | WO2007/023607 | 3/2007 |
| WO | WO 2007/129814 A1 | 11/2007 |
| WO | WO 2007/134458 A1 | 11/2007 |
| WO | WO 2007/146133 A2 | 12/2007 |

OTHER PUBLICATIONS http://chinookmed.com/index.cfm/fa/product.display&Product_ID=275; accessed Nov. 28, 2007.

Mahadevia, A. K. et al., Effects of expiratory positive airway pressure on sleep-induced respiratory abnormalities in patients with hypersomnia-sleep apnea syndrome, Am Rev Respir Dis 1983, vol. 128, pp. 708-711, Oct. 1983.

Dillard, D. et al., Evaluation of a novel intra-bronchial valve to produce lung volume reduction, World Congress of Bronchology, Jun. 2002 (figs. 1-4 available upon request).

Hakel et al.; Nasal obturator for velopharyngeal dysfunction in dysarthria: technical report on a one-way valve; Journal of Medical Speech-Language Pathology; vol. 12; No. 4; pp. 155-159; Dec. 2004.

Suwaki et al.; Nasal speaking valve: a device for managing velopharyngeal incompetence; Journal of Oral Rehabilitation; vol. 35(1); pp. 73-78; Jan. 2008.

Suwaki et al.; The effect of nasal speaking valve on the speech under experimental velopharyngeal incompetence condition; Journal of Oral Rehabilitation; vol. 35(5); pp. 361-369; May 2008.

Doshi et al., U.S. Appl. No. 13/545,865 entitled "Nasal Devices," filed Jul. 10, 2012.

Cline et al. U.S. Appl. No. 14/071,582 entitled "Passive Nasal Peep Devices," filed Nov. 4, 2013.

\* cited by examiner

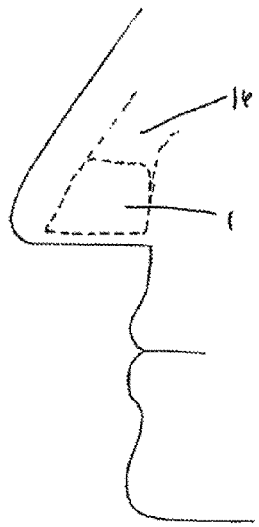
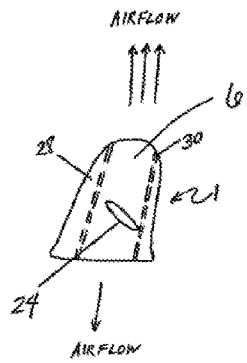
FIG. 6
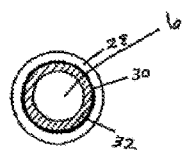
FIG. 5
FIG. 7A FIG. 7B
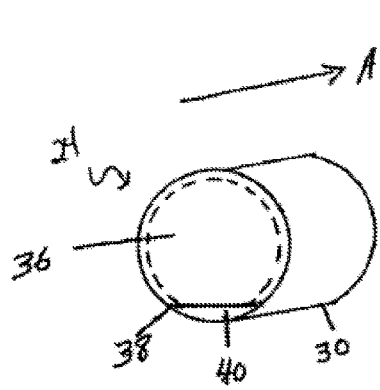
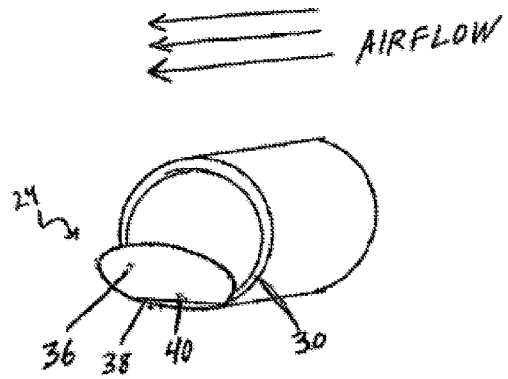
FIG. 8A FIG. 8B

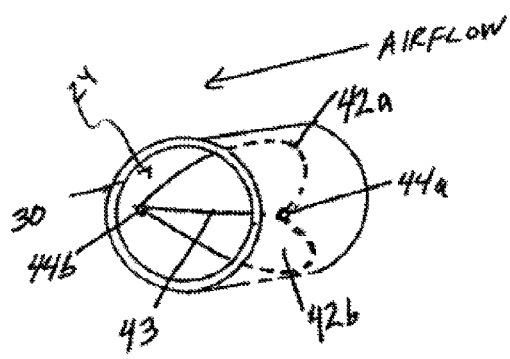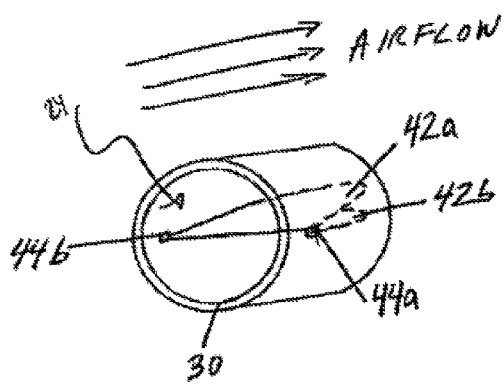
FIG. 9A　　　　　　　　　　FIG. 9B
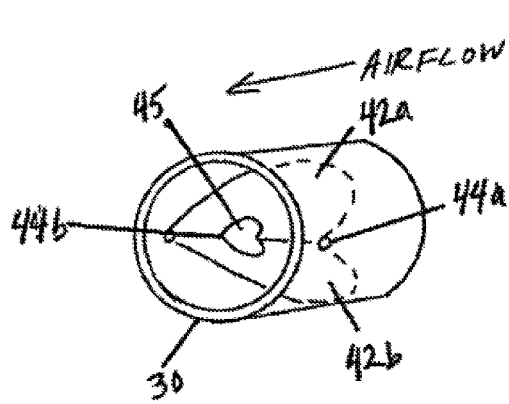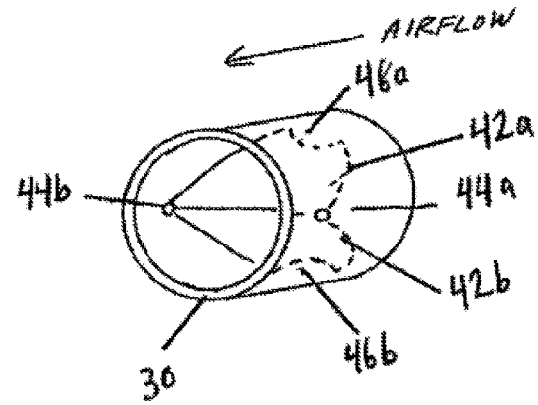
FIG. 10　　　　　　　　　　FIG. 11

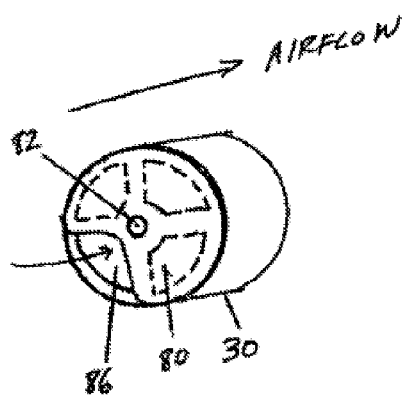
FIG. 17A
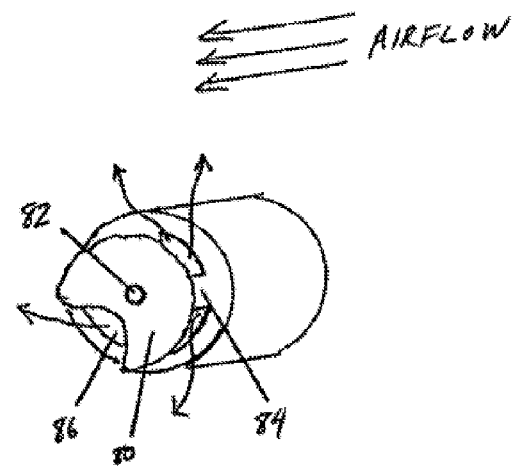
FIG. 17B
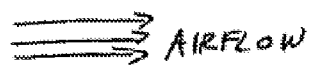
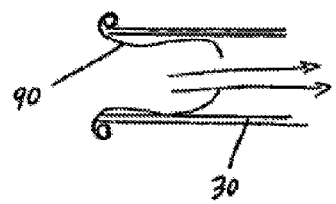
FIG. 18A
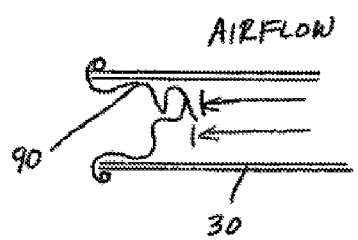
FIG. 18B

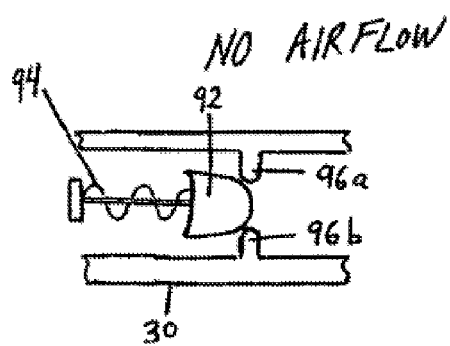
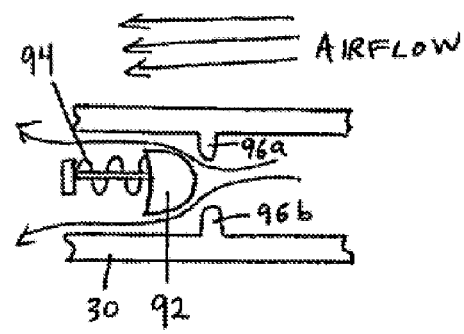
FIG. 19A                FIG. 19B
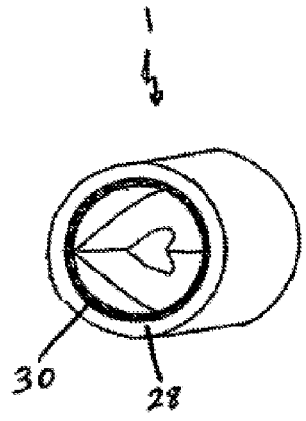
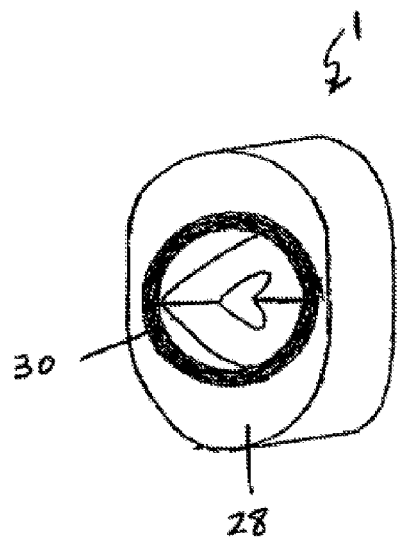
FIG. 20                 FIG. 21

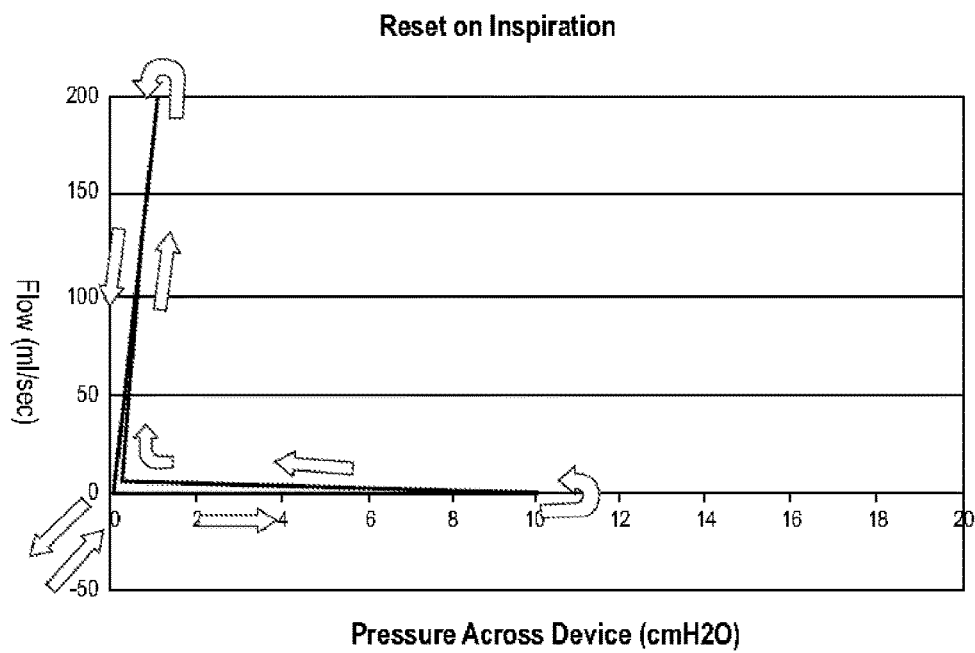
FIG. 36
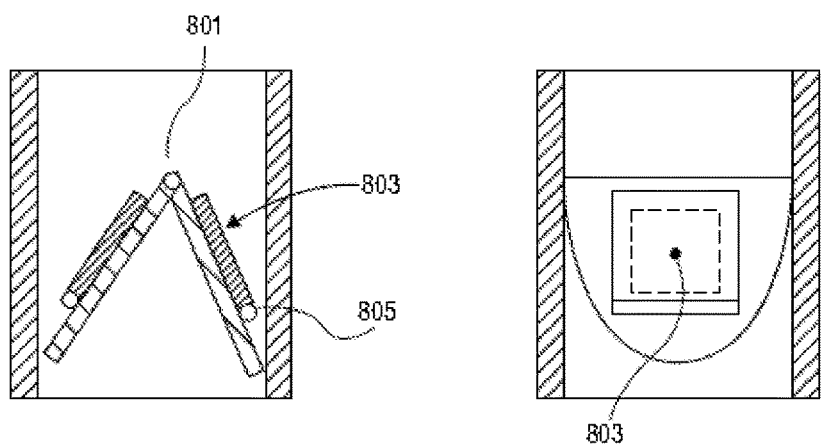
FIG. 37A
FIG. 37B

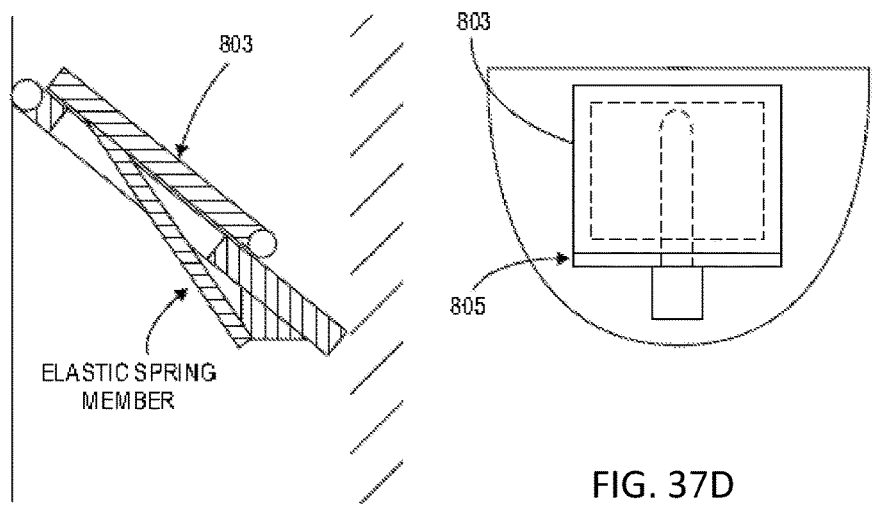
FIG. 37C
FIG. 37D
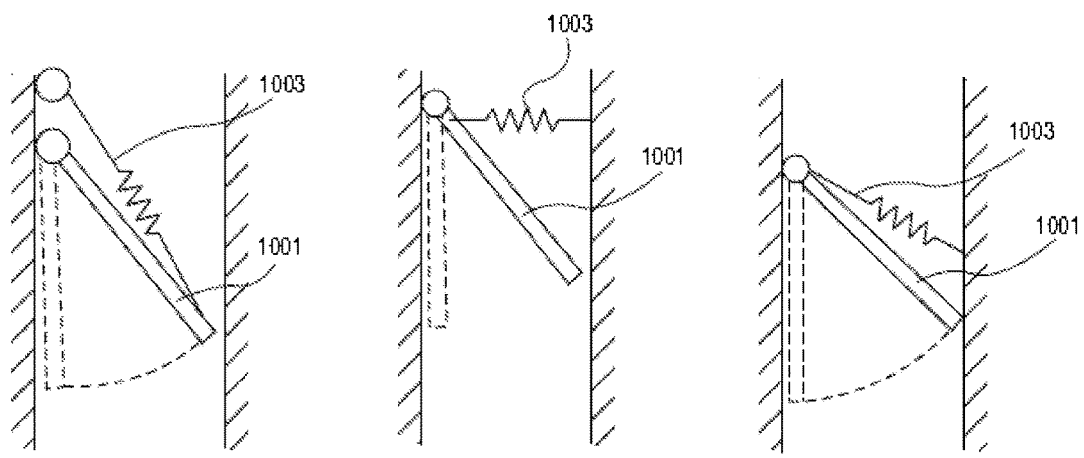
FIG. 39A
FIG. 39B
FIG. 39C

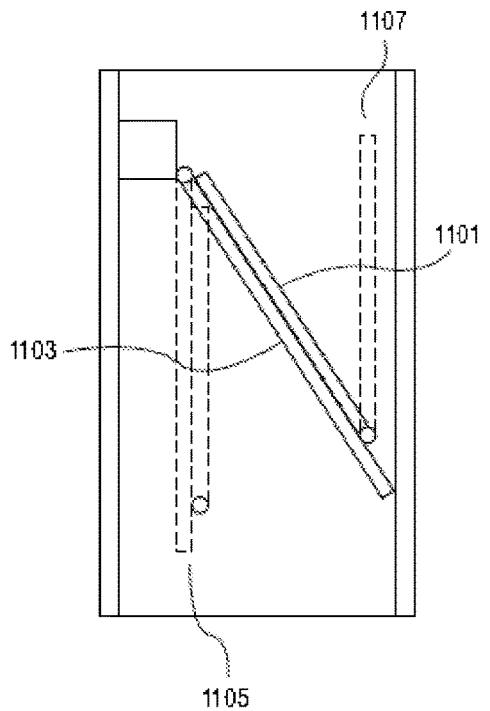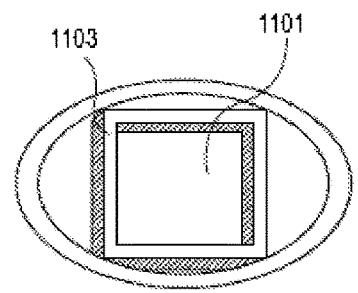
FIG. 40A
FIG. 40B
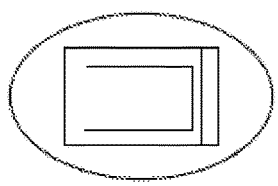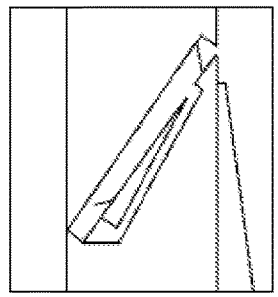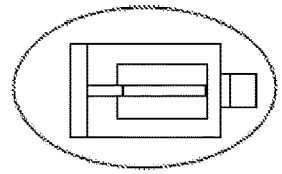
FIG. 41A
FIG. 41B
FIG. 41C
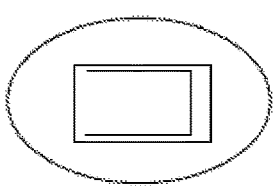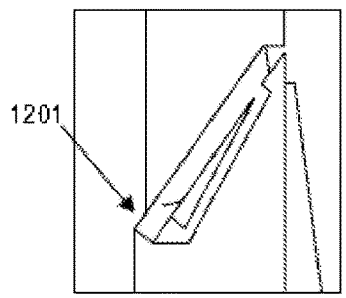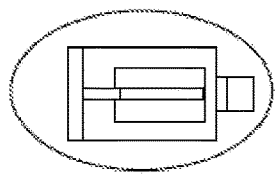
FIG. 41D
FIG. 41E
FIG. 41F

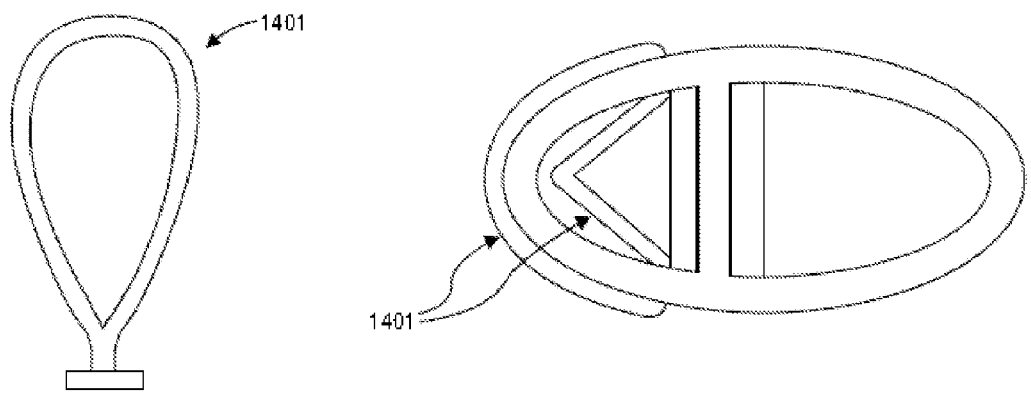
FIG. 43B
FIG. 43C
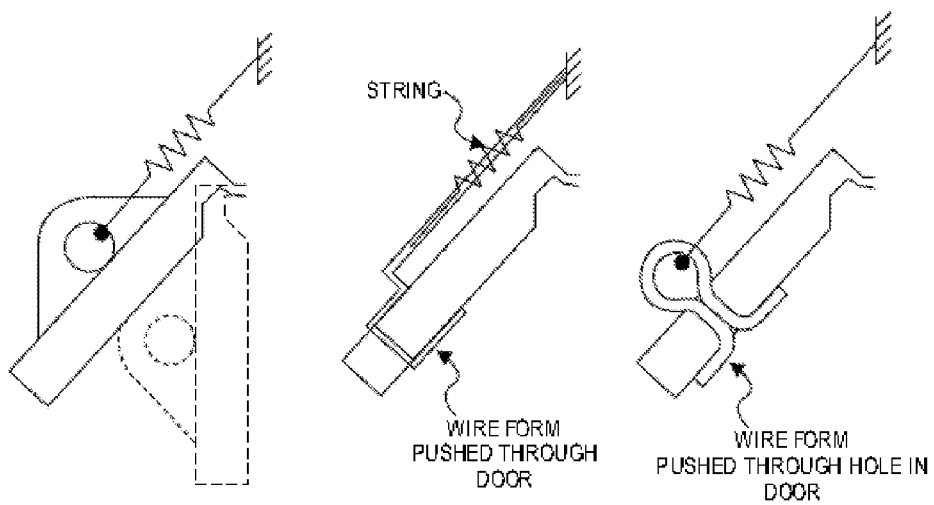
FIG. 44A
FIG. 44B
FIG. 44C

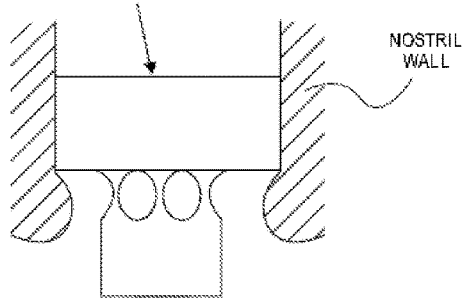
FIG. 46E
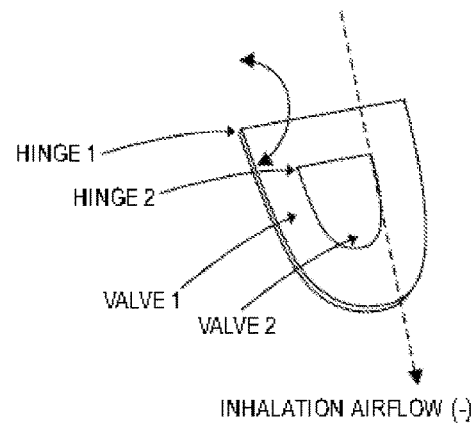
FIG. 47A
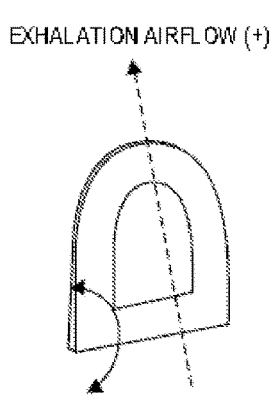
FIG. 47B
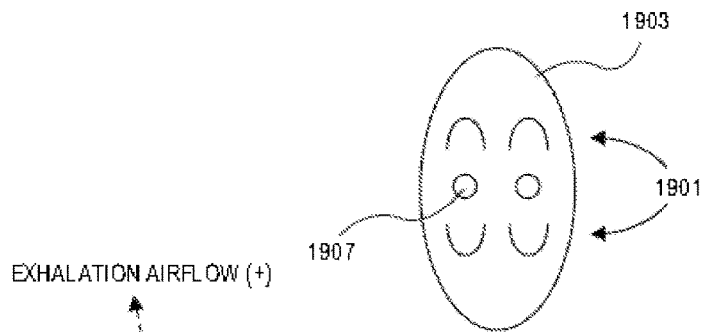
FIG. 48A
FIG. 47C $(P_1 - P_2) > P_T$ FIG. 54
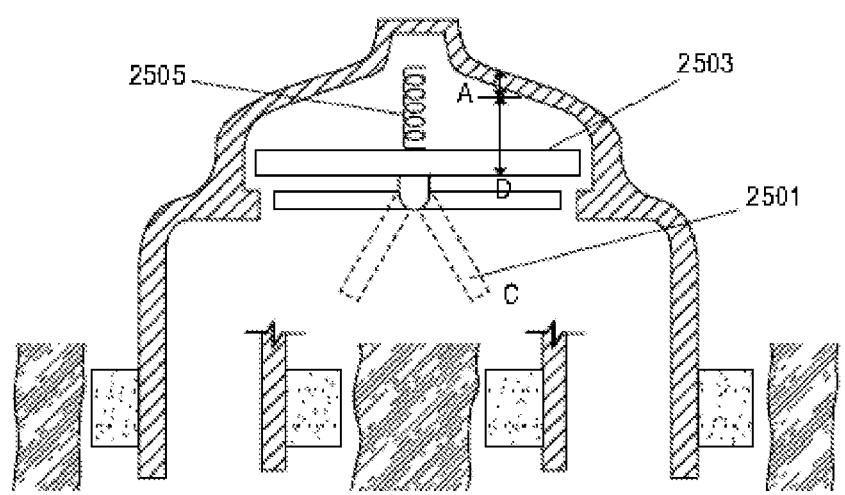
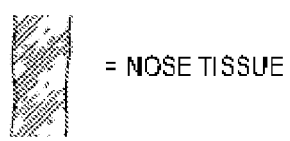 = NOSE TISSUE
 = FOAM
 = CHASSIS STRUCTURE

FLOPS DOWN DURING INHALATION

NEUTRAL

INSPIRATION

EXHALATION LOW P

EXHALATION HIGH P

NASAL RESPIRATORY DEVICES

CROSS-REFERENCE TO RELATED APPLICATIONS

This application claims priority as a continuation-in-part of U.S. patent application Ser. No. 12/877,836, filed on Sep. 8, 2010, titled "NASAL RESPIRATORY DEVICES FOR POSITIVE END-EXPIRATORY PRESSURE," Publication No. US-2010-0326447-A1, which claims priority as a continuation of U.S. patent application Ser. No. 11/811,401, filed on Jun. 7, 2007, titled "NASAL RESPIRATORY DEVICES FOR POSITIVE END-EXPIRATORY PRESSURE," now U.S. Pat. No. 7,806,120, which is a continuation-in-part of U.S. patent application Ser. No. 11/298,640, filed on Dec. 8, 2005, titled "NASAL RESPIRATORY DEVICES", now U.S. Pat. No. 7,735,492, which claims priority to U.S. Provisional Patent Application No. 60/634,715, filed on Dec. 8, 2004, each of which is herein incorporated by reference in its entirety. U.S. patent application Ser. No. 11/811,401 also claims priority to U.S. Provisional Patent Application No. 60/811,814, filed on Jun. 7, 2006, titled "RESPIRATORY DEVICES" and is herein incorporated by reference in its entirety.

This application also claims priority as a continuation-in-part of U.S. patent application Ser. No. 14/371,392, filed on Jul. 9, 2014, titled "NASAL DEVICES WITH VARIABLE LEAK PATHS, NASAL DEVICES WITH ALIGNERS, AND NASAL DEVICES WITH FLAP VALVE PROTECTORS," Publication No. US-2014-0345623-A1, which claims priority as a 35 35 U.S.C. §371 national phase application of PCT Application No. PCT/US2013/022121, filed Jan. 18, 2013, titled "NASAL DEVICES WITH VARIABLE LEAK PATHS, NASAL DEVICES WITH ALIGNERS, AND NASAL DEVICES WITH FLAP VALVE PROTECTORS," Publication No. WO 2013/109871, which claims priority to U.S. Provisional Patent Application No. 61/589,071, filed on Jan. 20, 2012, titled "NASAL DEVICES WITH VARIABLE LEAK PATHS, NASAL DEVICES WITH ALIGNERS, AND NASAL DEVICES WITH FLAP VALVE PROTECTORS," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The devices, methods, and kits described herein relate generally to the field of medicine and more particularly to the fields of cardiovascular medicine, sleep medicine, pulmonology, gastroenterology, and internal medicine. In this regard, the devices, methods, and kits described may be useful in the treatment of diseases including heart failure, hypertension, sleep apnea and other sleep disorders, snoring, chronic obstructive pulmonary disease (COPD), gastroesophageal reflux disease, and various inflammatory diseases, among others.

BACKGROUND OF THE INVENTION

Numerous disease states could benefit from the modification of patient respiration, including heart failure, sleep apnea and other sleep disorders, hypertension, snoring, chronic obstructive pulmonary disease (COPD), bronchitis, asthma, and many others.

Heart failure, or congestive heart failure (CHF), is a common clinical syndrome that represents the end-stage of a number of pulmonary and cardiac disease states. Heart failure is a degenerative condition that occurs when the heart muscle weakens and the ventricle no longer contracts normally. The heart can then no longer adequately pump blood to the body including the lungs. This may lead to exercise intolerance, or may cause fluid retention with subsequent shortness of breath or swelling of the feet. Over four million people are diagnosed with heart failure in the United States alone. Morbidity and mortality in patients with heart failure is high.

Sleep apnea is defined as the temporary absence or cessation of breathing during sleep. Airflow must be absent for some period of time longer than the usual inter-breath interval, typically defined as ten seconds for adults and eight seconds (or more than two times the normal respiratory cycle time) for infants. There are three general varieties of sleep apnea: central, obstructive, and mixed. In central sleep apnea, the patient makes no effort to breathe. In obstructive apnea, ventilatory effort is present, but no airflow results, because of upper airway closure. In mixed apnea, there is initially no ventilatory effort (suggestive of central sleep apnea), but an obstructive sleep apnea pattern becomes evident when ventilatory effort resumes. Finally, hypopnea is a temporary decrease in inspiratory airflow that is out of proportion to the individual's effort or metabolic needs. The terms sleep apnea and/or sleep disordered breathing may refer to hypopnea.

Hypertension refers to elevated blood pressure, and is a very common disease. Hypertension is characterized by elevated systolic and/or diastolic blood pressures. Despite the prevalence of hypertension and its associated complications, control of the disease is far from adequate. Only a third of people with hypertension control their blood pressure adequately. This failure reflects the inherent problem of maintaining long-term therapy for a usually asymptomatic condition, particularly when the therapy may interfere with the patient's quality of life, and when the immediate benefits of the therapy are not be obvious to the patient.

Chronic obstructive pulmonary disease (COPD) includes chronic bronchitis, emphysema and asthma. In both chronic bronchitis and emphysema, airflow obstruction limits the patient's airflow during exhalation. COPD is a progressive disease characterized by a worsening baseline respiratory status over a period of many years with sporadic exacerbations often requiring hospitalization. Early symptoms include increased sputum production and sporadic acute exacerbations characterized by increased cough, purulent sputum, wheezing, dyspnea, and fever. As the disease progresses, the acute exacerbations become more frequent. Late in the course of the disease, the patient may develop hypercapnia, hypoxemia, erythrocytosis, cor pulmonale with right-sided heart failure, and edema.

Chronic bronchitis is characterized by a chronic cough with sputum production leading to obstructed expiration. Pathologically, there may be mucosal and submucosal edema and inflammation and an increase in the number and size of mucus glands. Emphysema is characterized by destruction of the lung parenchyma leading to loss of elastic recoil, reduced tethering of airways, and obstruction to expiration. Pathologically, the distal airspaces are enlarged.

Asthma is another chronic lung condition, characterized by difficulty in breathing. People with asthma have extrasensitive or hyper-responsive airways. The airways react by obstructing or narrowing when they become inflamed or irritated. This makes it difficult for the air to move in and out of the airways, leading to respiratory distress. This narrowing or obstruction can lead to coughing, wheezing, shortness of breath, and/or chest tightness. In some cases, asthma may be life threatening.

In all of these diseases, current medical and surgical therapies are not completely effective, and there is considerable room for improvement. Two therapies that are used to treat these diseases are pulmonary rehabilitation (including pursed-lip breathing) and non-invasive mechanical ventilation.

Pulmonary rehabilitation is frequently used to treat patients suffering from a variety of medical ailments such as those mentioned. For example, COPD patients are taught new breathing techniques that reduce hyperinflation of the lungs and relieve expiratory airflow obstruction. One of the goals of this training is to reduce the level of dyspnea. Typically, these new breathing techniques include diaphragmatic and pursed-lip breathing. Pursed-lip breathing involves inhaling slowly through the nose and exhaling through pursed-lips (as if one were whistling), taking two or three times as long to exhale as to inhale. Most COPD patients instinctively learn how to perform pursed-lip breathing in order to relieve their dyspnea. Moreover, patients with asthma and other respiratory ailments, and even normal people during exercise, have been shown to use pursed-lip breathing, especially during times of exertion.

It is widely believed that producing a proximal obstruction (e.g., pursing the lips) splints open the distal airways that have lost their tethering in certain disease states. In other words, airways that would normally collapse during respiration remain open when the patient breathes through pursed-lips. Moreover, by increasing exhalation time, respiratory rate can be reduced and, in some cases, made more regular.

The medical literature has confirmed the utility of pursed-lip breathing in COPD patients. Specifically, it has been found that pursed-lip breathing by COPD patients results in a reduction in respiratory rate, an increase in tidal volumes, and an improvement of oxygen saturation. All of these effects contribute to a reduction in patient dyspnea. However, pursed-lip breathing requires conscious effort. Thus, the patient cannot breathe through pursed-lips while sleeping. As a result, the patient can still become hypoxic at night and may develop pulmonary hypertension and other sequelae as a result. Furthermore, the patient has to constantly regulate his own breathing. This interferes with his performing of other activities because the patient must pay attention to maintaining pursed-lip breathing.

Non-invasive positive pressure ventilation (NPPV) is another method of treating diseases that benefit from regulation of the patient's respiration. NPPV refers to ventilation delivered by a nasal mask, nasal prongs/pillows or face mask. NPPV eliminates the need for intubation or tracheostomy. Outpatient methods of delivering NPPV include bilevel positive airway pressure (BIPAP or bilevel) ventilator devices, or continuous positive airway pressure (CPAP) devices.

NPPV can deliver a set pressure during each respiratory cycle, with the possibility of additional inspiratory pressure support in the case of bi-level devices. NPPV has been shown to be very efficacious in such diseases as sleep apnea, heart failure, and COPD, and has become increasingly used in recent years. Many patients use CPAP or BIPAP at night while they are sleeping.

However, most patients experience difficulty adapting to nocturnal NPPV, leading to poor compliance. Mask discomfort is a very common problem for patients new to NPPV, because of the high pressures on the nose, mouth, and face, and because of uncomfortably tight straps. Nasal congestion and dryness are also common complaints that may vary by season. The nasal bridge can become red or ulcerated due to excessive mask tension. Eye irritation and acne can also result. Still other patients experience abdominal distention and flatulence. Finally, air leakage through the mouth is also very common in nasal NPPV patients, potentially leading to sleep arousals.

Both pursed-lip breathing and the use of NPPV have been shown to offer significant clinical benefits to patients with a variety of medical illnesses, including but not limited to COPD, heart failure, pulmonary edema, sleep apnea (both central and obstructive) and other sleep disordered breathing, cystic fibrosis, asthma, cardiac valve disease, arrhythmias, anxiety, and snoring. Expiratory resistance is believed to provide the bulk of clinical improvements when using pursed-lip breathing and NPPV, through a variety of physiologic mechanisms. In contrast, inspiratory support is not believed to offer clinical benefits in many patients. For example, in COPD, expiratory resistance facilitates expiration, increases tidal volume, decreases respiratory rate, and improves gas exchange. In the case of heart failure, it is felt that positive pressure in the airways (due to expiratory resistance) reduces pulmonary edema and improves lung compliance, decreases preload and afterload, increases $pO_2$, and decreases $pCO_2$. In many disease states, expiratory resistance helps maintain a more stable respiratory rate that can have profound clinical effects to the patient.

Positive end-expiratory pressure (PEEP) refers to pressure in the airway at the end of expiration that exceeds atmospheric pressure. Positive end-expiratory pressure has been used clinically mainly as a way to recruit or stabilize lung units and improve oxygenation in patients with hypoxemic respiratory failure. Traditionally, PEEP has been achieved using devices that apply continuous positive airway pressure (referred to as ventilators or CPAP devices), wherein both the inspiratory and expiratory portions of the circuit are pressurized above atmospheric pressure. However, CPAP devices (including modified devices such as "C-FLEX" devices manufactured by Respironics) are expensive, uncomfortable and cumbersome, leading to limited application and patient compliance.

Numerous disease states may benefit from the modification of patient respiration to induce PEEP, including heart failure, sleep apnea and other sleep disorders, hypertension, snoring, chronic obstructive pulmonary disease (COPD), bronchitis, asthma, and many others.

It would therefore be desirable to have a medical device and/or procedure that mimics the effect of pursed-lip breathing and/or the benefits of non-invasive ventilation without suffering from the drawbacks described above.

SUMMARY OF THE DISCLOSURE

Described herein are respiratory devices and methods for treating a variety disorders, including sleep apnea, snoring, hay fever, allergic rhinitis, and other allergic respiratory conditions. Some versions of these devices make use of expiratory resistance to mimic the effects of pursed-lip breathing and non-invasive ventilation (with or without positive end expiratory pressure, or PEEP).

For example, a whole-nose nasal respiratory device configured to engage both of a subject's nostrils may include: a first holdfast comprising a first rim forming a first passageway; a first airflow resistor within the first passageway, the first airflow resistor comprising a first flap valve that inhibits exhalation through a first nostril more than inhalation through the first nostril when the first holdfast is worn in the first nostril; a second holdfast comprising a second rim forming a second passageway; a second airflow resistor within the second passageway, the second airflow resistor comprising a second flap valve that inhibits exhalation through a second nostril more than inhalation through the second nostril when the second holdfast is worn in the second nostril; and a connector connecting the first rim to the second rim.

For example described herein are whole-nose nasal respiratory device configured to engage both of a subject's nostrils. These devices may include: a first rim forming a first passageway; a first airflow resistor within the first passageway, the first airflow resistor comprising a first flap valve that inhibits exhalation through a first nostril more than inhalation through the first nostril; a first holdfast on the first rim, the first holdfast securing the first rim in communication with the first nostril when the device is worn; a second rim forming a second passageway; a second airflow resistor within the second passageway, the second airflow resistor comprising a second flap valve that inhibits exhalation through a second nostril more than inhalation through the second nostril; a second holdfast on the second rim, the second holdfast securing the second rim in communication with the second nostril when the device is worn; and a connector connecting the first rim to the second rim.

For example, a whole-nose nasal respiratory device configured to engage both of a subject's nostrils may include: a first rim forming a first passageway, wherein the first rim is compressible; a first airflow resistor within the first passageway, the first airflow resistor comprising a first flap valve that inhibits exhalation through a first nostril more than inhalation through the first nostril; a second rim forming a second passageway, wherein the second rim is compressible; a second airflow resistor within the second passageway, the second airflow resistor comprising a second flap valve that inhibits exhalation through a second nostril more than inhalation through the second nostril; a connector comprising a clip connecting the first rim to the second rim. The first and second rims may be oval, or may have a generally oval shape when worn within the nostril(s).

The rim may be part of the holdfast, or it may be separate from the holdfast. The rim and/or holdfast may be adjustable. For example, an outer diameter of the rim and/or holdfast may be adjustable to fit into (or more comfortably into) a nostril.

The connector may be continuous with the rim and/or holdfast, or it may be separate. For example, the rim may be formed of the same material as the connector. The holdfast and/or rim and the connector may be formed of a polymeric material as described herein, and may be molded or otherwise formed as a single piece, or from multiple pieces combined together.

The first rim (and/or holdfast) and the second rim (and/or holdfast) may be oval.

The first holdfast and/or rim may form a seal between the respiratory device and the first nostril, and wherein the second holdfast and/or rim may form a seal between the respiratory device and the second nostril. The first and the second holdfast and/or rim may be formed of a compliant material. For example, the first and second holdfast may comprise silicone. In any of these variations, the first and second rim may comprise a compressible material and/or shape (e.g., a C-shape or broken oval shape). The first and second rim may comprise a silicone rubber.

Any of the devices described herein may include one or more leak paths, the one or more leak paths allowing air to flow through the device even when air is restricted by the first and the second airflow resistors. For example, the one or more leak paths comprise at least one aperture or channel through the valve, the at least one aperture or channel being open even when the valve is closed.

In use, a subject wearing the devices described herein may experience a positive end expiratory pressure of 0.1 to 30 cm H2O.

The device may include a therapeutic agent that comes into contact with the subject's nostrils when the nasal respiratory device is worn.

The connector may comprise one or more of: a clip, a tether, a strap, a band, a chain, and a string. In general, the connector bridges the first and second holdfasts when they are secured into the two nostrils, and may provide a grabbing or grasping region. For example, the connector may bridge between the two holdfasts and may be worn around the columella of the nose.

Any of the devices described herein may include a filter within either the first or second passageway.

The devices described herein include respiratory devices and methods for treating a variety of medical diseases through the use of such devices. Some versions of these devices make use of expiratory resistance to mimic the effects of pursed-lip breathing and non-invasive ventilation (with or without positive end expiratory pressure, or PEEP).

The respiratory device described herein is adapted to be removably secured in communication with a respiratory cavity. A respiratory cavity may be a nasal cavity (e.g., nostril or nasal passage) or an oral cavity (e.g., mouth or throat). The respiratory device comprises a passageway, an airflow resistor in communication with the passageway, and a holdfast for removably securing the respiratory device in communication with the respiratory cavity. The airflow resistor alters the flow of air passing within the passageway. In particular, the airflow resistor may alter the flow of air within the passageway by increasing the resistance to the flow of air in the passageway. The respiratory device may be applied or removed by the user of the device, and thus, does not need to be applied by a physician or other healthcare personnel.

In one version, the respiratory device is adapted to be removably secured in communication with a nasal cavity. The respiratory device may also comprise a rim for supporting the passageway. The rim may be, for example, a frame, a framework, or a tube comprising a material and a shape that prevents the passageway from collapsing during use, particularly when the device is used during repeated cycles of inhalation and exhalation. In some versions, the rim defines at least a portion of a wall of the passageway. However, the rim may support a passageway (or a portion of the passageway) which has another material (e.g., a medicinal or protective layer) that defines all or part of the inner lumen of the passageway.

In one version, the airflow resistor increases the resistance of air being exhaled and/or inhaled through the passageway. The airflow resistor may have an orientation, so that resistance to airflow in one direction is greater than the opposite direction. For example, the airflow resistor may increase the resistance to air exhaled through the passageway of the respiratory device without substantially increasing the resistance to air inhaled through the passageway. The airflow resistor may increase the resistance to air exhaled through the passageway of the respiratory device more than it increases the resistance to air inhaled through the passageway. Furthermore, the respiratory device may be reversible, so that in one orientation resistance to airflow through the device during inhalation is higher than resistance to airflow through the device during exhalation. By reversing the device (or by reversing the airflow resistor portion of the device), resistance to airflow through the device during exhalation is higher than resistance to airflow through the device during inhalation.

In one version, the airflow resistor decreases the resistance to air exhaled and/or inhaled through the passageway when the airflow across the airflow resistor or the air pressure differential across the airflow resistor exceeds a threshold level. Thus, for example, the respiratory device may not inhibit airflow (or not substantially inhibit airflow) in the passageway during a cough, sneeze, nose blowing or other high airflow/high pressure event. The threshold value may be determined based on measurements or approximations from a particular user. For example, the threshold may be a value above the normal peak of airflow or pressure during normal expiration. The threshold value may also be determined based on a typical value approximated from many patients This threshold pressure for example may fall within the range of 0.1 to 1000 cm H2O pressure, more preferably within the range of 0.5 and 100 cm H2O pressure, and most preferably within the range 1.0 and 50 cm H2O pressure. In one version, the airflow resistor increases the resistance to air exhaled and/or inhaled through the passageway when the airflow across the airflow resistor or the air pressure differential across the airflow resistor falls below a threshold level. Thus, the respiratory device may create a PEEP (positive end expiratory pressure) effect by, for example, preventing complete exhalation based on the pressure applied against the device, if the pressure and/or airflow at the end of exhalation are below the threshold level selected. The threshold level may correspond to an air pressure differential, air pressure, or airflow measured from an individual patient, or it may correspond to a typical value, such as a typical value measured from a sample of patients. This threshold pressure for example may fall within the range of 0.1 to 150 cm H2O, more preferably within the range of 0.5 to 30 cm H2O, and most preferably within the range of 1.0 to 25 cm H2O.

In some versions, the airflow resistor is a nested airflow resistor. Nested airflow resistors may be airflow resistors configured to alter the flow of air in the passageway under different conditions (e.g., different directions or different flow rates or pressure differentials across the resistor). For example, a nested airflow resistor may be a combination of multiple airflow resistors "nested" so that they affect the flow of air in the passageway under different conditions. Thus a first flap valve that increases the resistance to airflow in a first direction may be combined with a second flap valve that opens when the resistance to airflow in the first direction is above a threshold. In one version, the second flap valve is integral to the flap portion of the first flap valve.

Virtually any type of airflow resistor may be used with the respiratory devices described herein, including flap valves, membrane valves, hingeless valves, balloon valves, stopper-type valves, ball valves, and the like. The device may include a variety of "one-way valve structures," or other flow responsive elements that open to inspiration and close partially or completely to expiration. In one version, the airflow resistor is a flap valve. The airflow resistor may be a plate which is held within a nasal cavity that occludes some portion of the luminal cross-sectional area of the nasal cavity. The airflow resistor may selectively increase resistance to expiration while minimally or trivially increasing flow resistance to inspiration. When closing during expiration, the airflow resistor may or may not fully prevent airflow, depending on the design of the device.

In one version, the airflow resistor is configured to alter the inspiratory time:expiratory time (I:E) ratio of a user wearing the respiratory device to be between about 3:1 and about 1:10. In another version, the airflow resistor is configured to alter the inspiratory time:expiratory time ratio of a user wearing the respiratory device to be between about 1:1.5 and about 1:4. In another version, the airflow resistor is configured to alter the inspiratory time:expiratory time ratio of a user wearing the respiratory device to about 1:3.

In some versions of the respiratory device the holdfast removably secures the respiratory device in communication with a nasal cavity of a user so that at least some of the air exchanged between the nasal cavity and the external environment of a user passes through the respiratory device. The holdfast may removably secure the respiratory device to a user's nasal cavity so that all of the air exchanged between the nasal cavity and the user's external environment passes through the respiratory device. The respiratory device may be secured at least partly within the nasal cavity, or totally within the nasal cavity, or totally external to the nasal cavity, but in communication with the nasal cavity. The device may be adapted to communicate with the nasal cavity by being removably secured within or near the nares.

The respiratory device may be partly secured in the nasal cavity of a user so that an outer surface of the respiratory device exerts pressure against the nasal cavity. For example, an outer surface (e.g., the holdfast) may be oversized so that it exerts pressure against the nasal cavity.

In some versions of the respiratory device, the holdfast removably secures the respiratory device in communication with both of a user's nasal cavities (e.g., both nostrils or nasal passages). In some versions, the holdfast may removably secure the respiratory device within both of a user's nasal cavities (e.g., nostrils or nasal passages). In some versions, the holdfast removably secures the respiratory device in communication with a user's oral cavity and at least one nasal cavity.

In some versions, the respiratory device further comprises an active agent. In some versions, this active agent is a drug (e.g., a medicament). In some versions, this active agent comprises an odorant, such as a fragrance. In some versions, the active agent comprises menthol, eucalyptus oil, and/or phenol.

In some versions, the respiratory device further comprises a filter. This filter may be a movable filter, such as a filter that filters air flowing through the passageway in one direction more than another direction (e.g., the device may filter during inhalation but not expiration).

In some versions, the respiratory device further comprises a respiratory gas supply. For example, a respiratory gas supply (e.g., Oxygen, or any mixture of respiratory gases) may be used in conjunction with a respiratory device. In some versions, the respiratory device is adapted to connect to a respiratory gas supply.

In some versions, the holdfast comprises a conformable material. For example, the device may fit snugly within or against a respiratory cavity by compressing the holdfast (or a portion of the holdfast), which may expand to fit in or against the respiratory cavity securing the device in place, and preventing air exchange between the respiratory cavity and the external environment unless the air passes through the respiratory device.

Also described herein are respiratory devices adapted to removably secure to a nasal cavity comprising a passageway, a rim, and a holdfast for securing the respiratory device to at least one nasal cavity. The rim has sufficient strength to support the passageway in the open state when the device is inserted into the nasal cavity. The respiratory device may be applied or removed by the user.

Also described herein are respiratory devices adapted to be removably secured in a nasal cavity comprising a passageway, a filter within the passageway, and a holdfast for securing the respiratory device within a nasal cavity. The respiratory device may be applied or removed by a user. In one version, the filter is a movable filter for filtering air flowing through the device during either inhalation (but not exhalation) or during exhalation (but not inhalation). For example, if the movable filter filters air during inhalation, it may then move at least partly out of the path of airflow during exhalation.

Also described herein are methods of regulating pCO2 in a patient comprising removably securing a respiratory device in communication with a patient's nasal cavity, wherein the respiratory device comprises an airflow resistor that inhibits expiration more than it inhibits inhalation.

Also described herein are methods of simulating pursed-lip breathing in patients comprising removably securing a respiratory device in communication with a patient's nasal cavity, wherein the respiratory device comprises an airflow resistor that inhibits expiration more than it inhibits inhalation.

Also described herein are methods of treating a sleeping disorder comprising removably securing a respiratory device in communication with a patient's nasal cavity, wherein the respiratory device comprises an airflow resistor that inhibits expiration more than it inhibits inhalation.

Also described herein are methods of treating chronic obstructive pulmonary disease comprising removably securing a respiratory device in communication with a patient's nasal cavity, wherein the respiratory device comprises an airflow resistor that inhibits expiration more than it inhibits inhalation.

Also described herein are methods of treating a cardiovascular disorder comprising removably securing a respiratory device in communication with a patient's nasal cavity, wherein the respiratory device comprises an airflow resistor that inhibits expiration more than it inhibits inhalation.

Also described herein are methods of treating a gastroenterologic disorder (such as gastroesophageal reflux disease or hiatal hernia) comprising removably securing a respiratory device in communication with a patient's nasal cavity, wherein the respiratory device comprises an airflow resistor that inhibits expiration more than it inhibits inhalation.

Also described herein are kits comprising a respiratory device as described herein and instructions on the use of the respiratory device.

In some versions, the devices are removable and are placed within the nose and/or mouth of the patient.

In some versions of the respiratory device, the device is adapted to be in communication with an oral cavity by securing substantially within the oral cavity. The same embodiments described above for respiratory devices that may be secured in communication with a nasal cavity may be used with these versions. The device may be substantially within the oral cavity when most (but not necessarily all) of the device is within the oral cavity. For example, a small portion of the device may project from the oral cavity. Of course, in some variations, a device that is substantially within the oral cavity may refer to a device that is held entirely within the oral cavity.

Some of the devices feature either non-moving parts, or moving parts that can partially obstruct the breathing passageway on expiration and minimally obstruct the breathing passageway on inspiration. That is, the direction of the airflow and the pressure differential across the valve may determine the degree of obstruction. The respiratory devices may be used during the day, night, or both. For example, these devices may be worn during sleep and/or during waking hours. Furthermore, the devices may be kept in place for long durations, such as several hours, days, or weeks.

The devices and methods described herein may be used to treat a variety of disease states, and can be inserted and removed depending on need. These devices may also comprise a positioner to assist in positioning the device in communication with a respiratory orifice such as the nasal cavities. The positioner may be attached to a device, for example, as a handle or grip. The positioner may also be a device in which the respiratory device sits until it is secured in communication with a respiratory orifice, and then the positioner may be removed, leaving the respiratory device in place.

In some versions, the respiratory device comprises a nasal device useful for treating a variety of disease states. A user may conveniently insert and remove the device depending on need.

The methods for treating patients suffering from a variety of medical ailments through the use of an expiratory resistor broadly comprise creating a resistance to expiratory flow in or around the oral and/or nasal cavities, typically within or around the mouth or the nares. The methods may comprise use of any of the devices described above. For example, airflow resistance may be created by placing a flow resistor, either one with a fixed flow resistance or one with a variable flow resistance, i.e., which is higher to expiration than inspiration.

As mentioned, the nasal respiratory devices and methods described herein may be used for treating a variety of medical diseases through the use of such devices.

For example, described herein are nasal respiratory devices for inducing positive end-expiratory pressure adapted to be secured (e.g., removably secured) in communication with a nasal cavity. These devices may include a passageway, and an airflow resistor in communication with the passageway, wherein the airflow resistor is configured to have a non-zero threshold pressure for opening during expiration so that the airflow resistor is closed during expiration when the pressure across the airflow resistor is below the threshold pressure for opening, but the airflow resistor opens during expiration when the airflow resistor exceeds the threshold pressure for opening during expiration. These devices may also include a holdfast configured to secure the airflow resistor in communication with the nasal cavity without covering the subject's mouth.

As described in more detail herein, any appropriate threshold pressure for opening during expiration may be used. For example, the threshold pressure for opening (which may also be referred to as the threshold for opening) of the airflow resistor may be less than about 20 cm H2O, less than about 15 cm H2O, less than about 10 cm H2O, less than about 8 cm H2O, more than about 4 cm H2O, or between a range of pressures. For example, the threshold pressure for opening may be between about 0.5 cm H2O and about 20 cm H2O, or between about 0.5 cm H2O and about 15 cm H2O, or between about 4 cm H2O and about 20 cm H2O. The threshold for opening is typically much less than the pressure resulting from coughing, sneezing, or the like.

In some variations, the airflow resistor may further comprise a non-zero threshold pressure for closing during expiration, such that the airflow resistor closes during expiration when the pressure across the airflow resistor falls below the threshold pressure for closing. Any appropriate threshold pressure for closing during expiration may be used. For example, the threshold pressure for closing during expiration may be greater than about 1 cm H2O, greater than about 2 cm H2O, greater than about 3 cm H2O, greater than about 4 cm H2O, greater than about 10 cm H2O, etc. In some variations, the threshold pressure for closing during expiration is between a range of values, such as between about 0.5 cm H2O and about 20 cm H2O, between about 0.5 cm H2O and about 15 cm H2O, between about 0.5 cm H2O and about 10 cm H2O, between about 0.5 cm H2O and about 5 cm H2O. The threshold pressure for closing during expiration may be approximately the same as the threshold pressure for opening during expiration, or it may be different.

In some variations the airflow resistor of the device has a threshold pressure for opening that is less than the threshold pressure for closing. In this variation, the device opens when the pressure exceeds the threshold for opening (e.g., at 4 cm H2O), and then closes at a predetermined time after opening after which the pressure must reach a second threshold for opening (e.g., at 10 cm H2O). This may allow a user to breathe out easily at first (possibly improving tolerance for the device) and then have a larger PEEP pressure at the end of expiration.

Also described herein are nasal respiratory devices for inducing positive end-expiratory pressure adapted to be secured in communication with a nasal cavity including a passageway and an airflow resistor in communication with the passageway, wherein the airflow resistor comprises a biased valve having a non-zero threshold pressure for opening during expiration, so that the airflow resistor is closed during expiration when the pressure across the valve is below the threshold pressure for opening, but the valve opens during expiration when the pressure across the valve exceeds the threshold pressure for opening during expiration. These devices may also include a holdfast configured to secure the airflow resistor only in communication with a nasal cavity, or with both nasal cavities (e.g., but not the mouth).

In some variations, the airflow resistor of this device includes a second valve. Any appropriate valves may be used as part of the airflow resistor. These devices are described in greater detail below, but include biased valves configured as a nested valve, bistable valves, and the like.

Also described herein are nasal respiratory devices for inducing positive end-expiratory pressure adapted to be secured in communication with a nasal cavity that include a passageway and an airflow resistor in communication with the passageway, where the airflow resistor has a first valve configured to open during inspiration and close during expiration and a second valve configured to open during exhalation and close during inspiration, and the second valve is configured so that it does not open until the pressure across the second valve exceeds a non-zero threshold pressure for opening. These devices may also include a holdfast configured to secure the airflow resistor in communication with the nasal cavity.

In some variations, the second valve is nested with the first valve. The first valve or the second valve (or both) may be a may be a flap valve. The second valve may be a biased valve (including but not limited to a biased flap valve). The second valve may be a bistable valve.

Also described herein are nasal respiratory devices for inducing positive end-expiratory pressure adapted to be secured in communication with a nasal cavity. These devices may include a first passageway and a second passageway, and an airflow resistor comprising a first valve in communication with the first passageway and a second valve in communication with the second passageway, wherein the first valve is configured to open during inspiration and close during expiration and the second valve is configured to close during inspiration and open during expiration when the pressure across the second valve exceeds a non-zero threshold pressure for opening. These devices may also include a holdfast configured to secure the first and second passageways in communication with the nasal cavity. As mentioned above, the first valve or the second valve (or both) may be a may be a flap valve. The second valve may be a biased valve (including but not limited to a biased flap valve). The second valve may be a bistable valve.

Also described herein are methods of treating a disorder. These methods may include the steps of securing a nasal respiratory device in communication with a subject's nasal cavity without covering the subject's mouth, wherein the respiratory device comprises an airflow resistor configured to have a non-zero threshold pressure for opening during expiration so that the airflow resistor is closed during expiration when the pressure across the valve is below the threshold pressure for opening, but the airflow resistor opens during expiration when the pressure across the airflow resistor exceeds the threshold pressure for opening during expiration, and allowing the subject to breathe at least partly through the nasal respiratory device. The disorder treated may be selected from the group consisting of: respiratory disorders, sleep disorders, gastroenterologic disorders, and cardiovascular disorders.

As described herein, the nasal respiratory device may be secured at least partially within the subject's nasal cavity (e.g., by a compressible holdfast). In some variations, a nasal respiratory device may be secured at least partially over the subject's nasal cavity (e.g., by an adhesive holdfast).

BRIEF DESCRIPTION OF THE DRAWINGS

FIG. 5 shows a respiratory device adapted to fit substantially within the nasal cavity.

FIG. 6 shows a cross-sectional view of the device shown in FIG. 4, where an airflow resistor is shown within the device.

FIGS. 7A and 7B show cross-sectional views of the device shown in FIG. 4; FIG. 7A shows the device during inhalation, and FIG. 7B shows the device during exhalation.

FIGS. 8A and 8B are perspective views of a respiratory device showing an airflow resistor during exhalation (FIG. 8A) and inhalation (FIG. 8B), respectively.

FIGS. 9A and 9B are perspective views of a respiratory device having an airflow resistor where the airflow resistor is shown during exhalation (FIG. 9A) and inhalation (FIG. 9B), respectively.

FIG. 10 is a perspective view of a respiratory device having an airflow resistor where the airflow resistor is shown during exhalation.

FIG. 11 is a perspective view of a respiratory device having an airflow resistor where the airflow resistor is shown during exhalation.

FIG. 15A shows the airflow resistor during higher levels of exhalation airflow and/or pressure. FIG. 15B shows the airflow resistor during lower levels of exhalation airflow and/or pressure. FIG. 15C shows the airflow resistor during inhalation.

FIGS. 17A and 17B are perspective views of a respiratory device having an airflow resistor where the airflow resistor is shown during exhalation (FIG. 17A) and inhalation (FIG. 17B), respectively.

FIGS. 18A and 18B show cross-sectional views of a respiratory device having an airflow resistor where the airflow resistor is shown during inhalation (FIG. 18A) and exhalation (FIG. 18B), respectively.

FIGS. 19A and 19B are cross-sectional views of a respiratory device having an airflow resistor where the airflow resistor is shown during low pressure and/or low airflow exhalation (FIG. 19A), and then during high pressure and/or high airflow exhalation (FIG. 19B).

FIG. 20 is a perspective view of a respiratory device where the device is removable and adapted for the nasal cavity.

FIG. 21 is a perspective view of a respiratory device where the device is removable and adapted for the nasal cavity.

FIG. 36 shows another example of a representative resistive profile for a differential resistor with a threshold for opening and a threshold for closing.

FIGS. 37A and 37B show side views through a portion of one variation of a respiratory device having nested flap valves.

FIG. 37C shows a cross-section view through the valve show in FIG. 37A.

FIG. 37D shows a detailed view of the flap valve shown in FIGS. 37A-37C.

FIGS. 39A, 39B and 39C schematically illustrate different bias placement in a flap valve for use with the PEEP configured devices described herein.

FIG. 40A shows a cross-sectional view of a door-within-a-door valve.

FIG. 40B shows a top view of the valve of FIG. 40A.

FIGS. 41A, 41B and 41C show top, side cross-section and bottom views of a valve having a living hinge as described herein.

FIGS. 41D, 41E and 41F show top, side cross-section and bottom views of another airflow resistor having a living hinge, similar to the valve shown in FIGS. 41A-41C.

FIG. 43B shows an elastomeric component of the respiratory device shown in FIG. 43A.

FIG. 43C shows a top view of the respiratory device shown in FIG. 43A

FIGS. 44A, 44B and 44C show different variations of an anchored bias that may be used with an expiratory flap valve as shown in FIGS. 43A-43C.

FIG. 46E shows a profile of the device illustrated in FIGS. 46A-46D within a nasal cavity.

FIGS. 47A, 47B and 47C illustrate the operation of nested flap valve.

FIGS. 48A and 48B illustrate different variations of a flap valve having additional cutout valves.

FIG. 54 shows a respiratory device combining airflow through both nostrils, as described herein.

DETAILED DESCRIPTION

Figure 1:
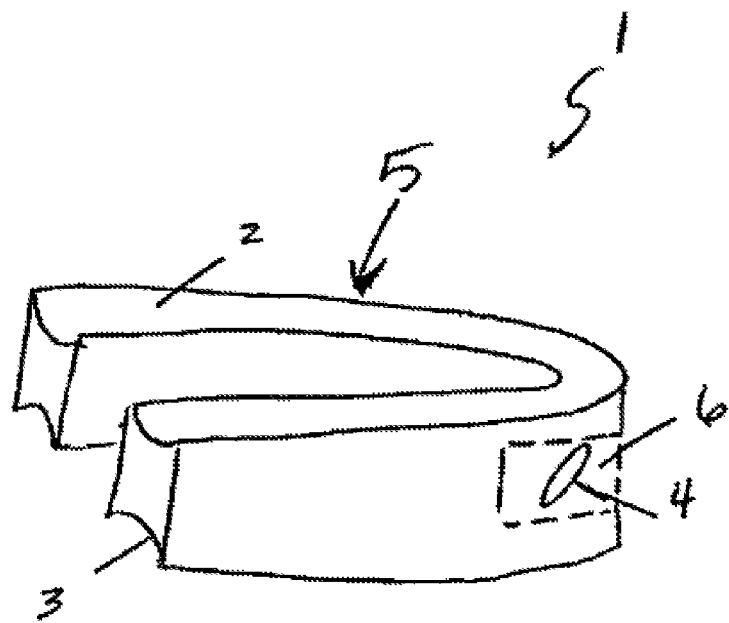
FIG. 1 is a perspective view of a respiratory device adapted for an oral cavity.

Described here are respiratory devices, kits, and methods for their use in improving respiratory and cardiovascular function. In general, the respiratory devices are referred to as respiratory devices or simply as "devices." The devices and methods described herein may be useful to treat a variety of medical disease states, and may also be useful for non-therapeutic purposes. The devices and methods described herein are not limited to the particular embodiments described. Variations of the particular embodiments may be made and still fall within the scope of the appended claims. It is also to be understood that the examples and particular embodiments described are not intended to be limiting. Instead, the scope of the present invention will be established by the appended claims.

As used in this specification, the singular forms "a," "an," and "the" include plural reference unless the context clearly dictates otherwise. Unless defined otherwise, all technical and scientific terms used herein have the same meaning as commonly understood by one of ordinary skill in the art.

The respiratory devices described herein alter airflow into and out of the lungs through a respiratory cavity such as the mouth and/or the nostrils of the nose. The respiratory devices typically include an airflow resistor capable of at least partly obstructing airflow, particularly airflow in one direction (e.g., expiration) more than the opposite direction (e.g., inhalation). In particular, the respiratory devices may be used to increase the resistance to expiration during the expiratory phase of the respiratory cycle. Many of the respiratory devices described herein may prevent collapse of airways and airflow conduits, provide a method of drug delivery, and filter air of undesirable compounds or agents.

The respiratory devices described herein generally comprise an airflow passageway and an airflow resistor. The airflow passageway (or "passageway") generally defines a channel allowing the passage of air. The passageway may be of any suitable size or shape; however it is configured so that when the respiratory device is worn by a patient, the passageway comprises an opening leading toward the patient's lungs in fluid connection with an opening that leads away from the patient's lungs. The term "patient" is used to describe any user of the respiratory device, including users who are not using the respiratory device for therapeutic purposes. The airflow passageway may be any suitable length. For example, the passageway may be as short as the airflow resistor will allow (e.g., extending only enough to support the airflow resistor). Similarly, the airflow passageway may be longer than the space required to support the airflow resistor. For example, in versions of the respiratory device adapted for at least partial insertion into a nasal cavity, the airflow passageway way may be approximately as long as the length of an average nares. In some versions, the passageway extends the length of an average nasal chamber.

The neutral diameter of the passageway may be of any appropriate size. Neutral diameter refers to the diameter of the passageway when the device allows air to flow through the passageway without additional resistance (e.g., due to an airflow resistor). In particular, the diameter of the passageway may depend upon configuration of the respiratory device. For example, respiratory devices configured to be inserted within the nasal cavity (e.g., a nasal chamber) may have a diameter that is approximately the diameter of a narrow portion of the nasal cavity, or slightly narrower. Respiratory devices configured to be secured over an oral cavity or a nasal cavity may have passageways of larger diameters. Furthermore, the diameter of a passageway may vary across the length of the device.

The airflow passageway may comprise a dedicated structure defining the inner wall of the airflow passageway, or it may be a structural component of the device. For example, the passageway may comprise a passage wall defined by a rim. A rim may be a tube (or tunnel) of material of any appropriate thickness. The rim may also be a frame, rather than a complete tube. The rim may comprise a sufficiently rigid material so that it can support the passageway, and prevent the passageway from collapsing during use and during respiration. In some versions, the rim comprises a compressible material that may be compressed to facilitate insertion and removal, while maintaining the ability to support the passageway and prevent complete collapse of the passageway during respiration. The rim may also be somewhat compressible during respiratory flow. The airflow passageway (including a rim portion) may also serve as an attachment site for other components such as airflow resistors, filters, anchors, etc.

The rim may be any suitable shape or size. For example, the rim may comprise a ring shape or an oval shape. The rim may have an inner diameter which is equivalent to (or larger than) the diameter of the passageway. In some versions, the rim comprises a material having strength sufficient to prevent the collapse of a respiratory device that has been inserted into a nasal cavity. For example, the rim may comprise a metal, a polymer (particularly stiff polymers), etc. In some versions, the rim may comprise softer or "weaker" materials which are formed or arranged so that the final shape of the rim has sufficient strength to prevent the collapse of the respiratory device during use.

In some versions, the airflow passageway does not include a dedicated structure such as a rim. For example, the airflow passageway of the respiratory device may be a passageway through another component of the device, such as holdfast. In some versions, the airflow passageway is defined by a passageway through a holdfast.

Airflow Resistor

An airflow resistor is typically positioned in communication with at least one airflow passageway, so that at least some of the air flowing through the passageway passes the airflow resistor. Thus, an airflow resistor modulates, alters, varies, or keeps constant the amount of resistance, the degree of airflow, or the pressure differential across the device or through a passageway in the device. In some versions, the airflow resistor inhibits airflow more greatly in one direction than the opposite direction. Thus, the airflow resistor may regulate airflow to and from the lungs. Some versions of the device have a greater resistance to exhalation than to inhalation during use.

In some versions of the respiratory device, the airflow resistor comprises a valve that does not appreciably impede airflow in a certain direction (e.g., inspiration), and that partially or completely impedes airflow in the other direction (e.g., expiration). In some embodiments, the valve allows for an expiratory obstruction to be relieved if a certain degree of airflow or pressure differential across the device is achieved, as might be the case with coughing or nose blowing. For example, in some embodiments, the valve comprises a flap made of a shape memory or deformable material (e.g., an elastic material); when the pressure differential across the valve (the expiratory airflow pressure) is large enough, the flap bends upon itself, thereby relieving the obstruction. This may be important during coughing and may also facilitate the clearance of mucous and other substances during coughing. After the cough, the flap returns to its original, non-bent conformation.

Examples of different types of airflow resistors are described below and illustrated in FIGS. 6, 8, 9, 10, 11, and 13-19. Any airflow resistance device capable of altering the resistance of air (e.g., due to inspiration and/or expiration) passing through an air passageway may be used, particularly devices which selectively increase the resistance of air flow in one direction more than in the opposite direction. Valve-type airflow resistors are particularly suitable. Examples of valves which may be used as airflow resistors include: flap valves (having one or more flaps); hingeless valves; stopper-type valves; membrane-type valves; ball valves; balloon-type valves; and the like. This list is not intended to be exhaustive, and other types of selective airflow resistors may be used. Moreover, multiple airflow resistors may also be used, which may include combinations of different types of airflow resistors.

The respiratory device may further comprise a holdfast for releasably securing the device in communication with a nasal and/or oral cavity. The holdfast may facilitate the positioning and securing of the device in a desired location, such as over or within (e.g., substantially within) a respiratory orifice. In particular, the holdfast may allow the device to be anchored, positioned, and/or stabilized in any location that is subject to respiratory airflow such as a respiratory cavity.

Examples of respiratory cavities include nasal and oral cavities. Nasal cavities may comprise the nostrils, nares or nasal chambers, limen, vestibule, greater alar cartilage, alar fibrofatty tissue, lateral nasal cartilage, agger nasi, floor of the nasal cavity, turbinates, sinuses (frontal, ethmoid, sphenoid, and maxillary), and nasal septum. The term "nasal cavity" may refer to any sub-region of the Nasal Fossa (e.g., a single nostril, nare, or nasal chamber).

An oral cavity includes the cavity of the mouth (e.g., vestibule and mouth cavity proper), and any sub-region thereof, including or more than one of the following structures: maxilla, mandible, gums, lips, teeth, jaw, tongue, hard or soft palate and the recess or gap between the teeth/gums and the lips.

In some versions, the holdfast may also secure a seal between the respiratory device and the respiratory airway, so that at least some of the air exchanged between the outside of the patient and the respiratory airway must pass through the respiratory device. In some versions, the holdfast seals the device in communication with a respiratory cavity completely, so that all air must be exchanged through the device. In some versions, the holdfast seal is incomplete, so that only some of the air exchanged between the patient and the external environment passes through the device. As used herein, "air" may be air from environment external to the patient, or it may be any respiratory gas (e.g., pure or mixed oxygen, $CO_2$, heliox, or other gas mixtures provided to the user).

In some versions, the holdfast may comprise an anchor or anchor region.

In some embodiments, the device is to be placed by the patient or the healthcare provider in communication with an oral cavity. In this case, the holdfast may comprise any suitable mechanism for securing the device in position in communication with an oral cavity. The holdfast may comprise insertive (e.g., mouthpiece-type) and non-insertive mechanisms. A non-insertive holdfast may comprise a surface configured to mate with the outer surface of a patient's face to secure the device. For example, a holdfast may comprise an adhesive bandage, a strap, or any other structure capable of securing the device in communication with a user's respiratory cavity. The holdfast may comprise a removable region that contours to interfaces with the lips, gums, teeth, tongue and/or soft palate of the user, allowing the user to insert or remove the device as needed. Alternatively, the device can be held in place by utilizing the area in between the gums and teeth or lips.

In other embodiments, the device is to be placed by the patient or the healthcare provider in or around the nasal cavity. Holdfasts appropriate for nasal cavities may secure the device in position within a nasal cavity (e.g., through one or both nostrils) or against surrounding structures. The holdfast may comprise a shape, surface or material that secures the device in communication with a nasal cavity. For example, the holdfast may comprise a cylindrical shape that allows the device to fit securely or snugly within a nostril. The outer surface of the device may comprise a holdfast including an adhesive material. In addition to holding the device in place, the holdfast may also partially or completely seal the device in communication with the nasal cavity. The holdfast may comprise insertive and/or non-insertive mechanisms. In some versions, the holdfast comprises a mechanical connection between the device and the user, such as a clip, straps, and the like.

The holdfast may be formed from a soft or compliant material that provides a seal, and may enhance patient comfort. Furthermore, compliant materials may reduce the likelihood that the device cuts off blood flow to the part of the respiratory cavity and surrounding regions (mouth or nose) to which the device is anchored. This compliant material may be one of a variety of materials including, but not limited to, plastic, polymers, cloth, foamed, spongy, or shape memory materials. Shape materials include any that have a preferred conformation, and after being deformed or otherwise deflected or altered in shape, have tendency to return to a preferred conformation. Soft shape memory materials may include, but are not limited to, urethane, polyurethane, sponge, and others (including "foamed" versions of these materials). Alternatively, the holdfast may not be soft or compliant and may instead be a rigid structure that interfaces directly with the respiratory orifice. For example, in versions of the respiratory device configured to be used at least partly within a nasal cavity, it is understood that the device may fit completely within a nostril (or both nostrils), or may project out of the nostril, depending on the particular embodiment. In some cases, the device may be placed high enough within the nasal cavity so that it cannot be seen within the nostril. In some embodiments the device may be located completely outside of the nose, for example, in some versions the holdfast has a shape that conforms to the outside surface of the nose. Thus, the holdfast may comprise one or more straps, bands, or the like to ensure an adequate fit and/or seal maintaining the device in communication with the nasal cavity. In another embodiment the holdfast may comprise one or more projections that are inserted within the nostrils. In some versions, a device may be placed at least partly in both nostrils, and may comprise a bifurcated passageway or two passageways that the holdfast places in communication with the nasal cavity through each nostril. In this case, the inspiratory and/or expiratory airflow to and from the lungs may be regulated through each nostril separately or together. In some versions, separate devices may be placed at least partly in each nostril, and may be connected to each other and/or the patient using a clip, tether, strap, band, chain, string, or the like. Such a system would facilitate subsequent removal of the device and make migration of the devices deeper into the nasal cavity less likely. Finally, in some devices, an adhesive flap may be present to help attach the device to the inside or outside of the nose (including the nostrils), to the oral cavity, to the neck, or to the face.

Materials

Respiratory devices may be made from any appropriate material or materials. In certain embodiments, the devices include a shape memory element or elements, as part of the holdfast, in the airflow resistor, or in giving form to the passageway. Any convenient shape memory material that provides for flexibility and resumption of configuration following removal of applied force may be employed in these embodiments. For example, shape memory alloys may be used. A variety of shape memory alloys are known, including those described in U.S. Pat. Nos. 5,876,434; 5,797,920; 5,782,896; 5,763,979; 5,562,641; 5,459,544; 5,415,660; 5,092,781; 4,984,581; the disclosures of which are herein incorporated by reference in their entirety. The shape memory alloy that is employed should generally be a biocompatible alloy. Biocompatible alloys may include nickel-titanium (NiTi) shape memory alloys sold under the Nitinol™ name by Memry Corporation (Brookfield, Conn.). Also of interest are spring steel and shape memory polymeric or plastic materials, such as polypropylene, polyethylene, etc.

Rubber and polymeric materials may also be used, particularly for the holdfast or airflow resistor. For example, materials which may be used include: latex, polyethylene, polypropylene, polystyrene, polyvinyl chloride, polyvinylidene chloride, polyvinyl acetate, polyacrylate, styrene-butadiene copolymer, chlorinated polyethylene, polyvinylidene fluoride, ethylene-vinyl acetate copolymer, ethylene-vinyl acetate-vinyl chloride-acrylate copolymer, ethylene-vinyl acetate-acrylate copolymer, ethylene-vinyl acetate-vinyl chloride copolymer, nylon, acrylonitrile-butadiene copolymer, polyacrylonitrile, polyvinyl chloride, polychloroprene, polybutadiene, thermoplastic polyimide, polyacetal, polyphenylene sulfide, polycarbonate, thermoplastic polyurethane, thermoplastic resins, thermosetting resins, natural rubbers, synthetic rubbers (such as a chloroprene rubber, styrene butadiene rubber, nitrile-butadiene rubber, and ethylene-propylene-diene terpolymer copolymer, silicone rubbers, fluoride rubbers, and acrylic rubbers), elastomers (such as a soft urethane, water-blown polyurethane), and thermosetting resins (such as a hard urethane, phenolic resins, and a melamine resins).

Biocompatible materials may be used, particularly for those portions of the device (e.g., the holdfast) which may contact a user. In addition to some of the materials described above, the biocompatible materials may also include a biocompatible polymer and/or elastomer. Suitable biocompatible polymers may include materials such as: a homopolymer and copolymers of vinyl acetate (such as ethylene vinyl acetate copolymer and polyvinylchloride copolymers), a homopolymer and copolymers of acrylates (such as polypropylene, polymethylmethacrylate, polyethylmethacrylate, polymethacrylate, ethylene glycol dimethacrylate, ethylene dimethacrylate and hydroxymethyl methacrylate, and the like), polyvinylpyrrolidone, 2-pyrrolidone, polyacrylonitrile butadiene, polyamides, fluoropolymers (such as polytetrafluoroethylene and polyvinyl fluoride), a homopolymer and copolymers of styrene acrylonitrile, cellulose acetate, a homopolymer and copolymers of acrylonitrile butadiene styrene, polymethylpentene, polysulfones polyimides, polyisobutylene, polymethylstyrene and other similar compounds known to those skilled in the art.

Other materials of interest include any materials that can serve as filters for allergens, pollen, dander, smog, etc. By providing a filter within the device, sinusitis, sleep apnea, snoring, hay fever, allergic rhinitis, and other allergic respiratory conditions may be reduced or prevented. This filter may in fact be part of the airflow resistor or may be a separate component of the device. Any suitable filtering material known to those skilled in the art may be used with the respiratory devices described herein. Such materials include, but are not limited to, activated carbon charcoal filters, hollow-fiber filters, and the like.

In some versions, the respiratory device may comprise a filter that remains in the path of inhalation and/or exhalation during use. In some versions, the filter material remains in the path of both inspiratory and expiratory airflow. This filter material may not appreciably alter resistance to airflow in either direction, or it may alter airflow to substantially the same degree in both directions (inhalation and exhalation). In some versions, the filter comprises a material having a large pore size so that airflow is not significantly inhibited.

The airflow resistor may be oriented in any direction. For example, in some embodiments of the device, the airflow resistor comprises valve flaps that are oriented such that both flaps are in a closed position during inspiration and in an open position during expiration. The respiratory devices may be orientated so that the airflow resistor increases resistance to expiration, and has a relatively lower or negligible resistance to inspiration. However, these devices can be oriented in the opposite direction as well, so that the device offers increased resistance to inspiration and decreased resistance to expiration. Such orientation may be used for a variety of pulmonary, cardiac, inflammatory, neurologic, or other disorders that might benefit from such changes in resistance and its subsequent changes to intrathoracic and airway pressures. This version of the device may be structurally identical to other embodiments described elsewhere in this application. In some versions, the respiratory device is reversible, so that it may be used in either orientation by the user (e.g., to increase the resistance of inspiration relative to expiration in one orientation, or to increase the resistance of expiration relative to inspiration in another orientation). In some versions, the respiratory device is shaped so that the direction of the airflow resistor is immediately evident. For example, the respiratory device may be of a different shape or size on one end, or may include a visual indication. In one version, the respiratory device may be shaped so that it fits securely into a respiratory orifice only in one orientation (e.g., so that the airflow resistor inhibits the expiration more than it inhibits inhalation). For example, a flange or other mechanical stop may be used to insure proper orientation, while simultaneously preventing migration of the device further into the respiratory orifice.

In many embodiments, the device provides some level of resistance to expiration. It may be preferable to have little if any effect on resistance to inspiration, though in some cases, some degree of inspiratory restriction may be beneficial. In some versions of the device, both inspiration and expiration may be inhibited by the airflow resistor.

The device may also be adapted for comfort. Any device placed either in or around the oral cavity or in or around the nose should not be painful, and if possible not very noticeable by the patient. Thus, the holdfast may be shaped to conform to the attachment site in or around the respiratory orifice. In some versions, the holdfast comprises a flexible or shapeable material (e.g., a foam or other soft shape-memory material). In some versions, the entire respiratory device comprises a soft material.

Furthermore, the device may be adapted so that it is more or less visible to others. In some cases, the device may be configured to be placed high enough within the nostrils to make it difficult for others to see. Furthermore, the device may be of any color and/or pattern that help to camouflage it. In other versions, it may be useful to include colors and patterns that stand out, including ones that are fluorescent or otherwise offer increased visibility during the night or other setting where ambient light is reduced.

In some versions, the respiratory device may be "one size fits all", so that it may be used with any patient (or any patient of approximately the same size), despite differences in shapes and sizes of their nose/nostrils, oral cavity, teeth and other relevant anatomic features. In one version, the devices may conform to a range of sizes, for example "small," "medium," and "large" (or any other appropriate range, such as, e.g., a numerical range). Alternatively, the devices may involve a custom fit of the device or devices to the patient.

Custom fitting may improve patient comfort and potentially improve performance by improving the seal between the device and the patient's oral cavity, mouth, nasal cavity and nostrils, for example. In some versions, custom fitting may involve the placement of a device in warm or cold liquid or air with subsequent placement in the patient's nose or mouth. This process is meant to "prime" the materials in the device (e.g., particularly the materials of the holdfast), so that when holdfast is secured to the patient, the device permanently assumes a shape or configuration corresponding to a portion of the patients anatomy.

In some version of the devices described herein, an airflow resistor may fit within a larger structure (such as the passageway) so that some airflow through or around the airflow resistor is always allowed. For example, there might be a constant opening between the airflow resistor and the anchor that secures the airflow filter in communication with the passageway. This may ensure that expiratory and/or inspiratory airflow is never completely occluded. In some versions, the airflow resistor comprises a "hole" or opening. For example, a flap valve may comprise an opening through the flap valve permitting airflow through the flap valve even when the valve is closed.

The device may also create a PEEP effect by differentially changing the resistance to airflow in one direction based on the pressure applied against the device. For example, in some designs, expiratory airflow is subjected to resistance by the airflow resistor (or valve) until a certain threshold pressure differential or level of airflow is achieved; below that threshold, a more complete closure of the airflow resistor occurs (potentially completely occluding airflow through the device). The desired levels of PEEP are on the order of about 0.1 to about 30 cm H2O and more preferably about 1 to about 15 cm H2O pressure. Similarly, the differential resistance may also be triggered in the opposite direction; for example, above a certain threshold of pressure or level of airflow, the airflow resistor (e.g., valve) may open to decrease the resistance due to the airflow resistor, as when a patient coughs, sneezes, or blows his or her nose.

The optimal level of expiratory resistance or PEEP provided by the device may vary from patient to patient. In some versions, adequate expiratory resistance or PEEP is created to offer the desired benefits, but not providing too much expiratory resistance or PEEP so that the patient preferentially begins breathing through the mouth. In some cases, the user may test the device or devices while being monitored by a healthcare provider, a camera, a polysomnograph, or any other device that will help to assess the optimal level of resistance or therapy provided by the subject devices.

The use of an airflow resistor may also alter the inspiratory time:expiratory time ratio (I:E ratio), which is defined as the ratio of inspiratory time to expiratory time. The desired I:E ratio will be between about 3:1 and about 1:10 and more preferably about 1:1.5 to about 1:4 depending on the needs of the individual patient. In some versions, the desired ratio is approximately about 1:3.

In some versions, the device comprises an insertion, adjustment, or removal mechanism. In some cases, this mechanism involves any appropriate rigid or non-rigid positioner that facilitates removal or positioning of the device. Non-rigid positioners include but are not limited to cables, chains, wires, strings, chains, sutures, or the like. Rigid positioners include knobs, handles, projections, tabs, or the like. A user may grasp or otherwise manipulate the positioner to facilitate insertion, re-adjustment, or removal of the device. Furthermore, various applicators or other insertion devices may be used. For example, a tubular applicator holding a respiratory device adapted for insertion into a nasal cavity may be advanced into the nasal respiratory orifice (e.g., nostril) to insert the respiratory device.

In some cases, the device may be oversized. Oversizing the device may reduce resistance in one or more direction of airflow. In some versions, the passageway through the device is oversized. In some versions, an outer portion of the device that contacts the respiratory orifice is oversized. Thus, the respiratory device may exert pressure against the nasal cavity of a user. In patients with obstructive sleep apnea or snoring, for example, increasing the size of the a respiratory device configured to be inserted into one or more nostrils may prevent the more distal tissues of the airway, tongue, and nasopharynx from being sucked in or closed during inspiration. Moreover, airflow through an oversized passageway may assume a less turbulent flow profile, resulting in a decreased propensity for noise production in the case of snoring, for example. Similarly, the respiratory device passageway may be shaped so as to decrease turbulence of airflow. Likewise, the shape and activity of the airflow resistor may be chosen to minimize turbulence and, therefore, sound or vibration.

In some versions, the device is used with an active agent. In some versions, the active agent comprises a drug. An active agent (e.g., a medicament) or other compound can be placed in or on the device to deliver the active agent into the mouth, tongue, hard and soft palates, sinuses, nose, pharynx, vocal cords, larynx, airways, lungs, trachea, bronchi, bronchioles, alveoli, air sacs, or any tissues that are exposed to inspiratory or expiratory airflow. In some cases, the active agent may be embedded or impregnated in the device or components of the device. In some cases the active agent is a coating. An active agent may comprise any compound that is in some way useful or desirable for the patient. For example, the active agent may be any odorant, including: menthol, phenol, eucalyptus, or any agent that provides a fragrance in the inspired air. Alternatively, an active agent may comprise a drug with beneficial effects, such as beneficial vasculature effects. For example, an active agent may comprise a drug that effects the blood vessels (oxymetazoline or any other vasoactive compound), nasopharynx, airways or lungs (albuterol, steroids, or other bronchoconstriction or bronchodilation compounds). An active agent may comprise an antibiotic or a steroid for example. The above list of active agents is not meant to be limiting.

An active agent may be placed in or on any portion of the device. Furthermore, the location of the active agent within the respiratory device may specifically guide the delivery of the active agent. For example, in versions of the respiratory device configured to be placed inside a respiratory cavity, when the holdfast comprises an active agent (e.g., coated, embedded or otherwise part of the holdfast), the drug may be delivered through the mucus membranes of the respiratory cavity. In another example, an active agent may be included as a powder or releasable coating that may be aerosolized and delivered within the respiratory system. Thus, an active agent may be on a surface of the device (e.g., the passageway, holdfast or airflow resistor) or embedded within any surface of the device. A separate drug-containing region may also be included in the device. The addition of an active agent may be of particular interest in treating allergies and sinusitis. Respiratory devices (with or without airflow resistors) may therefore comprise active agents such as menthol or other fragrant compounds.

In some versions of the devices, an airflow resistor is not present. The device may comprise a passageway and a holdfast and may or may not include additional support such as a rim. In some cases, the holdfast may be of adequate strength to support and prevent migration or movement of the device, and to provide adequate radial support to prevent reduction of the passageway of the device during the various phases of the respiratory cycle. In this case, the device props open the nasal or oral cavities to facilitate inspiratory and/or expiratory airflow. This may be helpful in preventing obstructive sleep apnea and snoring since these disorders can be treated, for example, by increasing the size of the nares. This is partly due to the tendency of the nares and nasal cavity to collapse due to negative inspiratory pressures. Thus, preventing these nasal tissues from collapsing may prevent further downstream tissues in the nasopharynx from collapsing. As mentioned earlier, the device may be oversized relative to the size of the nares or nasal cavity in order to reduce resistance and maximize airflow.

The respiratory devices may be manufactured and assembled using any appropriate method. Representative manufacturing methods that may be employed include machining, extruding, stamping, and the like. Assembling methods may include press-fitting, gluing, welding, heat-forming, and the like.

Turning now to the figures, FIG. 1 provides a perspective view of one version of the respiratory device 1 in which the device can fit into the oral cavity of a user. The holdfast 5 comprises grooves 2 and 3 in which the user's teeth and/or gums may preferentially sit, thus securing the device in the oral cavity. Airflow resistor 4 represents any airflow resistor capable of modulating inspiratory and/or expiratory resistance during any or all portions of the respiratory cycle, as described above. The airflow resistor 4 sits within a passageway 6.

Figure 2:
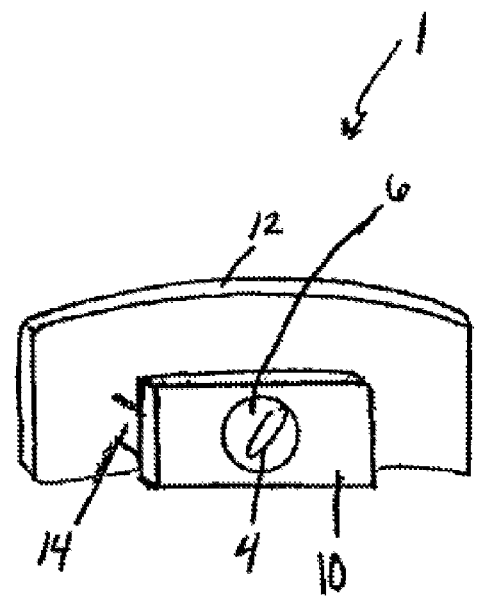
FIG. 2 is a perspective view of another respiratory device adapted for the oral cavity.

FIG. 2 is a perspective view of another embodiment of the respiratory device 1 that may be fitted in an oral cavity. In this embodiment, the patient's teeth and/or gums help to secure the device in place by contacting the holdfast. The holdfast comprises an inner frame 10, and outer frame 12, and a positioner 14. The inner frame 10 is located on the internal portions of the patient's teeth or gums. The outer frame 12 is positioned outside the patient's teeth/gums or outside the patient's lips. The positioner 14 is located between the upper and lower jaws, teeth, and/or gums. An airflow resistor 4 modulates inspiratory and/or expiratory resistance during any or all portions of the respiratory cycle.

Figure 3:
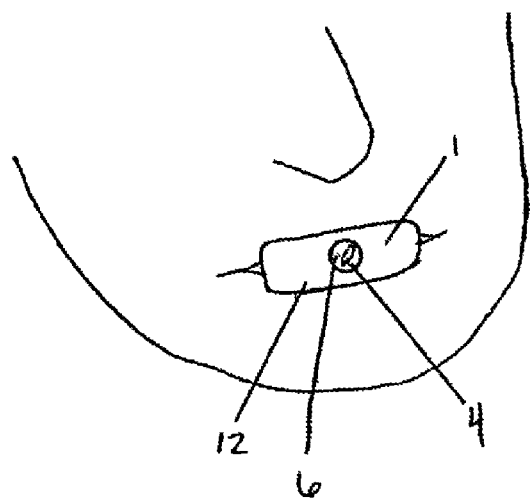
FIG. 3 is a perspective view of the device shown in FIG. 2, where the device is positioned in a patient's oral cavity.

FIG. 3 is a view of the device 1 shown in FIG. 2, where the device is depicted within and protruding from the patient's oral cavity. The outer frame 12 of the holdfast is shown outside of the patient's teeth and gums. The airflow modulator 4 within the passageway 6, modulates inspiratory and/or expiratory resistance during any or all portions of the respiratory cycle through the oral respiratory passageway.

One or more airflow resistors 4 and/or passageways 6 may be used in this (or any, e.g., oral or nasal) respiratory device.

Figure 4:
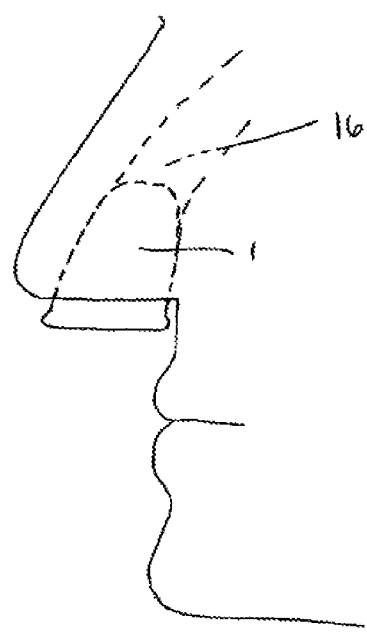
FIG. 4 shows a respiratory device adapted for the nasal cavity.

FIG. 4 is a perspective view of another embodiment of the respiratory device 1 in which the device is removable and may be secured within a patient's nasal cavity 16. In this embodiment, the device protrudes from the nasal opening. The sides of the device comprise a holdfast which is shown fitting snugly within the nasal passage, as well as projecting out from the nasal passage.

FIG. 5 is a perspective view of another version of the respiratory device 1 in which the device is placed completely within the nasal passage 16. The entire respiratory device fits snugly within the nasal passage.

FIG. 6 is a cross-sectional view of a respiratory device 1 similar to those shown in FIGS. 4 and 5. A holdfast 28 comprises the outer surface of the device that contacts the inner portions of the nasal cavity, thus serving to secure the device in place while ideally creating a partial or complete seal. The passageway 6 through which air may flow is surrounded by a rim 30 that provides additional structural support to the device. A rim 30 is not required, particularly if the walls of the passageway (which may be defined by the holdfast 28, for example) provide sufficient support. An airflow resistor 24 is included within the passageway which may modify inspiratory and/or expiratory resistance during any or all portions of the respiratory cycle.

FIGS. 7A and 7B show more detailed views of the operation of airflow resistors shown in FIGS. 4 and 5. These cross-sectional views illustrate the holdfast 28, the optional rim 30, the passageway 6, and the airflow resistor, shown as a valve 32. The rim 30 separates the holdfast 28 and the valve 32, frames the valve 32, and provides overall structural support to the entire device. In FIG. 7A, the valve 32 is shown in the open position, providing less resistance to airflow. In FIG. 7B, valve 32 is shown in the closed position, providing more resistance to airflow, because the cross-sectional area of the passageway 6 has been constricted by the closing of the valve.

FIGS. 8A and 8B show perspective views of an airflow resistor that could be used, for example with any of the devices described in FIGS. 1-5. In these figures, a rim 30 is shown. The rim may be part of the holdfast which positions and secures the device within a respiratory passageway; alternatively, additional material (e.g., compliant material) may be attached to the rim to form the holdfast. In FIGS. 8A and 8B, the rim provides support to the airflow resistor 24. The airflow resistor is shown here as a flap valve mechanism that comprises a flap 36 that pivots around a joint 38 and is connected to a fixed element 40. Fixed element 40 is attached to the inner region of the passageway 6, which is defined in this figure by the rim 30. In some versions, the flap valve and the inner surface of the passageway 6 (e.g., the rim 30) may constitute a single piece. Alternatively, the flap 36, joint 38, and fixed element 40 may be fabricated as a single piece, in which case joint 38 may be a hinge. Thus, joint 38 may be a pinned hinge or a non-pinned hinge joint. Alternatively, rim 30, flap 36, joint 38, and fixed element 40 may all be created as a single piece or material. Thus, flap 36 is able to pivot in relation to fixed element 40 depending on the direction of the patient's airflow and the desired level of resistance to airflow. FIG. 8A shows the airflow resistor with flap 36 in a closed position during expiration, thus providing increased resistance. In some versions, the flap portion of the airflow resistor closes completely, as shown. In these versions, the edges of the flap 36 may close off the entire passageway (as shown), or may only occlude a portion of the passageway. FIG. 8B shows the airflow resistor with flap 36 in the open position (e.g., during inspiration), thus providing decreased resistance. Flap 36 may define a hole, or may have other openings (which may stay open during all or part of the respiratory cycle) to help modulate the degree of inspiratory and expiratory resistance. The flap 36 may return to a preferred opened or closed position. For example, a shape memory material, a spring (such as a torsion spring), or the holdfast may apply force to flap 36 to return it to a closed position. For example, the use of foam or urethane surrounding the airflow resistor may provide such force as to close flap 36 in the absence of adequate airflow. Bi-leaflet versions of the airflow resistor are also contemplated and will have similar function. These bi-leaflet versions may involve multiple sets of flaps 36, joints 38, and fixed elements 40, etc.

FIGS. 9A and 9B show a perspective view of another embodiment of an airflow resistor that could be used in any of the respiratory devices described herein. The inner surface of the passageway shown includes a rim 30 that supports the airflow resistor. This airflow resistor 24 is also shown as a valve mechanism. Moveable elements 42a and/or 42b (flaps) are attached to one another or are constructed from a single piece. Moveable elements 42a and 42b are attached to the inner surface of the passageway (shown as a rim 30) at attachment points 44a and 44b, and these attachment points may allow the valve to pivot around a hinge 43 in response to direction and amplitude of airflow. In one version, attachment points 44a and 44b are formed directly into the rim 30 or holdfast 28 during the manufacturing (e.g., casting) process. In one version, the hinge is statically attached to an inner region of the passageway, and the flaps 42a and 42b are movably (or flexibly) attached to the hinge. FIG. 9A shows this airflow resistor when the resistance is high (e.g., the flap valve is mostly closed), as during expiration, and FIG. 9B shows the airflow resistor when the resistance is low (e.g., the flap valve is mostly open), as during inspiration.

FIG. 10 shows a perspective view of another embodiment of an airflow resistor that is similar in structure and function to the device shown in FIGS. 9A and 9B. However, the airflow resistor shown has an internal opening 45 that is located approximately where moveable elements 42a and 42b pivot relative to one another. The addition of internal opening 45 modulates airflow (e.g., inspiratory or expiratory airflow) by altering the level of resistance. Addition of this opening reduces the resistance in one direction (e.g., expiratory resistance, when the flap valve is "closed") more than resistance in the opposite direction (e.g., inspiratory resistance, when the flap valve is "open").

FIG. 11 shows a perspective view of another embodiment of an airflow resistor that is similar in structure and function to the device shown in FIGS. 9A and 9B. Peripheral openings 46a and 46b are placed completely within, or on the periphery of the moveable elements 42a and 42b. These peripheral openings 46a and 46b also modulate inspiratory and/or expiratory resistance. The addition of peripheral openings 46a and 46b helps modulate inspiratory and expiratory airflow by altering the level of resistance. Addition of these peripheral openings also reduce the resistance in one direction (e.g., expiratory resistance, when the flap valve is "closed") more than resistance in the opposite direction (e.g., inspiratory resistance, when the flap valve is "open").

Figure 12A:
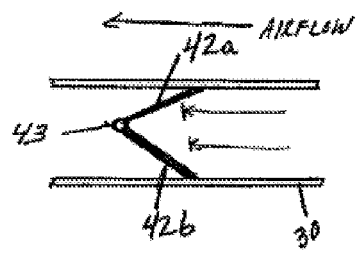
FIGS. 12A and 12B show cross-sectional views of the respiratory devices shown in FIGS. 9A, 9B, 10, and 11 during exhalation (FIG. 12A) and inhalation (FIG. 12B), respectively.
Figure 12B:
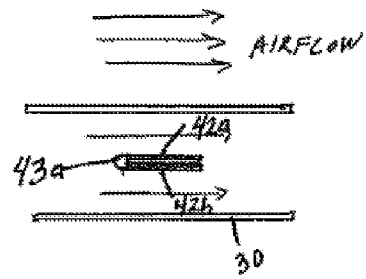

FIGS. 12A and 12B show more detailed views of the operation of the valve mechanisms as described in FIGS. 9A, 9B, 10, and 11. In this figure, we assume that the airflow resistor is oriented so that the airflow resistor increases resistance during expiration relative to inhalation (e.g., the lungs are located to the right in FIGS. 12A, 12B and 12C).

Figure 12C:
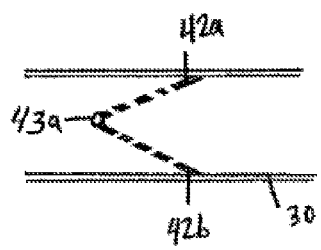
FIG. 12C shows a cross-sectional view of a variation of the respiratory device during exhalation.

Moveable elements 42a and 42b are coupled to each other via hinge 43. FIG. 12A demonstrates the valve mechanism during expiration, in which moveable elements 42a and 42b are in a closed position due to the expiratory airflow in the direction from the lungs to the external environment. FIG. 12B demonstrates the valve mechanism during inspiration, in which moveable elements 42a and 42b are in an open position due to the inspiratory airflow in the direction from the external environment to the lungs. FIG. 12C demonstrates a modification of the valve mechanism shown in FIGS. 12A and 12B in which there are one or more apertures within or on the periphery of the moveable elements that reduce resistance to expiratory airflow, further increasing the rate of expiratory airflow. All of these valve mechanisms and configurations can be placed in the opposite orientation so that inspiratory airflow leads to valve closure and expiration leads to valve opening.

Moveable elements (flaps) 42a and 42b of the airflow resistor may be made of any appropriate material. In particular, materials which have sufficient stiffness to withstand the forces applied by the respiratory process. Furthermore, durable materials (e.g., which may withstand the moisture, etc. of the respiratory passage) may also be desirable. In some versions, the devices are disposable, and thus durability may be less critical. Furthermore, the moveable elements 42a and 42b may also be made from porous materials or filters, etc. that do not overly restrict or resist airflow but at the same time can remove debris, pollen, allergens, and infectious agents for example.

Figure 13A:
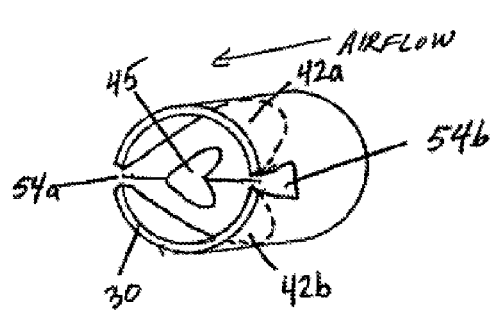
FIGS. 13A and 13B are perspective views of a respiratory device having an airflow resistor where the airflow resistor is shown during exhalation (FIG. 13A) and inhalation (FIG. 13B), respectively.
Figure 13B:
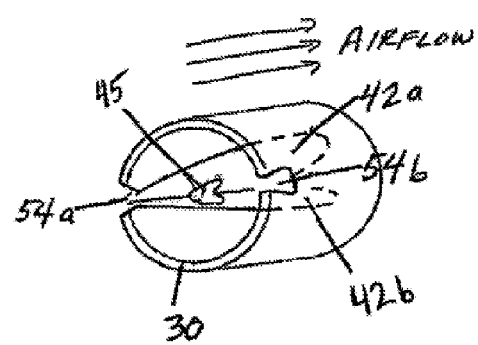

FIGS. 13A and 13B show perspective views of another airflow resistor that could be used in any of the devices described herein. FIG. 13A shows the airflow resistor (a flap valve) in a closed position, as might be seen during expiration, resulting in increased resistance to airflow. FIG. 13B shows the airflow resistor in an open position, as might be seen during inspiration, resulting in a decreased resistance to airflow relative to the closed position. Because of the small profile of the retracted flap valves, the resistance added by the airflow resistor when the airflow resistor is "open" may be negligible. Moveable elements 42a and 42b are attached to each other or are a single piece. Moveable elements 42a and 42b are attached to the walls of the passageway (in this example, defined by a rim 30), to the rim 30, or to the holdfast 28 by a securing element 54a and 54b which uses a tab, adhesives, press fit, external pressure (as from a holdfast 28) or any way known to those skilled in the art. Internal opening 45 is located centrally, decreasing the resistance to expiratory airflow (in the "closed" state), although peripheral locations are also contemplated. In some versions, the size and number of openings in the valves may determine the resistance of the airflow resistor. Thus, the size and number of openings may be selected in order to determine the I:E ratio.

Figure 14:
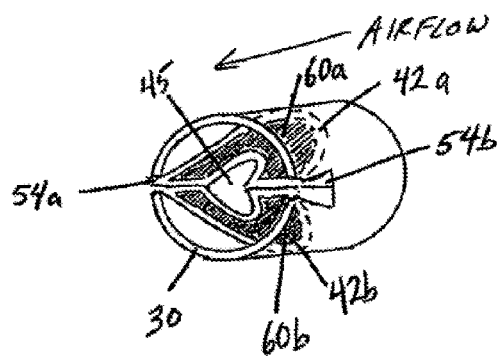
FIG. 14 is a perspective view of a respiratory device having an airflow resistor where the airflow resistor is shown during exhalation.

FIG. 14 provides a perspective view of another embodiment of an airflow resistor that is similar in structure and function to the airflow resistor shown in FIGS. 13A and 13B. In FIG. 14, the movable elements further comprise a reinforcement support 60a and 60b that is located partially or completely covering the moveable elements 42a and 42b. The reinforcement support provides additional structure and/or support to these moveable elements. Furthermore, reinforcement support 60a and 60b may also promote a more reliable seal and may standardize the movements of moveable elements 42a and 42b while reducing the likelihood that moveable elements will invert, buckle in the direction of airflow, or otherwise fail, especially when exposed to high pressures and airflow as might be seen during coughing. The addition of reinforcement support 60a and 60b also dampens any whistling or other sounds during inspiration or expiration. Moveable element 42a and reinforcement support 60a and moveable element 42b and reinforcement support 60b may be a single unit (or each "flap" may be a single unit). Alternatively, both moveable elements 42a and 42b and both reinforcement support 60a and 60b may be a single unit. A central opening 45 is also shown in the figure.

Figure 15A:
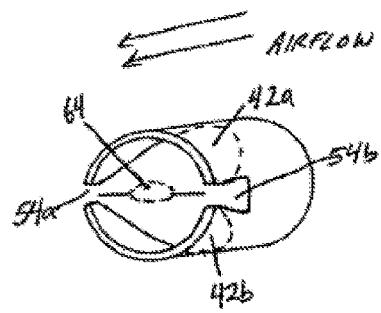
FIGS. 15A, 15B, and 15C are perspective views of a respiratory device having an airflow resistor.
Figure 15B:
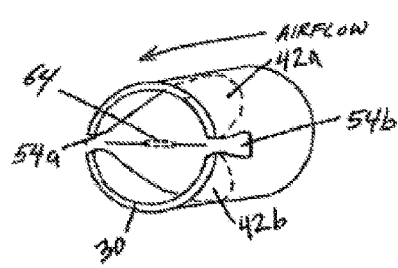
Figure 15C:
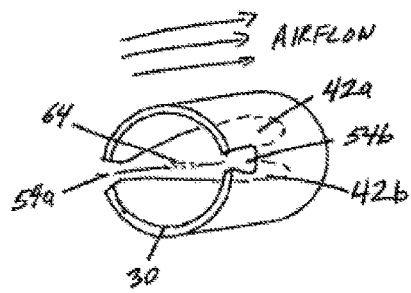

FIGS. 15A-15C show perspective views of another embodiment of an airflow resistor that may be used in any of the devices described herein. The airflow resistor is similar to that shown in FIGS. 13A and 13B with the exception that internal opening 45 is replaced by another airflow resistor 64 (a "nested airflow resistor"). This nested airflow resistor 64 automatically closes when the flow through the valve (or the pressure differential across the valve) falls below a predetermined level. This allows the airflow resistor (with the nested airflow resistor region) to provide positive end expiratory pressure (PEEP). In FIG. 15A, the airflow resistor is shown during exhalation, and the moveable elements 42a and 42b of the airflow resistor are in the closed position. The nested portion of the airflow resistor 64 is open so long as the pressure differential across the airflow resistor and/or airflow is above a certain level. Thus, this figure demonstrates the beginning of expiration, when airflow in the passageway and pressure differential are largest. In FIG. 15B, the same airflow resistor is again shown during expiration, and moveable elements 42a and 42b of the airflow resistor are still in the closed position. However, the nested airflow resistor region 64 now assumes a closed position, since the pressure differential across the airflow resistor and airflow through the passageway is no longer above the threshold value. This scenario may correspond to the later stages of exhalation, when airflow and pressure differential are decreasing or are lower. Thus, at the end of exhalation, PEEP has been created. For example, the nested airflow resistor 64 may be set to close whenever air pressure in the respiratory orifice coming from the lungs is less than 5.0 cm H20. FIG. 15C shows the device during inhalation, in which moveable elements 42a and 42b of the airflow resistor are in the open positions, allowing inhalatory airflow with minimal resistance to said airflow.

Figure 16A:
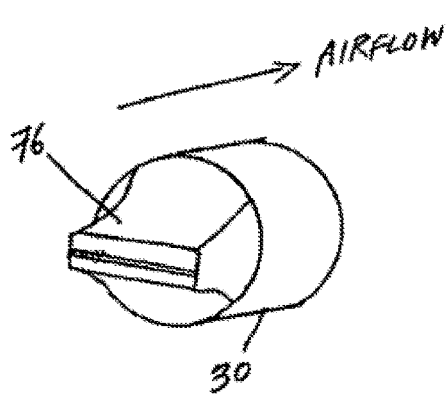
FIGS. 16A and 16B are perspective views of a respiratory device having an airflow resistor where the airflow resistor is shown during exhalation (FIG. 16A) and inhalation (FIG. 16B), respectively
Figure 16B:
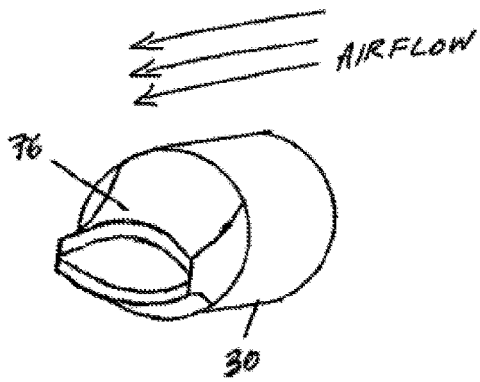

FIGS. 16A and 16B show perspective views of another embodiment of an airflow resistor that may be used in any of the devices described herein. FIG. 16A shows a hingeless valve 76 in a closed position during exhalation, in which there is increased resistance to airflow. FIG. 16B shows a hingeless valve 76 in an open position during inspiration, in which there is decreased resistance to airflow. The hingeless valve 76 may also comprise one or more holes within its structure to allow airflow in either direction at various stages of the respiratory cycle. For example, despite being in a closed position, the hingeless valve 76 would still allow some level of expiratory airflow. Alternatively, the hingeless valve 76 might never close completely. Even in a closed state, its flaps may never completely block all airflow.

FIGS. 17A and 17B show perspective views of another embodiment of an airflow resistor that could be used in any of the devices described herein. The membrane-type airflow resistor show in FIGS. 17A and 17B comprises a membrane 80 (that may or may not be floppy) that is attached by a connector 82 to the body of the airflow resistor. During exhalation, shown in FIG. 17A, the membrane 80 seats itself against a rim 30 and/or an apposition support 84 which may project from the sides of the passageway (e.g., from the rim 30) to support the membrane 80 during exhalation. FIG. 17B shows the situation during inhalation, when the membrane 80 in a deflected position, thereby decreasing resistance to inspiratory airflow, and increasing airflow through the airflow resistor. Membrane 80 may have an opening 86 (or openings) which remain open during both inspiration and exhalation. In some versions of the airflow resistor, membrane 80 does not have an opening. In still other versions, there are several openings within membrane 80.

FIGS. 18A and 18B show cross-sectional views of another embodiment of an airflow resistor that could be used in any of the devices described herein. FIG. 18A shows the airflow resistor during inspiration, during which deformable member 90 is unfurled leading to decreased resistance and increased airflow. FIG. 18B shows the airflow resistor during expiration, during which deformable member 90 assumes an orientation or folding configuration that leads to increased resistance and decreased airflow. Deformable member 90 may have a preferred default position (a tendency to default to a preferred orientation in the absence of external influences or pressures) that may allow such an airflow resistor to offer a PEEP effect.

FIGS. 19A and 19B show cross-sectional views of another embodiment of an airflow resistor that could be used in any of the devices described herein. This is a stopper-type airflow resistor. FIG. 19A shows the airflow resistor on exhalation with little to no airflow and minimal pressure differential across the valve. FIG. 19B shows the device during more robust exhalation, characterized by increased airflow and increased pressure differential across the valve. Stopper 92 is connected to return mechanism 94. Stopper 92 may also have an opening within it to allow airflow at all times or at specific parts of the respiratory cycle (e.g., another, nested, airflow resistor, such as one allowing airflow during inhalation, but not exhalation), thereby providing fluid communication between the airways and the external environment. Alternatively, stopper 92 may have a valve portion that is open during inhalation and closed during exhalation, or vice versa. In FIG. 19A, the airflow from right to left is insufficient to overcome the spring force provided by return mechanism 94, and stopper 92 seals against seating supports 96a and 96b. In FIG. 19B, the airflow from right to left is sufficient to overcome the spring force provided by return mechanism 94, and stopper 92 is displaced leftward and thus expiratory airflow is allowed. The mechanism described in FIGS. 19A and 19B is one way in which PEEP can be created by the device.

FIG. 20 is a perspective view of another embodiment of the respiratory device where the device is removable and may be placed in communication with the nasal cavity. In FIG. 20, a holdfast 28 is located between the patient's nose and the airflow resistor in the device 1, providing a partial or complete seal, anchoring the device, and providing comfort for the patient. The holdfast 28 has a cross section that is roughly circular and capable of fitting within a patient's nostrils.

FIG. 21 is a perspective view of another embodiment of a respiratory device where the device is removable and may be placed within the nasal opening. This device shows a holdfast 28 having an approximately oval cross-section. Many such cross-sectional shapes are possible to optimize placement, anchoring, sealing, and comfort, including a variety of conical or asymmetric shapes designed to fit within a patient's nasal openings. In some cases, the rim 30 and/or any airflow resistor 4 may also assume any desired cross sectional shape, including that of an oval or any other non-circular orientation. In some embodiments, the holdfast 28 will be shapeable, deformable, or adjustable by the patient either before, after, or during placement of the device. Alternatively, the device can be customizable to fit individual patients through the use of imaging modalities including MRI, CT, x-ray, or direct vision, or through the use of molding techniques that are common in dentistry and other fields.

Figure 22:
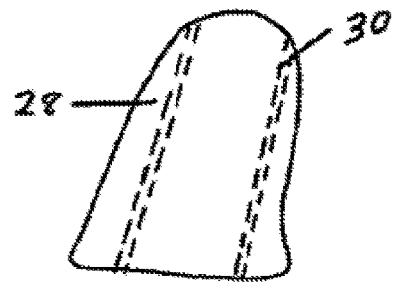
FIG. 22 is a cross-sectional view of a respiratory device where the device is removable and adapted for the nasal cavity.

FIG. 22 is a cross-sectional view of an embodiment of a respiratory device where the device is removable and may be secured in fluid communication with a nasal cavity. In this version, the device does not contain any moveable components that alter airflow. The device comprises a holdfast 28 and rim 30 that lends the device support. The device may be oversized to decrease resistance and increase airflow in one or more directions. In some cases, a drug (with either an active or inactive ingredient) may be embedded in or located on any of the device's components, for example, the rim 30. It is appreciated that in some cases, there may be no rim 30, so long as structural support is provided by another component of the device, e.g., the holdfast. In this case, the drug may be loaded or coated on the holdfast or within the passageway.

Figure 23:
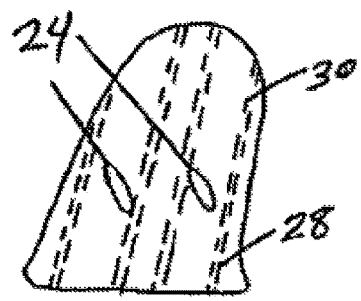
FIG. 23 is a cross-sectional view of a respiratory device where the device is removable and adapted for the nasal cavity.

FIG. 23 shows a cross-sectional view of another embodiment of a respiratory device where the device is removable and may be secured in communication with a nasal cavity. In this figure, there are two airflow passageways. Each passageway is shown with an airflow resistor 24 therein. The holdfast 28 surrounds both passageways, and each passageway includes an (optional) rim 30. Each of the flow resistors 24 may increase or decrease resistance to airflow independently and may work simultaneously or at different times during the respiratory cycle. For example, in some cases, during inhalation, one of the airflow resistors 24 may decrease resistance to airflow while the second airflow resistor 24 increases resistance to airflow. On exhalation, the first airflow resistor 24 may increase resistance to airflow while the second airflow resistor 24 decreases resistance to airflow. In other words, inspiratory airflow may proceed through one location, and expiratory airflow may proceed through a second location within the same device.

Figure 24:
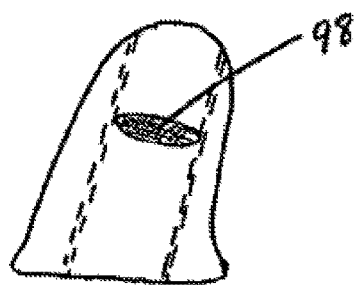
FIG. 24 is a cross-sectional view of a respiratory device where the device is removable and adapted for the nasal cavity.

FIG. 24 is a cross-sectional view of another embodiment of the respiratory device where the device is removable and may be secured in communication with a nasal cavity. The device is shown with a fixed filter 98 that is located in the path of the airflow as it traverses the device. The fixed filter 98 may help clear the airflow of any solid or liquid particles, debris, odors, allergens, pollen, and/or infectious agents. This filter 98 may remain roughly fixed in place during all parts of the respiratory cycle though some degree of movement may be permitted. A drug may be placed within or on the surface of one or more components of the device to provide additional benefit to the patient. The addition of fixed filter 98 may not lead to increased resistance in either direction, unless such a design is desired. The fixed filter 98 can be created from any number of filter materials that are known to those skilled in the art. This fixed filter 98 may be used in any of the respiratory devices herein, in addition to, or as an alternative to, an airflow resistor 4.

Figure 25:
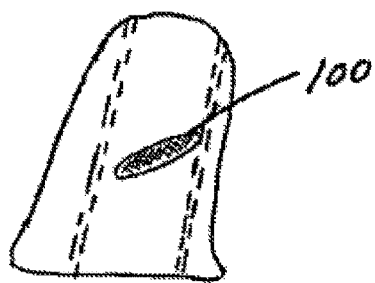
FIG. 25 is a cross-sectional view of a respiratory device where the device is removable and adapted for the nasal cavity.

FIG. 25 is a cross-sectional view of another embodiment of the respiratory device, where the device is removable and may be secured in communication with a nasal cavity. The respiratory device of FIG. 25 comprises a moveable cleansing filter 100 that is shown located within the device, and which may help to clear the airflow of solid or liquid particles, debris, odors, allergens, pollen, and/or infectious agents. In some versions, the filter may be configured to move so that it filters only during inhalation (or exhalation), or may move out of the way during periods of extremely large airflow (or air pressure) in the airflow passageway (e.g., during coughing, nose blowing, sneezing).

Figure 26A:
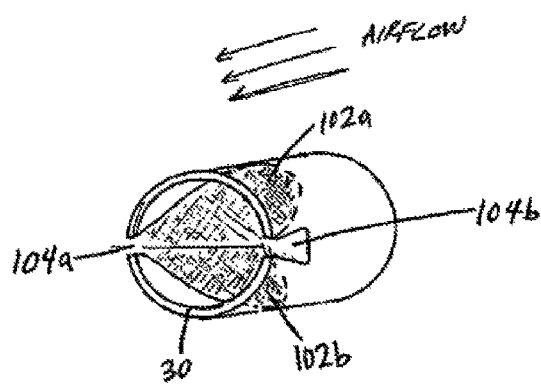
FIGS. 26A and 26B are perspective views of a respiratory device having a moveable air filter where the moveable air filter is shown during inhalation (FIG. 26A) and exhalation (FIG. 26B), respectively.
Figure 26B:
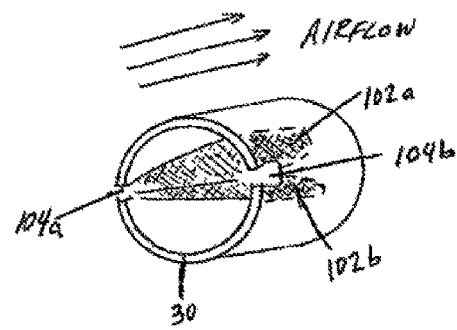

FIGS. 26A and 26B are perspective views of one version of a moveable cleansing filter where the moveable cleansing filter is shown during inhalation and exhalation respectively. A movable cleansing filter may be a movable filter, scrubber, or any other device capable of removing (particularly selectively removing) any solid or liquid particles, debris, odors, allergens, pollen, and/or infectious agents. This moveable cleansing filter may be used in any of the respiratory devices herein, in addition to, or as an alternative to, an airflow resistor 4. FIG. 26A shows the moveable cleansing filter (shown as movable filters) during inspiration (during which airflow travels from right to left in the figure) leading to displacement of moveable filter elements 102a and 102b away from one another. FIG. 26B shows the moveable cleansing filter during expiration (during which airflow travels from left to right in the figure) leading to displacement of moveable filter elements 102a and 102b towards one another. Thus, on inspiration, airflow passes through the moveable filter elements 102a and 102b and the air may be cleansed of the relevant substances. On expiration, airflow passes both through and around moveable filter elements 102a and 102b. The addition of moveable filter elements 102a and 102b ideally does not lead to increased resistance in either direction, unless such a design is desired. The moveable filter elements 102a and 102b can be created from any number of filter materials that are known to those skilled in the art. One or more openings or apertures may be placed within the moveable filter elements 102a and 102b to alter inspiratory or expiratory resistances.

Figure 27:
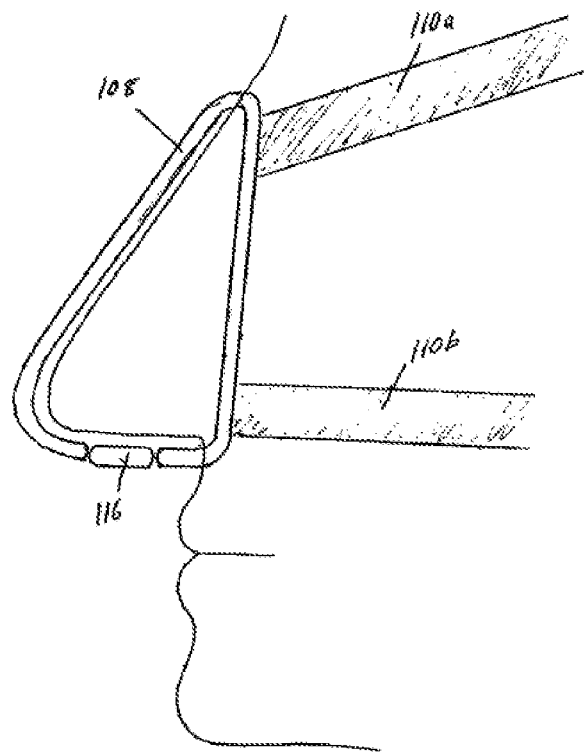
FIG. 27 is a perspective view of another respiratory device where the device is removable and adapted for the nasal cavity.

FIG. 27 is a three dimensional view of another embodiment of the subject devices where the device is removable and secured in communication with both nasal cavities. Nasal mask 108 is positioned securely against the nose and face in order to minimize or eliminate the possibility of air leak around the periphery of the device. The device includes a holdfast comprising straps 110a and 110b (that facilitate the secure positioning) and a nasal mask 108 that is secured against the face by the straps. The mask's airflow resistor 116 modulates inspiratory and/or expiratory resistance during any or all portions of the respiratory cycle. There is at least one airflow resistor 116 located on the device, though two or more airflow resistors 116 may be used (e.g., one placed in proximity to each nostril).

Figure 28:
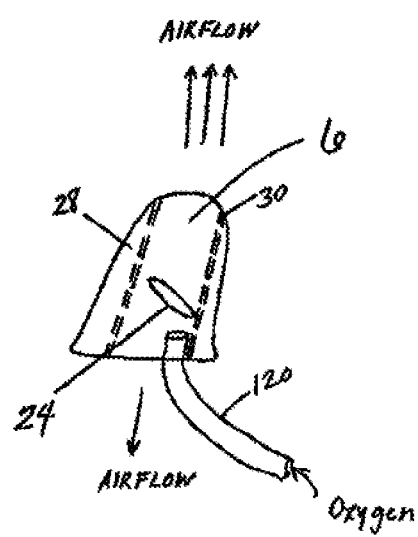
FIG. 28 shows a cross-sectional view of another respiratory device where the device is removable and adapted for the nasal cavity.
Figure 29:
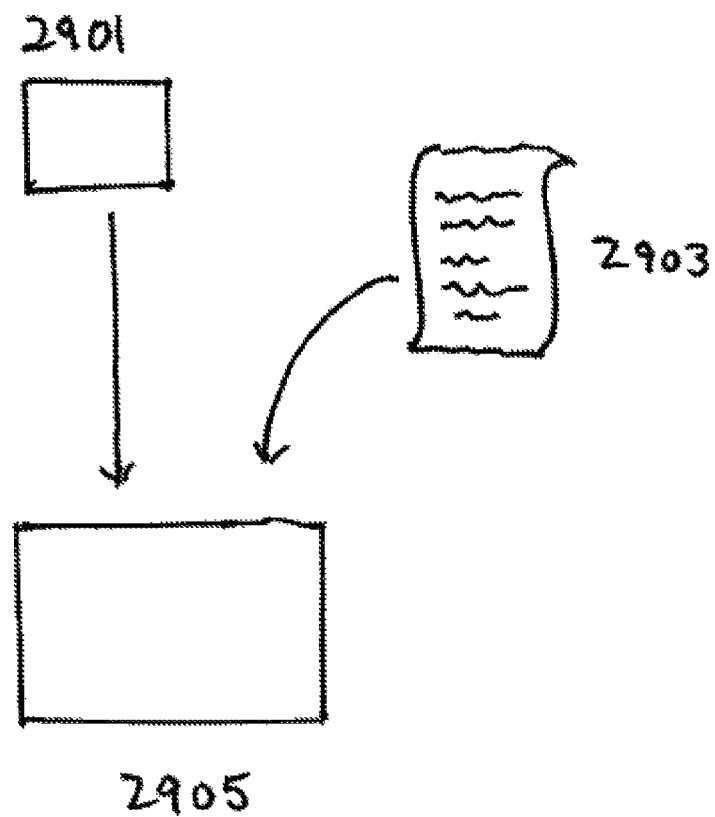
FIG. 29 shows a schematic view of a kit including a respiratory device in packaging and instructions for using the respiratory device.

FIG. 28 is a cross-sectional view of another embodiment of the respiratory device, where the device is removable and may be secured in communication with a nasal cavity. In FIG. 28, a respiratory device further comprises a respiratory gas supply. A respiratory gas inlet 120 is shown attached to the respiratory device, providing gas, such as pure oxygen or mixed oxygen to the passageway. An airflow resistor 24 is included within the passageway which may modify inspiratory and/or expiratory resistance during any or all portions of the respiratory cycle. In some versions of the device, the airflow resistor 24 during exhalation may feature a flap mechanism in which the flap partially or completely occludes respiratory gas inlet 120, thereby only providing release of gas when the patient is inhaling and the flow resistor 24 is therefore open to some degree. The device that provides the respiratory gas may be permanently or non-permanently fixed, attached, or otherwise coupled to the holdfast, rim, or airflow resistor via a press fit, adhesive, or in some other fashion. In some cases, the respiratory gas supply may be an off-the-shelf device that that provides respiratory gas, as is currently available from multiple manufacturers.

The aforementioned devices and methods of using them may provide a first airflow resistance to airflow from proximal airways to distal airways (inhalation) and a second flow resistance to airflow from distal airways to proximal airways (expiration). In some of the respiratory devices described herein, when expiratory airflow and/or expiratory airway pressures fall below a threshold (one that is too low to keep an airflow resistor mechanism open), expiration airflow will be stopped, leading to PEEP. As a result, normal inspiration, normal expiration, and PEEP are accommodated while offering potential benefits to the patient, including clinical benefits.

Uses of the Respiratory Devices

The respiratory devices and methods described herein may be used for a variety of therapeutic and non-therapeutic purposes. A description of some of these uses is given below. The respiratory devices and methods described herein may be used in other ways as well, and these examples are not to be considered exhaustive.

Generally, the respiratory devices described herein may improve the respiratory and cardiovascular function of a person in need thereof (e.g., a patient). Thus, these respiratory devices may be used therapeutically, for example, to cure, treat or ameliorate the symptoms of a variety of medical disease states. Furthermore, the respiratory devices may be useful in generally improving the health and well-being of any person.

Disease states which may be treated by the devices and methods described herein include but are not limited to: heart failure (right-sided and/or left-sided), COPD, pulmonary edema, sleep apnea (obstructive and/or central), sleep-disordered breathing, Cheyne-Stokes respiration, insomnia, snoring and other sleep disorders, asthma, bronchomalacia, acute lung injury, ARDS, cystic fibrosis, hypoxemic respiratory failure, gastroesophageal reflux disease, hiatal hernia, heartburn, hypertension, myocardial infarction, arrhythmia, cardiomyopathy, cardiac valve disease (either stenosis or regurgitation of the mitral, aortic, tricuspid, or pulmonic valves), stroke, transient ischemic attack, increased cerebral pressure, a variety of inflammatory diseases, and degenerative neurologic conditions. Moreover, the devices be beneficial for patients being weaned off mechanical ventilation, as well as post-operative patients.

The increased pressure within the airways may reduce the amount and frequency of pulmonary edema, a common consequence of heart failure. Afterload and preload on the heart may also be affected; for example, afterload and preload may be decreased in patients with heart failure. Filling pressures may be increased or, more likely, decreased. Decreasing filling pressure may potentially benefit patients with failing hearts. Gas exchange may improve in many cases, leading to increases in pO2 and decreases in pCO2. In some cases, the level of pCO2 may actually increase or become more stable and less likely to fluctuate. This increase in the stability of pCO2 levels may lead to profound benefits in patients with central sleep apnea and in patients with Cheyne-Stokes breathing, for example.

Any location within the body that is exposed to respiratory airflow (including but not limited to the upper airway, trachea, bronchi, nasopharynx, oropharynx, nasal cavity, oral cavity, vocal cords, larynx, tonsils and related structures, back of the tongue, sinuses, and turbinates) may benefit from the increased airway pressure and increased duration of expiratory airflow. In some cases, there will be a reduction in swelling and edema in these locations, leading to increased diameters of the airways and conduits in which the airflow passes. This leads to less of a tendency for these structures to collapse upon inhalation. Moreover, these structures may be less prone to create noise on inspiration or expiration, thereby reducing the quantity and/or quality of snoring. Put another way, the reduction of edema in the airways may make it less likely that these structures will collapse and may reduce the volume and frequency of snoring, apnea, or hypopnea. Furthermore, reduction in swelling and edema and improved lymphatic flow due to these positive pressures may reduce nasal congestion, inflammation, and sinusitis for example.

The respiratory device may also increase lung compliance. For example, lung compliance may increase partly if fluid which might otherwise be in the lung and alveoli is driven away by the increased airway pressure. This increased lung compliance may make it easier to breathe and may require less effort and force on the part of the patient to displace the diaphragm a certain distance to achieve a certain tidal volume. Moreover, increased lung compliance may decrease the pressure differential between the alveoli and mouth. As this pressure differential decreases, it becomes less likely that an inhalation attempt will induce a collapse of the upper airway. Thus, an increase in lung compliance may herald a reduction in the frequency or severity of obstructive sleep apnea or hypopnea episodes. Similarly, snoring frequency and severity (volume) may be reduced for similar reasons.

The respiratory device may also improve ejection fraction. This effect may be mediated via increases in intra-thoracic pressure and alterations in transmural pressures and the beneficial effects on preload and afterload on the failing heart. In addition to left-sided benefits to the heart, there may also be benefits afforded to the right side of the heart. Improving ejection fraction with the respiratory devices described herein may result in positive short- and long-term changes to the energetics and biologic properties of the heart tissue. Some of these positive changes may mimic the positive remodeling changes seen in hearts treated with various complicated cardiac support devices such as those developed by Acorn Cardiovascular (St. Paul, Minn.) and Paracor Medical (Sunnyvale, Calif.). These expiratory resistors use the patient's own intra-thoracic pressure to "support" the patient's heart. Moreover, because the support potentially provided by the respiratory devices described herein is not limited to just the ventricle, it may support the atria, which can also be severely affected by heart failure and other cardiac or pulmonary diseases. There may be reductions in left ventricular and left atrial sizes, both in the shorter and longer term. Furthermore, cardiac sympathetic activation may be reduced, and cardiac output may be increased or decreased depending on the nature of the resistance provided.

There are a variety of other beneficial effects of enhanced expiratory resistance and increases in intra-thoracic pressure that may be achieved with the respiratory devices described herein. Examples include decreased heart rate and blood pressure. There may be a reduction in the number of arrhythmias, including but not limited to atrial/supraventricular and ventricular fibrillation, atrial/supraventricular and ventricular tachycardias, heart block, and other common arrhythmias. Thus, the respiratory devices described herein may also reduce the incidence of sudden cardiac death and other cardiac disorders. Furthermore, coronary perfusion may be expected to increase. Further, expiratory resistance and increased intra-thoracic pressures may lead to improvements in gastroesophageal reflux disease (i.e. heartburn), gastritis, Barrett's esophagus, esophageal cancer, hiatal hernia, and other causes of diaphragmatic hernia. This effect may be mediated by the compression of the esophagus located within the thorax due to the increased intra-thoracic pressures. As a result, food and other stomach contents may no longer be able to reflux superiorly into the esophagus, which is otherwise common when patients are lying down. Furthermore, hernias (primarily hiatal) may be reduced and pushed back into the abdomen by the increased intra-thoracic pressure. The use of these respiratory devices may have beneficial effects on other gastroenterologic conditions beyond those already described.

Cardiac valve disease, including but not limited to mitral, tricuspid, pulmonic and aortic regurgitation, and mitral, tricuspid, pulmonic and aortic stenosis may also benefit from the respiratory devices described herein. In particular, the respiratory device may affect mitral regurgitation and may help prevent further annular dilatation (a byproduct of heart failure and generalized heart dilation).

Use of the respiratory devices described herein will result in a reduction in respiratory rate, which may be very helpful in diseases such as COPD, asthma, hyperventilation, and anxiety disorders including panic attacks, among others. The ratio of inspiratory time to expiratory time (I:E ratio) may be decreased with the device. Tidal volumes may increase as well. For example, in COPD, the increased resistance may facilitate improved expiratory function. This may also allow the patient to benefit from larger tidal volumes and increased minute ventilation. In embodiments in which the respiratory device creates PEEP (positive end expiratory pressure), the amount of PEEP (or resistance generated by the device) may overcome some, or all, of the intrinsic PEEP that is common in patients with COPD. In patients with COPD or other pulmonary disorders, gas exchange may improve. In this case, gas exchange refers to the removal of CO2 from the body and addition of O2 into the blood stream from inspired air. Thus, pO2 may increase and pCO2 may decrease, particularly in patients with COPD, but more generally in all patients treated with the device. Moreover, oxygen saturation may increase, reflecting an increase of oxygen binding to hemoglobin.

Other benefits offered by the respiratory device may include a reduction in diaphragm fatigue and improved efficiency of the accessory muscles of inspiration. This may make breathing significantly easier in patients with pulmonary disease, and more specifically COPD and cystic fibrosis.

As previously mentioned, the respiratory devices described herein may decrease respiratory rate. It has been shown that slowed breathing techniques can lead to a reduction in blood pressure. Thus, the device may reduce blood pressure in a patient, including patients with hypertension (systemic and pulmonary). The reduction in blood pressure may be systolic and/or diastolic. Reductions in blood pressure may be on the order of 1-70 mm Hg systolic or diastolic. This may bring the patient to normal (<140/80 mm Hg) or near normal (<160/100 mm Hg) levels. In patients who are being treated for hypertension, the device could be used as an adjunctive therapy to drugs or as a stand-alone therapy in some patients. In some versions, a respiratory device as described herein may be used for short periods (minutes, hours, or longer) over a span of days to weeks to months to offer longer term benefits for weeks or months after the cessation of therapy. Treatments may last 15 seconds to 24 hours and may be repeated over a regular or irregular interval, for example, on the order of hours to days. The devices may be worn at night or day, while awake or during sleep, to slow respiratory rate. A reduction in blood pressure and/or heart rate may be seen while the device is in place, or after the device has been removed. This may be due to hormonal influences whose effects last longer than the period in which the device is in place. More specifically, the device may work though either a sympathetic or parasympathetic pathway.

Expiratory resistance may also prolong expiratory time, which may reduce the respiratory rate. Thus, the devices described herein may be used to reduce respiratory rate. This may have benefits in treating insomnia, since it may promote a sense of relaxation in the user, through increased parasympathetic stimulation, decreased sympathetic simulation, and/other hormonal and non-hormonal effects. This may also promote a sense of wellbeing or relaxation that may allow the user to fall asleep easier and quicker and improve sleep quality and quantity. Thus, the respiratory devices described herein represent a novel non-pharmacologic method of treating insomnia and promoting relaxation. The device may be used throughout the day and/or night to promote said relaxation and wellbeing.

The respiratory devices described herein may also be used to treat or ameliorate disorders characterized by ineffective, non-productive, or otherwise disturbed inspiration (including but not limited to obstructive sleep apnea or restrictive pulmonary disease). For example, with the device in place, a patient may be more likely to have slightly elevated lung volumes after exhalation. Put another way, more air than normal may be present in the lungs after exhalation when using some versions of the device. Fewer alveoli may be collapsed; thus inhalation may be easier because it will require less effort to re-open the alveoli during the subsequent breath. Moreover, pulmonary congestion and pulmonary edema may also be reduced, so compliance may be improved. As a result, it may require less effort for patients to inhale. It follows that a smaller pressure differential (between the alveoli and the mouth) will be required. The smaller the pressure differential, the less likely that the patient's conducting airways (including the upper airways and pharyngeal tissues) will collapse, thus reducing the likelihood of obstructive sleep apnea, hypopnea, and snoring.

Infectious diseases may also benefit from the respiratory devices described herein. These diseases include but are not limited to pneumonia (community and hospital acquired), tuberculosis, bronchitis, HIV, and SARS.

The respiratory devices may also be useful in pulmonary or cardiac rehabilitation. For example, the device may find use in patients with chronic pulmonary disease including but not limited to chronic bronchitis, emphysema, asthma, pulmonary fibrosis, cystic fibrosis, and pulmonary hypertension. Alternatively, the devices may benefit patients with cardiac disease, including but not limited to: angina, myocardial infarction, right or left sided heart failure, cardiomyopathy, hypertension, valve disease, pulmonary embolus, and arrhythmia.

Patients with obesity may also benefit from the use of the respiratory devices described herein. Obesity can contribute to exercise intolerance partly because it increases the metabolic requirement during activity and alters ventilatory mechanics by reducing functional residual capacity (FRC) and promoting atelectasis. Obesity may also reduce cardiac reserve, since a higher than normal cardiac output response is required during physical activity. This in turn may cause systemic hypertension, which increases left ventricular afterload. Thus, the device, through its potential reduction in atelectasis and beneficial effects on FRC, cardiac output, and blood pressure may be useful in patients with obesity.

The respiratory devices may also be used by athletes, for example, during both aerobic and non-aerobic activities, partially because of the potentially beneficial direct effects on the heart and on gas exchange. In some versions, the respiratory device may be oversized, to increase the amount of inspiratory airflow, potentially increasing the amount of oxygen transmitted to the lungs for gas exchange.

The respiratory devices described herein may also be used for therapeutic and non-therapeutic effects on sleep. Sleep quality may be improved, with more slow-wave sleep, fewer arousals, and improved REM sleep. The user may have more productive sleep and may be less tired during the day. Furthermore, the beneficial effects of the device may extend beyond the period of use, and into the daytime as well, even when the device's use is limited to the night (e.g., when the user is sleeping). In some cases, sympathetic discharge may be reduced and/or parasympathetic discharge may be increased. Thus, the device may have positive benefits on the autonomic nervous system. This may offer beneficial systemic effects as well as local effects, some of which have already been described.

The respiratory devices described herein may also be used in other locations besides the nasal and oral cavities. Indeed, any location in the body that is serves as an entry or exit location for respiratory airflow or serves as a conducting airway or conduit for airflow may benefit from the use of the devices described herein. For example, a device may be used within, on the external surface of, or near a stoma site (e.g., for use in a patient after a tracheostomy).

Inflammation (which is present in a variety of disease states) may also be reduced using the respiratory device, possibly via the aforementioned parasympathetic or sympathetic mediated effects and/or effects of the vagus nerve and its stimulation. The treatment of any condition mediated by an inflammatory cytokine cascade is within the scope of the devices and methods described herein. In some embodiments, the respiratory device is used to treat a condition where the inflammatory cytokine cascade is affected through release of pro-inflammatory cytokines from a macrophage. The condition may be one where the inflammatory cytokine cascade causes a systemic reaction, such as with septic shock. Alternatively, the condition may be mediated by a localized inflammatory cytokine cascade, as in rheumatoid arthritis. Examples of conditions which may be usefully treated using the respiratory devices described herein include, but are not limited to: appendicitis, peptic, gastric or duodenal ulcers, peritonitis, pancreatitis, ulcerative, pseudomembranous, acute or ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Bane syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, diabetes, ankylosing spondylitis, Berger's disease, Retier's syndrome, or Hodgkins disease.

Furthermore, the respiratory devices and methods of using them may be used by or applied to a variety of different types of animals. Representative animals with which the methods and devices find use include, but are not limited to: canines; felines; equines; bovines; ovines; etc. and primates, particularly humans. The respiratory devices described herein may also be packaged for use. For example, the respiratory devices may be packaged individually or as a set (e.g., in sets of pairs, particularly in variations in which an individual device is used with each nostril). Furthermore, the packaging may be sterile, sterilizable, or clean.

The respiratory devices described herein may also be provided as part of a kit that includes at least one of the devices. Examples of kits may include a respiratory device and instructions for how to use the device. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. The instructions may take any form, including complete instructions on how to use the device, or references, directing a user to using additional sources for instructions (e.g., a website address with which instructions posted on the world wide web).

Examples

The following examples are offered by way of illustration and not by way of limitation.

A. Removable Application in the Oral Cavity

A respiratory device adapted for use in the oral cavity (e.g., any of the devices shown in FIGS. 1-3) may be placed into a subject's mouth by medical personnel or by the subject. The respiratory device may be secured in place by the subject's teeth, gums, tongue, lips, palate or shape of the oral cavity or surrounding anatomy including the jaw, nose, chin, or skin. The respiratory device may also (or alternatively) be secured by use of an adhesive, a securing strap, or by other holdfast. The use of an adhesive may further improve the seal between the device and the oral cavity. The device may be worn during the night or day, while the patient is awake or sleeping. In some cases, the device may be worn continuously for extended periods of time (e.g., minutes, hours, days). These devices are meant to provide benefits to subjects suffering from COPD, heart failure, sleep apnea, insomnia, hypertension, gastroesophageal reflux disease, hiatal hernia and other medical conditions mentioned previously.

In some embodiments, the device works as follows. During inhalation, the valve mechanism remains in the open position as airflow proceeds from the external environment into the airways and lungs. Open position means any position in which resistance to airflow is reduced or minimized during inhalation more than exhalation. This can be achieved using any of the airflow resistor embodiments described earlier. During exhalation, the airflow from the airways and lungs to the outside environment occurs, and an airflow resistor (e.g., a valve mechanism) subjects this exhalation airflow to greater resistance than during inhalation. Thus, resistance during inhalation is less than exhalation resistance, providing the desired effect to the subject.

B. Removable Application in the Nasal Cavity

A respiratory device adapted for use in the nasal cavity (e.g., any of the devices shown in FIGS. 4, 5, 20, and 21) may be placed into one or more of the subject's nostrils by medical personnel or by the subject himself. The respiratory device may be secured in place in the subject's nostrils by the interaction between the nostril cavity and the holdfast of the device, as shown in FIGS. 4 and 5. The use of an adhesive may further improve the seal between the device and the nasal cavity. The device may be worn during the night or day, while the patient is awake or sleeping. In some cases, the device may be worn around the clock. These devices may provide benefits to subjects suffering from COPD, heart failure, sleep apnea, insomnia, hypertension, gastroesophageal reflux disease, hiatal hernia and other medical conditions, as mentioned previously.

In some embodiments, the respiratory device worn in a nasal cavity works as follows. During inhalation, the valve mechanism remains in the open position as airflow proceeds from the external environment into the airways and lungs. Open position means any position in which resistance to airflow is reduced or minimized during inhalation more than exhalation. This may be achieved using any of the airflow resistor embodiments described earlier. During exhalation, the airflow from the airways and lungs to the outside environment occurs, and valve mechanism subjects this exhalation airflow to greater resistance than during inhalation. Thus, resistance during inhalation is less than exhalation resistance, providing the desired effect to the subject. In some versions, it may be preferable to regulate the airflow of both nostrils. For example, it may be desirable to have a single respiratory device that regulates airflow into the nasal cavity (as in FIG. 27), or to have a respiratory device that has airflow resistors for both nostrils, or to simply block all airflow through one nostril and use a respiratory device to regulate airflow through the other nostril.

C. Removable Filtering Application in the Nasal Cavity:

In one embodiment of the methods for using a respiratory device, a respiratory device as shown in either FIG. 24 or FIG. 25 is placed into one of more of the subject's nostrils by medical personnel or by the subject. The respiratory device is secured in the subject's nostrils (e.g., by the interaction between the holdfast of the device and the subject's nostrils). The use of an adhesive may further improve the seal between the device and the nasal cavity. The device can be worn during the night or day, while the patient is awake or sleeping. In some cases, the device can be worn continuously. These devices may provide benefits to subjects suffering from allergies and allergy-related diseases, sinusitis, post-nasal drip, and other medical ailments as described herein.

In some embodiments, the device works as follows. During inhalation, the fixed cleansing filter 98 or moveable cleansing filter 100 filters airflow from the external environment before it passes into the airways and lungs. During exhalation, in which airflow proceeds from the airways and lungs to the outside environment, the fixed cleansing filter 98 remains in the path of the airflow, while the moveable cleansing filter 100 may deflect or move so that less airflow passes through it (and more airflow passes around it). In either case, it may be preferable for the cleansing filter not to add any additional resistance to either inspiratory or expiratory airflow, though in some cases, that addition of resistance to inspiratory and/or expiratory airflow may be desired.

D. Removable Nostril Opening Application

In one embodiment of the methods for using a respiratory device, the device shown in FIG. 22 is placed into one of more of the subject's nostrils by medical personnel or by the subject where it is kept in place by the subject's nostrils. The device can be worn during the night or day, while the patient is awake or sleeping. In some cases, the device can be worn continuously. In this way, these devices may provide benefits to subjects suffering from sleep apnea, snoring, and other medical ailments described herein as well as to subjects desiring improved athletic performance.

In some embodiments, the device works as follows. During inhalation, the device props open the nostrils to minimize airflow resistance and to prevent the nostrils from collapsing or partially closing due to negative pressures within the nose. On exhalation, the device facilitates expiratory airflow, again by propping open the nostrils and increasing the size of the lumen available for airflow.

The respiratory devices may improve the respiratory, cardiac, and general health of the patient by mimicking the effects of pursed-lip breathing, which is adopted instinctively by many affected patients or by mimicking the expiratory resistance produced by non-invasive ventilation. Physiologically, the devices described herein may provide the same beneficial effects as those experienced in pursed-lip breathing, specifically: improving oxygen saturation; decreasing respiratory rate; and increasing tidal volume. The devices may also provide beneficial cardiac effects, including: decreased blood pressure; decreased afterload; decreased preload; decreased heart rate; and improved ejection fraction. This in turn may reduce the probability of the affected patient developing hypertension, heart failure, pulmonary edema, sleep apnea and other sequelae secondary to chronic obstructive pulmonary disease or heart failure. Furthermore, the devices may offer the significant advantage of freeing the patient from constantly pursing the lips, or having to be connected to a non-invasive ventilator via a breathing tube. In contrast to pursed-lip breathing, which cannot be performed during sleep, and non-invasive ventilation devices that are used primarily at night (and cannot be used during the performance of daily activities), these devices may provide increased expiratory resistance throughout the entire day. Furthermore, respiratory devices may be provided for cleansing the inspired air and also for propping open the nostrils. These devices represent novel, non-invasive methods of treating diseases such as allergies, sinusitis, sleep apnea and others described herein.

Described here are respiratory devices, kits, and methods for their use in improving respiratory and cardiovascular function. In particular, any of the respiratory devices described herein may be configured for creating positive end expiratory pressure during respiration (PEEP) effect in a subject wearing the device are described. These respiratory devices are referred to as respiratory devices or simply as "devices." The devices and methods described herein may be useful to treat a variety of medical disease states, and may also be useful for non-therapeutic purposes. The devices and methods described herein are not limited to the particular embodiments described. Variations of the particular embodiments described may be made and still fall within the scope of the appended claims. It is also to be understood that the examples and particular embodiments described are not intended to be limiting.

The following descriptions including various design parameters or goals, and methods and devices which fit the design parameters or goals. The devices and methods described herein (and recited by any claims) are not limited to any particular theory of operation.

The devices for achieving PEEP described herein typically include: one or more passageways through which air may pass to enter or exit a respiratory orifice; a holdfast for securing the device to, at least partially over, and/or at least partially within a subject's respiratory orifice; and an airflow resistor, or airflow resistors, for regulating the passage of air through the passageway(s) to achieve PEEP. Furthermore, these devices (and methods for using them to achieve PEEP) typically do not require the application of an external pressure (e.g., from a continuous pressure source such as a pump), but operate only upon pressure generated by the subject wearing the device. Further, these devices and methods for using them may be easy to use, and may be removable and insertable by user without special tools. The devices are typically reliable, and may be small and inexpensive to manufacture.

In operation, a device configured as a PEEP device (or PEEP valve) offers only minimal resistance to inhalation, but has a very high resistance during low pressure exhalation up to a threshold pressure, and a lower resistance to exhalation above that threshold pressure. As described in greater detail below, the devices for achieving PEEP described herein may have a characteristic resistance profile.

Resistance Profiles of PEEP Devices

As used herein, the resistance profile of a device refers to the relationship between pressure across the device, and flow of air through the device. The resistance profile of a device is influenced by the shape and size of the passage(s) through the device, but it may be primarily influenced by the operation of the airflow resistor (or airflow resistors). As described in more detail below, an airflow resistor may include one or more valve or valves. Thus, in the descriptions that follow, an airflow resistor may be referred to as a valve for simplicity. However, the airflow resistors may include additional components in addition to the valve, and may also include multiple valves as part of a single airflow resistor. Thus, an airflow resistor may be referred to as a valve.

Figure 30:
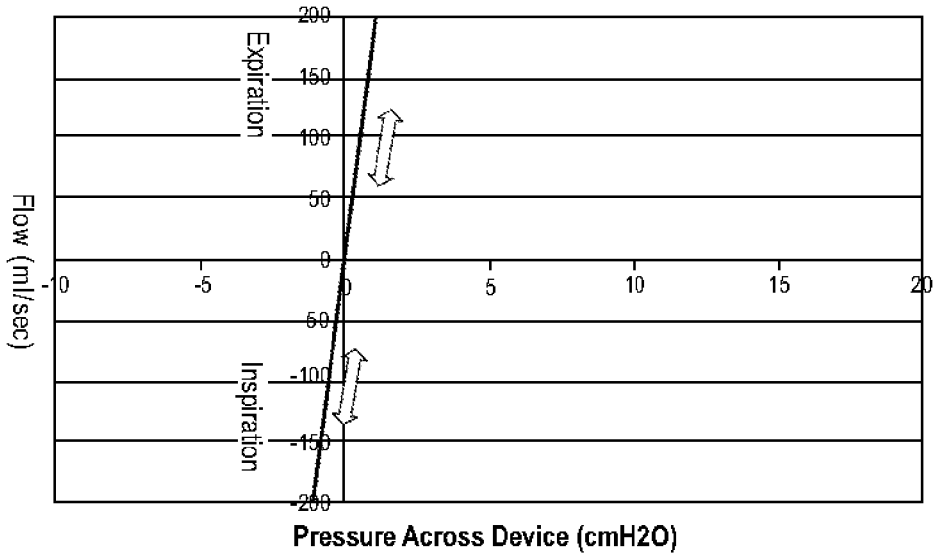
FIG. 30 shows a representative resistive profile through a hollow tubular body.

In general, a nasal respiratory device including an airflow resistor has a resistance profile to expiration and inspiration. For example, FIG. 30 shows a typical resistance profile for a tubular body (e.g., a passageway) without a valve present. By convention, the x-axis of a resistance profile shows the pressure across the device (in cm of H2O). Pressure may also be represented as the pressure difference between the subject's respiratory system (e.g., oral cavity, nasal cavity, upper respiratory tract, etc.) and the external atmosphere (atmosphere). The y-axis shows the flow through the device (ml/sec). For the sake of simplicity, the devices described by these resistance profiles are assumed to be oriented so that inspiration results in negative flow (e.g., from the proximal to the distal end of the device) and expiration results in flow in the positive direction (e.g., from the distal to the proximal end of the device). Thus, in all of the resistance profiles shown, inspiration (or inhalation) is represented by negative flow through the device, and expiration (or exhalation) is represented by positive flow through the device. As would be apparent to one of skill in the art, the orientation of the device may be switched so that the relative inspiratory and expiratory resistances may be reversed.

The resistance of the device is a function of flow/pressure, as indicated by FIGS. 1-7. For simplicity, this resistance is often referred to as the resistance of the valve.

In all of the resistance profiles described below, the pressure is expressed as pressure in cm of H2O (or "cm H2O"). A positive pressure occurs when the pressure on the side of the device fluidly connected with the inside of a subject's respiratory tract (e.g., within the nasal or oral cavity) is greater than the atmospheric pressure. A negative pressure occurs when the subject's respiratory tract pressure (e.g., intranasal or intraoral pressure) is below atmospheric pressure. For ease of explanation, the resistance profiles illustrate pressure-flow characteristics showing linear behaviors (e.g., constant slopes).

In the resistance profile shown in FIG. 30 for a device without an airflow resistor, the resistance through the passageway of the device is constant, shown as a straight line passing through the origin. Thus, for this low resistance device, as pressure increases, flow increases precipitously. The pressure-flow profile for a tubular member without a valve (or other airflow resistor) has a steep slope across both inhalation and exhalation. The slope would be infinite (e.g., vertical) showing zero resistance to flow, but because there is a finite passage size for air passage, there will always be some discernable resistance.

Figure 31:
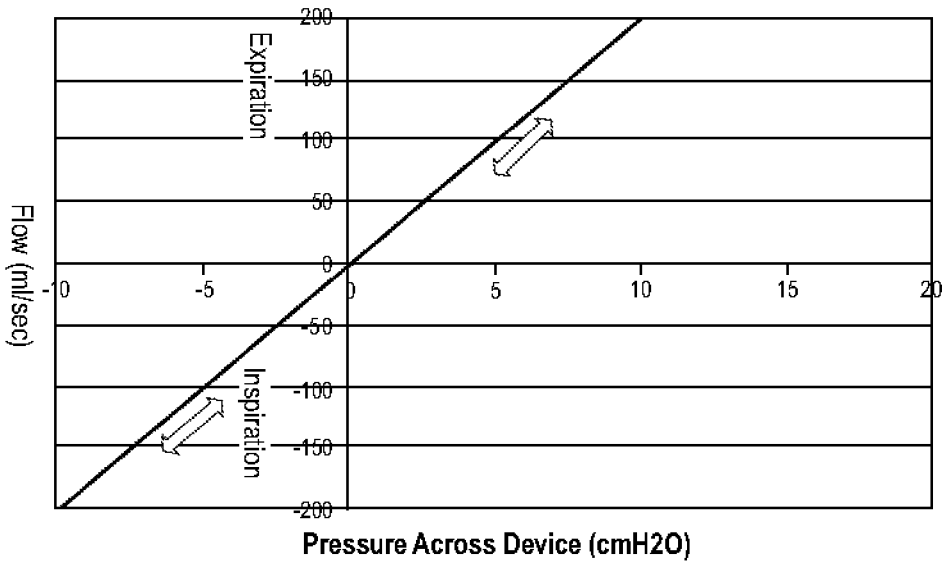
FIG. 31 shows a representative resistive profile through a hollow tubular body having a fixed resistor.

FIG. 31 shows the effect of a simple airflow resistor within the passageway. A fixed resistor such a hole that limits the size of the passageway changes the resistance, which is reflected by a decrease in the slope from the unblocked condition shown in FIG. 30. In FIG. 31, the slope has decreased (reflecting an increase in resistance) over both inhalation and exhalation, since airflow is equally impeded in either direction. The resistance is constant over the range of pressures shown for inhalation and exhalation. Thus, increasing or decreasing pressure across the device (shown by the open arrows) results in a constant rate of change (slope).

A. Simple Differential Resistance

Figure 32:
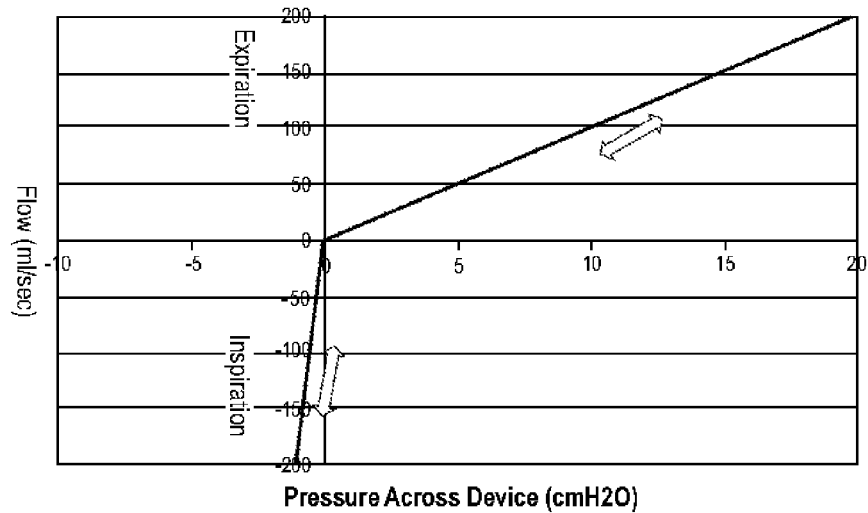
FIG. 32 shows a representative resistive profile for a simple differential resistor device.

An airflow resistor may restrict the airflow within the passageway more in one direction than another. FIG. 32 shows a resistance profile for a device having a simple "differential resistance" airflow resistor. A differential resistance device has a different resistance to airflow through the device at different parts of the respiratory cycle. As used herein, a simple differential resistance device is a particular type of differential resistive device. In general, a simple differential resistive device has a substantially constant, low resistance to airflow during inhalation, and a substantially constant but higher resistance to airflow during expiration.

Thus, a simple differential resistance device has a different resistance for inhalation than for exhalation. FIG. 32 shows a resistance profile for one example of a simple differential resistance device. This device has a low (but constant) resistance for inhalation, as shown by the steep linear slope during negative pressures, and a higher (but constant) resistance during exhalation, as shown by the flatter linear slope during positive pressures. Respiration through this device switches from inhalation to exhalation at the zero pressure point.

Simple differential resistance valves are described in detail in U.S. patent application Ser. No. 11/298,640, filed Dec. 8, 2005, herein incorporated by reference in its entirety. Exemplary respiratory devices include simple flap valves (having one or more flaps); hingeless valves; stopper-type valves; membrane-type valves; ball valves; balloon-type valves; duck-bill valves, umbrella valves, and the like, in which the valve is open during inhalation, but closed (or at least partially closed) during exhalation, and may include one or more leak passageways through which air may pass.

Other types of differential resistance devices may have different resistance profiles. In particular, a respiratory device may have different resistances at different pressures during expiration.

B. Differential Resistance Devices with Threshold for Opening During Expiration

Figure 33:
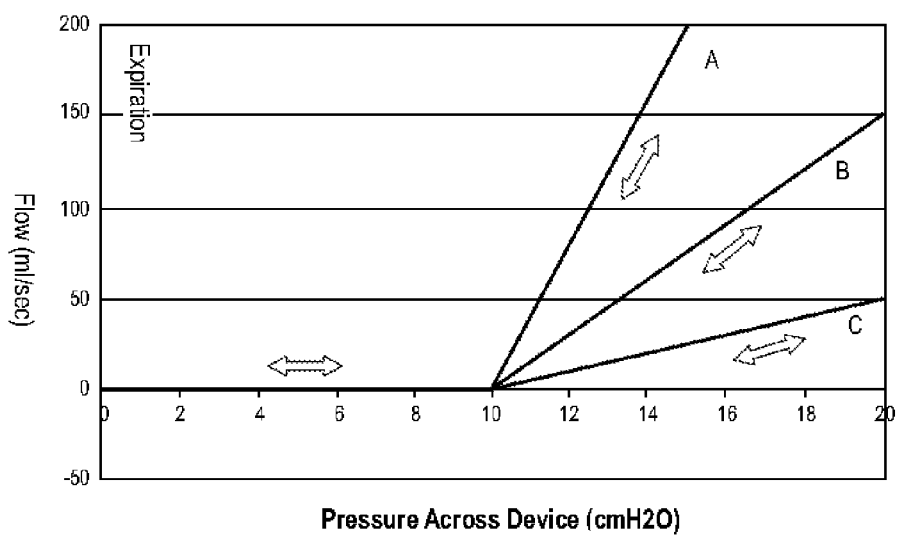
FIG. 33 shows representative resistive profiles for differential resistors with a threshold for opening.
Figure 34:
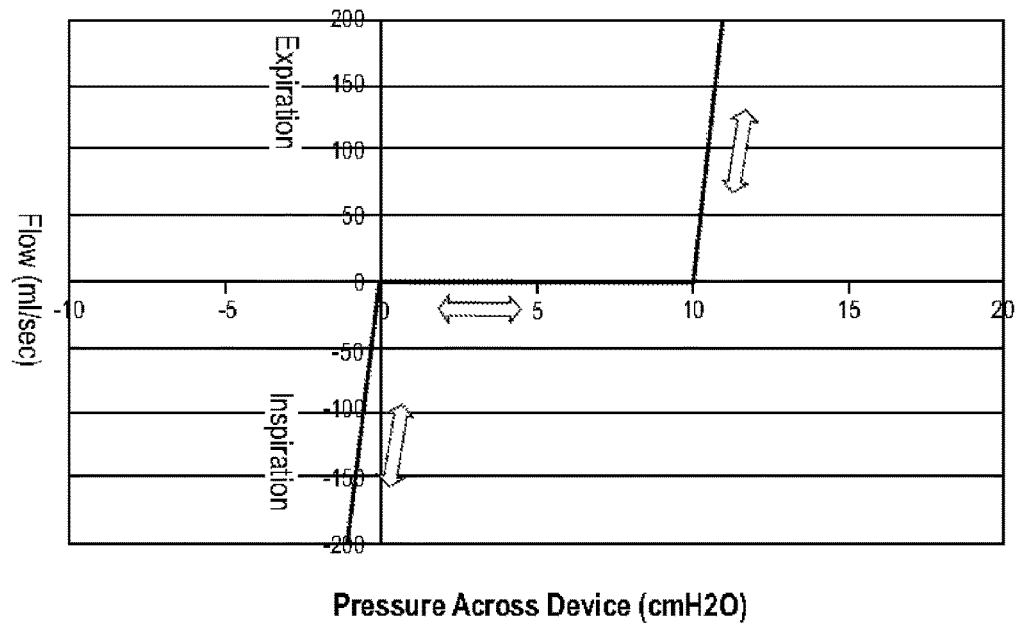
FIG. 34 shows another representative resistive profile for a differential resistor with a threshold for opening.

FIG. 33 shows a device having a resistance profile in which there is a threshold pressure for opening during expiration. In FIG. 33, for convenience, only the flow over the positive (expiration) pressures is shown. The inhalational pressure (negative pressures) can be assumed to be a constant low pressure, as shown in FIG. 34. In FIG. 33, the resistance of the device at low expiratory pressures across the device (e.g., between 0 cm of H2O and 10 cm of H2O) is infinite, shown by the flat slope. At 10 cm of H2O, the resistance decreases to a constant level. Three different cases (shown by the three different lines, A, B and C) are shown for devices having three different constant resistances. Thus, in this example, the threshold pressure for opening is 10 cm of H2O.

Thus, in some variations, it may be desirable to block all (or substantially all) flow at low pressures during expiration until a predetermined pressure threshold for opening is reached. After this threshold is reached, the device (e.g., a valve within the device) opens, allowing air to flow through it. Depending upon the resistance to flow when the device opens, you can have many different pressure-flow relationships above this threshold value, as seen by lines A, B and C. For example, line A represents a lower resistance device, line B represents a moderate resistance device, and line C represents a higher resistance device. In any of these devices, it does not matter whether the pressure is increasing or decreasing, as the flow will match the pressure differential for any pressure across the device.

FIG. 34 shows another example of a differential resistance device having a threshold for opening during expiration. A device having the resistance profile shown in FIG. 34 may be ideal for PEEP. During inhalation (at negative pressure across the device), the device has a very low resistance (e.g., the airflow resistor may be substantially open during inhalation). During exhalation at low pressures (e.g., between zero and the threshold for opening of 10 cm of H2O) there is no flow. For example, the airflow resistor is closed. Above the threshold for opening, the resistance again drops, because air may flow through the airflow resistor.

In an actual differential resistance device having a threshold for opening during expiration, there may be some flow at low pressure, although this may be very high resistance flow (e.g., around the edge of the valve), which would be seen on a resistance profile as a relatively flat (though not completely flat) slope. In addition, although the resistance profiles shown herein have abrupt transitions between high and low (or low and high) resistance regions, in practice the slopes may transition gradually (e.g., as the valve opens or closes).

Differential resistance devices having resistance profiles such as those shown in FIG. 34 may be useful as PEEP devices because they may help maintain positive end expiratory pressure within the subject's respiratory tract. For example, near the end of the expiratory portion of a respiratory cycle the pressure by which air is expelled may decrease as expiration ends. Thus, a subject expiring through a differential resistance device having a threshold for opening such as the one shown in FIG. 34 may be prevented from completely expelling air during expiration, resulting in a positive end expiratory pressure. In some variations, a respiration device configured as a PEEP device has a threshold for opening of less than about 15 cm H2O, less than about 12 cm H2O, less than about 10 cm H2O, less than about 8 cm H2O, less than about 4 cm H2O, etc. For example, the threshold for opening may be between about 1 cm H2O and about 15 cm H2O, or between about 1 cm H2O and about 10 cm H2O.

Exemplary devices having resistance profiles similar to those shown in FIG. 34 are described more fully below, in the section titled "Exemplary Devices." In general, these devices may include an airflow resistor that is configured to be open during inhalation, and is closed at low pressure during exhalation, but at some threshold for opening, the airflow resistor opens to allow flow. For example, the airflow resistor may be biased in the direction of expiratory flow so that the pressure across the airflow resistor must exceed some threshold amount before it opens. In some variations, the airflow resistor is a bistable valve, which changes from a first stable configuration (e.g., closed during low-pressure expiration) to a second stable configuration (e.g., open during high-pressure expiration) when the pressure across the device reaches the threshold pressure.

In some variations (particularly bistable valve variations), the transition from open during high-pressure operation to closed during low-pressure operation does not occur at the same threshold pressure. These devices may have a resistance profile similar to that shown in FIG. 35.

C. Differential Resistance Devices with Threshold Release During Expiration

Figure 35:
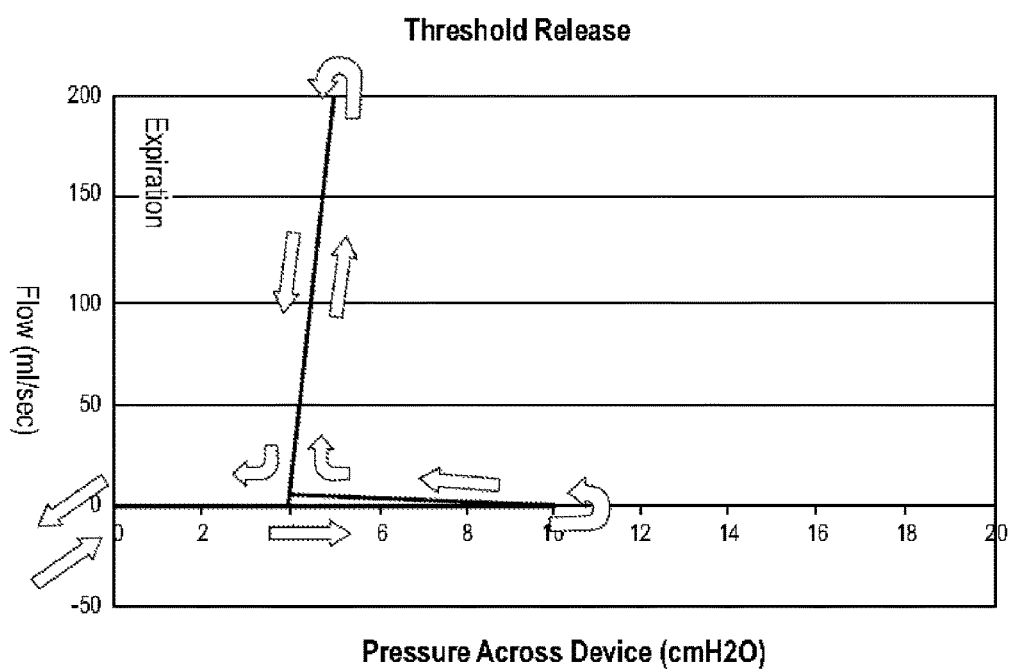
FIG. 35 shows a representative resistive profile for a differential resistor with a threshold for opening and a threshold for closing.

FIG. 35 shows a differential resistance device with a threshold for opening and a threshold release during expiration. This means that during expiration, at low pressure the device is closed, but when the pressure across the device reaches a first threshold (the threshold for opening) the valve in the device opens to allow airflow. However, this open valve does not close until the pressure across the device reaches a second threshold (a threshold pressure for closing).

For simplicity sake, only the expiratory portion of the resistance profile is shown in FIG. 35. At low expiratory pressures across the device (e.g., between zero and the threshold for opening shown here as 10 cm of H2O) the device is effectively closed, preventing any airflow across the device (e.g., having an infinite resistance). When the airflow resistor is closed, but the pressure across the device exceeds the threshold for opening, the airflow resistor will open, allowing airflow with a low resistance. In this embodiment, however, the airflow resistor does not re-close (e.g., reset) when the pressure across the device falls below the threshold for opening. Instead, the pressure must fall below a threshold for closing during expiration. In FIG. 35, this threshold for closing is approximately 4 cm of H2O.

The threshold for closing is the pressure at which the device is 'reset' back into the closed during expiration mode from the open during expiration mode. Once the device has closed, and flow has substantially stopped, the device will remain closed during expiration until the threshold for opening (e.g., 10 cm of H2O) is again exceeded.

The resistance profile shown in FIG. 34 may be thought of as a special case of the situation described above for FIG. 35, in which the threshold pressure to return the airflow resistor closed during expiration is the same as the threshold pressure required to open the airflow resistor during expiration.

As mentioned above, resistance profiles similar to the one shown in FIG. 35 may be demonstrated by devices having bistable valves which change from a first stable configuration (e.g., closed during low-pressure expiration) to a second stable configuration (e.g., open during high-pressure expiration) when the pressure across the device reaches the threshold pressure. Example of differential resistance devices with a threshold for opening and a threshold release during expiration are also given below.

FIG. 36 shows another variation of a differential resistance device with a threshold for opening and a threshold for release during expiration. In FIG. 36, the threshold for release (e.g., closing the airflow resistor) during expiration is approximately zero cm of H2O. Thus, the device doesn't "reset" closed during expiration until after the inspiration occurs.

Devices having resistance profiles similar to those shown in FIG. 35 may also be useful as PEEP devices. In particular, devices in which the threshold pressure to return the airflow resistor to a closed state during expiration is greater than some minimum level (e.g., greater than 1 cm H2O, greater than 2 cm H2O, greater than 3 cm H2O, greater than 4 cm H2O, greater than 5 cm H2O, etc.) may make effective PEEP devices. As described above, these valves may help maintain a positive end-expiratory pressure within the subject's respiratory tract at the end of an expiratory cycle of respiration. The threshold pressure for closing may be any appropriate pressure values, particularly pressures in the range of: between about 0.5 cm H2O and about 15 cm H2O, between about 1 cm H2O and about 10 cm H2O, etc.

It should be apparent that the resistance profiles described above are idealized profiles. In practice, the pressure-flow characteristics may be non-linear, and may be curved or have other non-straight lines. The profiles shown here illustrate general characteristics of resistance profiles. As described above, although figures such as FIGS. 5 to 7 show resistance profiles having flat regions (of infinite or very high resistance) when a valve is 'closed' during expiration, the valve may include one or more leak pathways through which air may pass. Thus, devices corresponding to the resistance profiles shown in the figures (e.g., FIGS. 5 and 6) may have a non-zero slope even when the valve is closed during expiration.

Furthermore, the profiles described above are time-independent, and thus do not accurately reflect the time dependence of any of the devices described herein. As will be apparent, the time response of the respiratory device may also affect the operation of the device. For example, it may be desirable to delay the response of the change in resistance based on the time point of the respiratory cycle. For example, it may be beneficial for a PEEP device to delay closing the valve after switching from inhalation to exhalation, even though the respiratory pressure is relatively low across the valve.

General PEEP Devices

The respiratory devices described herein alter airflow into and out of the lungs through a respiratory cavity such as the mouth and/or the nostrils of the nose in order to achieve positive end-expiratory pressure (PEEP). These respiratory devices typically include one or more passages, a holdfast for securing the device in communication with a subject's respiratory cavity, and an airflow resistor (e.g., valve) capable of obstructing airflow with high resistance during low-pressure expiration, and opening to allow substantial airflow during high-pressure expiration. In particular, the respiratory devices may include an airflow resistor having a threshold pressure during expiration for opening the airflow resistor to allow airflow when the threshold pressure is exceeded. In some variations, the airflow resistor also has a threshold for closing during expiration, below which the airflow resistor inhibits expiratory airflow until the threshold pressure for opening is again exceeded. Specific examples of devices having appropriate airflow resistors are described below.

Any of the devices described herein may be specifically adapted for nasal use. Thus, these devices may be considered nasal respiratory devices. For example, the devices may include a holdfast for securing the passageway(s) in communication with the nasal cavity to regulate airflow through the nasal cavity. The holdfast may secure the device at least partially over and/or at least partially across the nose (particularly in contact with the area around the nasal opening). In some variations, the holdfast secures the device at least partly within the nasal cavity. Nasal devices described herein may be configured so that they do not cover the subject's mouth, and therefore the subject may be free to breathe through the oral cavity without additional resistance.

The respiratory devices described herein generally comprise an airflow passageway and an airflow resistor. The airflow passageway (or "passageway") generally defines a channel allowing the passage of air. The passageway may be of any suitable size or shape; however it is configured so that when the respiratory device is worn by a patient, the passageway comprises an opening leading toward the patient's lungs in fluid connection with an opening that leads away from the patient's lungs. The terms "patient" and "subject" are used to describe any user of the respiratory device, including users who are not using the respiratory device for therapeutic purposes. The airflow passageway may be any suitable length. For example, the passageway may be as short as the airflow resistor will allow (e.g., extending only far enough to communicate with the airflow resistor). Similarly, the airflow passageway may be longer than the space required to support the airflow resistor. For example, in versions of the respiratory device adapted for at least partial insertion into a nasal cavity, the airflow passageway may be approximately as long as the length of an average nare. In some versions, the passageway extends the length of an average nasal chamber.

The neutral cross-sectional area of the passageway may be of any appropriate size. Neutral cross-sectional area may refer to the cross-sectional area of the passageway when the device allows air to flow through the passageway without additional resistance (e.g., from the airflow resistor). In particular, the size (e.g., diameter) or shape of the passageway may depend upon configuration of the respiratory device. For example, respiratory devices configured to be inserted within the nasal cavity (e.g., a nasal chamber) may have an area that is approximately the area of a narrow portion of the nasal cavity, or slightly narrower. Respiratory devices configured to be secured over an oral cavity or a nasal cavity may have passageways of larger diameters. Furthermore, the cross-sectional area of a passageway may vary along the length of the device.

The airflow passageway may comprise a dedicated structure defining the inner wall of the airflow passageway, or it may be a structural component of the device. For example, the passageway may comprise a passage wall defined by a rim. A rim may be a tube (or tunnel) of material of any appropriate thickness. The rim may also be a frame, rather than a complete tube. The rim may comprise a sufficiently rigid material so that it can support the passageway, and prevent the passageway from collapsing during use and during respiration. In some versions, at least a portion of the rim is made of a compressible material that may be compressed to facilitate insertion and removal, while maintaining the ability to support the passageway and prevent complete collapse of the passageway during respiration. The rim may also be somewhat compressible during respiratory flow. The airflow passageway (including a rim portion) may also serve as an attachment site for other components such as airflow resistors, filters, anchors, etc.

The rim may be any suitable shape or size. For example, the rim may comprise a ring shape or an oval shape. As mentioned above, the rim may define the inner diameter of the passageway. In some versions, the rim comprises a material having strength sufficient to prevent the collapse of a respiratory device that has been inserted into a nasal cavity. For example, the rim may comprise a metal, a polymer (particularly stiff polymers), etc. In some versions, the rim may comprise softer or "weaker" materials which are formed or arranged so that the final shape of the rim has sufficient strength to prevent the collapse of the respiratory device during use.

As mentioned above, a respiratory device may include a rim that is a tube or tubular body having a distal end and a proximal end, through which the airflow passageway extends. In variations of the device that are adapted to be secured in a subject's nasal cavity, the distal end of the respiratory device is inserted first into the subject's nose, so that the device is worn so that during inhalation air flows from the proximal to the distal end of the passageway, and during expiration air flows from the distal to proximal end of the passageway. In some variations, the proximal end of the tubular body has different properties from the distal end. For example, the thickness of the tubular body from distal end to proximal end may vary.

In some variations, the respiratory device has a tubular body in which the distal end is more compliant than the proximal end. Thus, the distal end may be more readily compressed for insertion into the nasal cavity, while the proximal end is somewhat more rigid, allowing for easier removal/insertion of the device. A more compliant distal end may also help the device better fit a subject wearing the device, and may enhance comfort. As described more fully below, the distal region of the device may conform to fit the nasal cavity.

In some variations, the distal end is more compliant than the proximal end because different regions of the tubular body are made from different materials or have different structures. For example, a distal portion of the tubular body may have a wall thickness that is less than the wall thickness of the more proximal portion of the tubular body. The rim (e.g., tubular body) may have two or more regions of different wall thickness, or it may have regions of continuously varying thickness. The wall thickness may be uniform for a given distal-to-proximal position (e.g., along the length of a respiratory device's tubular body). As mentioned above, the wall thickness of the tubular body (rim) may be zero in some regions, meaning that the tubular body includes holes or windows, or comprises a frame.

Regions of different wall thickness may result in different regions of the airflow passageway having different diameters or cross-sectional shapes. For example, in variations where the respiratory device has a tubular body having a proximal wall thickness that is greater than the distal wall thickness, the region where the thicker proximal wall thickness meets the thinner distal wall thickness may form a step or ledge along the wall of the passageway. In this example, the outer diameter (OD) of the tubular body is uniform while the inner diameter (ID) has at least two different measures. As described in more detail below, this ledge or step within the passageway may form a valve seal surface by providing a surface on which a valve (e.g., a flap valve) may abut or lie against when in the closed position.

The tubular body may have any appropriate cross-sectional area. For example, a rim configured as a tubular body may have an elliptical cross-section through its length that is shaped similarly to that of most patients' nares. This shape may help maximize the cross-sectional size of the passage while maintaining comfort. The passageway may also comprise other cross-sectional shapes, such as circular, polygonal, teardrop, or other asymmetric shapes.

In some versions, the respiratory device does not include a separate rim forming the passageway. For example, the airflow passageway of the respiratory device may be a passageway through a holdfast.

The devices described herein may include more than one passageway. Furthermore, although many of the illustrations of devices provided herein are for nasal devices (e.g., devices for use in a nasal cavity), it is to be understood that these devices may be adapted for use with any respiratory orifice (e.g., mouth, nose, etc.).

Airflow resistors for use with the PEEP devices described herein are typically positioned in communication with an airflow passageway, so that at least some (if not all) of the air flowing through the passageway passes the airflow resistor. Thus, an airflow resistor modulates, alters, varies, or keeps constant the amount of resistance, the degree of airflow, or the pressure differential across the device or through a passageway in the device. As described above, a typical PEEP airflow resistor has very little resistance to inhalation, has a high resistance to expiratory airflow at low expiratory pressures, and has a threshold pressure for opening, above which the airflow resistor has a relatively low resistance to expiration. In some variations, the airflow resistor (e.g., a valve) has a threshold pressure for closing during exhalation, so that if the pressure across the valve during expiration falls below the threshold for closing, the airflow resistor will close, resulting in a high resistance to flow.

Examples of different types of airflow resistors are described below and illustrated in many of the figures. Any airflow resistance device having a resistance profile similar to the resistance profiles shown in FIG. 33, FIG. 34 and FIG. 35 may be used.

Some variations of the airflow resistors described are modified flap valves. The flap region may include a stiff or flexible material, or some combination thereof. In some variations, the flap valve includes a stiff region of the valve, which may help give the flap support. In some variations, the flap comprises a polymeric material, as described below. The flap valve may be biased (e.g., in an open or a closed position) or it may be unbiased. A bias element such as a spring may be used, or the flap may be made of a material that has elastomeric properties that bias the valve in a particular position. A biased valve is a valve that tends to remain in a particular position (e.g., flat, bent, open, closed, etc.) when at rest, and changes position (e.g., from closed to open) after an appropriate force is applied to the device to overcome the bias. As described herein, the bias may be provided by a biasing element (e.g., spring, tether, weight, or the like), or a material property of the valve (e.g., the stiffness). The airflow resistor may also be used with additional components. For example, respiratory devices may include an airflow resistor seal surface (valve seal surface), an airflow resistor support (valve support), and/or an airflow resistor aligner (valve aligner). Examples of these features are provided in more detail in U.S. patent application Ser. No. 11/805,496 titled "NASAL RESPIRATORY DEVICE," filed May 22, 2007 by inventors Rajiv Doshi, Bryan Loomas, and Ryan Kendall Pierce, the entirety of which is herein incorporated by reference in its entirety.

The airflow resistor or valve may be any appropriate shape, particularly shapes in which the passageway may be blocked or at least partly occluded.

The respiratory device may also include one or more leak paths. A leak path allows air to flow through or past the respiratory device even when the airflow resistor is closed. A leak path may be included as part of any portion of the device, including the holdfast, the rim (e.g., the tubular body), or the airflow resistor. The sizes, locations and distributions of the leak path(s) may be chosen to permit a desired amount of airflow through the device at a known pressure and/or flow rate. In particular, the leak path may be incorporated as part of an airflow resistor. For example, the leak path may be one or more holes or channels through the valve, even when the valve is closed. In some variations, the leak path is not included as part of the valve.

The PEEP respiratory device may further comprise a holdfast for releasably securing the device in communication with a nasal cavity. The holdfast may facilitate the positioning and securing of the device in a desired location, such as over or within (e.g., substantially within) a nasal orifice. In particular, the holdfast may allow the device to be anchored, positioned, and/or stabilized in any location that is subject to respiratory airflow such as a nasal cavity.

Nasal cavities may include the following anatomical structures, or conduits defined by the following anatomical structures: the nostrils, nares or nasal chambers, limen, vestibule, greater alar cartilage, alar fibrofatty tissue, lateral nasal cartilage, agger nasi, floor of the nasal cavity, turbinates, sinuses (frontal, ethmoid, sphenoid, and maxillary), and nasal septum. The term "nasal cavity" may refer to any sub-region of the Nasal Fossa (e.g., a single nostril, nare, or nasal chamber).

In some versions, the holdfast may also secure a seal between the respiratory device and the respiratory airway, so that at least some of the air exchanged between the outside of the patient and the respiratory airway must pass through the respiratory device. In some versions, the holdfast seals the device in communication with a respiratory cavity completely, so that all air must be exchanged through the device. In some versions, the holdfast seal is incomplete, so that only some of the air exchanged between the patient and the external environment passes through the device. As used herein, "air" may be air from the environment external to the patient, or it may be any respiratory gas (e.g., pure or mixed oxygen, $CO_2$, heliox, or other gas mixtures provided to the user). In some versions, the holdfast may comprise an anchor or anchor region.

In some variations, the device is to be placed by the patient or the healthcare provider in or around the nasal cavity. Holdfasts appropriate for nasal cavities may secure the device in position within a nasal cavity (e.g., through one or both nostrils) or against surrounding structures. The holdfast may comprise a shape, surface or material that secures the device in communication with a nasal cavity. For example, the holdfast may comprise a cylindrical shape that allows the device to fit securely or snugly within a nostril. The outer surface of the device may comprise a holdfast including an adhesive material. In addition to holding the device in place, the holdfast may also partially or completely seal the device in communication with the nasal cavity. The holdfast may comprise insertive and/or non-insertive mechanisms. In some versions, the holdfast comprises a mechanical connection between the device and the user, such as clips, straps, and the like.

The holdfast may be formed from a soft or compliant material that provides a seal, and may enhance patient comfort. Furthermore, compliant materials may reduce the likelihood that the device cuts off blood flow to the part of the respiratory cavity and surrounding regions to which the device is anchored. This compliant material may be one of a variety of materials including, but not limited to, plastic, polymers, cloth, foamed, spongy, viscoelastic, and/or shape memory materials. Shape materials include any that have a preferred conformation, and after being deformed or otherwise deflected or altered in shape, have tendency to return to a preferred conformation. Soft shape memory materials may include, but are not limited to, urethane, polyurethane, sponge, and others (including "foamed" versions of these materials). Alternatively, the holdfast may not be soft or compliant and may instead be a rigid structure that interfaces directly with the respiratory orifice. For example, in versions of the respiratory device configured to be used at least partly within a nasal cavity, it is understood that the device may fit completely within a nostril (or both nostrils), or may project out of the nostril, depending on the particular embodiment. In some cases, the device may be placed high enough within the nasal cavity so that it cannot be seen within the nostril. In some embodiments the device may be located completely outside of the nose, for example, in some versions the holdfast has a shape that conforms to the outside surface of the nose. Thus, the holdfast may comprise one or more straps, bands, or the like to ensure an adequate fit and/or seal maintaining the device in communication with the nasal cavity. In another embodiment the holdfast may comprise one or more projections that are inserted within the nostrils. In some versions, a device may be placed at least partly in both nostrils, and may comprise a bifurcated passageway or two passageways that the holdfast places in communication with the nasal cavity through each nostril. In this case, the inspiratory and/or expiratory airflow to and from the lungs may be regulated through each nostril separately or together. In some versions, separate devices may be placed at least partly in each nostril, and may be connected to each other and/or to the patient using a clip, tether, strap, band, chain, string, or the like. In these versions, the connection means may connect one rim from one device to a rim from a second device or a holdfast from one device to a holdfast from a second device, or some combination thereof. Any portion of one device may be connected by said connection means to any portion of the second device. The connection means may comprise a shape memory material. Such a system would facilitate subsequent removal of the device and make migration of the devices deeper into the nasal cavity less likely. Finally, in some devices, an adhesive region may be present to help attach the device to the inside or outside of the nose (including the nostrils), to the oral cavity, to the neck, or to the face. The use of an adhesive or any other means may prevent the inadvertent or otherwise undesired removal of the subject devices during sleep.

The holdfast portion of a respiratory device may also be shaped to fit within the subject's anatomy to secure the device in place and/or to prevent leakage of airflow around the device. For example, the holdfast may be shaped to fit within the widening of the nasal cavity immediately inside the nares (opening of the nostril). As mentioned above, the holdfast may conform to the walls of a portion of the nasal cavity both to hold the device within the nose, and also to prevent substantial leak of air around the device when worn in the nose. Materials such as foams (e.g., foamed polyurethane) may be particularly useful for this purpose, since these materials may be readily compressed for insertion and rapidly expand within the nasal cavity to secure the device in place.

A holdfast may be attached to a respiratory device. For example, a holdfast may be attached to a rim. In one variation, the holdfast is connected to the outer surface of the tubular body. A holdfast may be glued, taped, stitched, welded, or otherwise connected to the rim of a respiration device. In some variations the holdfast circumferentially surrounds at least a portion of a rim. For example, in one variation the distal end of the tubular body (e.g., rim) of the device is ensheathed by a holdfast of foamed material. In some variations, the holdfast thickness is substantially uniform along most or all of the periphery of the device. In some variations, it may have variable thickness, for example it may be thicker or thinner at the long ends of the device. In other cases, the holdfast thickness may be either symmetrically or asymmetrically distributed. Similarly, the height and length of the foam forming a holdfast may also be uniform or non-uniform, symmetrically or asymmetrically distributed.

A holdfast may be thicker in some regions than in other regions. For example, the cross-sectional profile of the holdfast (e.g., the profile though the long axis of a respiratory device including a holdfast) may be thicker in some places than in others. In some variations, e.g., when the tubular body or passageway of the device has an elliptical profile (cross-sectional profile), the holdfast in communication with the tubular body is thicker near the long axis of the elliptical profile of the tubular body than at the short axis of the tubular body. In some variations, the thickness of the holdfast around the profile of the tubular body cross-section is related to the diameter of the passageway through the device. For example, the thickness of the holdfast at any point outside of the passageway may be between about 0.2 times and about 2 times the distance from the center of the passageway to the outer edge of the tubular body around the radius of the passageway. On an exemplary device having a tubular body with an elliptical profile, the holdfast may be between about 0.8 mm and about 8 mm thick at the long axis of the elliptical cross-section of the tubular body, and between about 0.4 mm and about 4 mm thick at the short axis of the elliptical cross-section of the tubular body.

The device may be removably secured by a holdfast, meaning that the device may be inserted into the subject's nasal cavity for some amount of time, and then removed. For example, a removable holdfast exerts sufficient pressure on the nostril walls (e.g., within the nasal cavity) to hold the device in position without harming the subject, or producing too much discomfort. The device may be used continuously for an appropriate time period (e.g., overnight, such as 6-8 hours). Thus, the holdfast does not generally need to be secured more permanently. The holdfast material properties and shape typically lend themselves to easy, fast, and pain-free insertion and removal. Thus, as described herein, the holdfast may be a compressible/expandable foam material. The shape and size of the holdfast may also be chosen to appropriately secure the device within a subject's nasal cavity comfortably. For example, the foam may have compression properties that allow it to be readily compressed (for insertion into the nasal cavity), but expand to fit the cavity quickly once inserted. The holdfast may also have a thickness and width sufficient to fit snugly but comfortably within the subject's (including an 'average' subject or range of different subject sizes) nasal cavity. In some variations, the foam thickness is not uniform. For example, in some variations, the ends of the holdfast region comprise a foam that is thicker than in the middle, which may allow the device to fit noses which are longer and narrower.

Respiratory devices may be made from any appropriate material or materials. In certain embodiments, the devices include a shape memory element or elements, as part of the holdfast, in the airflow resistor, or in giving form to the passageway. Any convenient shape memory material that provides for flexibility and resumption of configuration following removal of applied force may be employed in these embodiments. For example, shape memory alloys may be used. A variety of shape memory alloys are known, including those described in U.S. Pat. Nos. 5,876,434; 5,797,920; 5,782,896; 5,763,979; 5,562,641; 5,459,544; 5,415,660; 5,092,781; 4,984,581; the disclosures of which are herein incorporated by reference in their entirety. The shape memory alloy that is employed should generally be a biocompatible alloy. Biocompatible alloys may include nickel-titanium (NiTi) shape memory alloys sold under the Nitinol™ name by Memry Corporation (Brookfield, Conn.). Also of interest are spring steel and shape memory polymeric or plastic materials, such as polypropylene, polyethylene, etc.

Rubber and polymeric materials may also be used, particularly for the holdfast, rim, or airflow resistor. Injection moldable materials such as polyether block amide (e.g., PEBAX®), and the like may be used. Materials which may be used include: latex, polyethylene, polypropylene, polystyrene, polyvinyl chloride, polyvinylidene chloride, polyvinyl acetate, polyacrylate, styrene-butadiene copolymer, chlorinated polyethylene, polyvinylidene fluoride, ethylene-vinyl acetate copolymer, ethylene-vinyl acetate-vinyl chloride-acrylate copolymer, ethylene-vinyl acetate-acrylate copolymer, ethylene-vinyl acetate-vinyl chloride copolymer, nylon, acrylonitrile-butadiene copolymer, polyacrylonitrile, polyvinyl chloride, polychloroprene, polybutadiene, thermoplastic polyimide, polyacetal, polyphenylene sulfide, polycarbonate, thermoplastic polyurethane, thermoplastic resins, thermosetting resins, natural rubbers, synthetic rubbers (such as a chloroprene rubber, styrene butadiene rubber, nitrile-butadiene rubber, and ethylene-propylene-diene terpolymer copolymer, silicone rubbers, fluoride rubbers, and acrylic rubbers), elastomers (such as a soft urethane, water-blown polyurethane), and thermosetting resins (such as a hard urethane, phenolic resins, and a melamine resins).

Biocompatible materials may be used, particularly for those portions of the device (e.g., the holdfast) which may contact a user. In addition to some of the materials described above, the biocompatible materials may also include a biocompatible polymer and/or elastomer. Suitable biocompatible polymers may include materials such as: a homopolymer and copolymers of vinyl acetate (such as ethylene vinyl acetate copolymer and polyvinylchloride copolymers), a homopolymer and copolymers of acrylates (such as polypropylene, polymethylmethacrylate, polyethylmethacrylate, polymethacrylate, ethylene glycol dimethacrylate, ethylene dimethacrylate and hydroxymethyl methacrylate, and the like), polyvinylpyrrolidone, 2-pyrrolidone, polyacrylonitrile butadiene, polyamides, fluoropolymers (such as polytetrafluoroethylene and polyvinyl fluoride), a homopolymer and copolymers of styrene acrylonitrile, cellulose acetate, a homopolymer and copolymers of acrylonitrile butadiene styrene, polymethylpentene, polysulfones polyimides, polyisobutylene, polymethylstyrene and other similar compounds known to those skilled in the art.

Exemplary Devices

The following exemplary devices contain valve mechanisms that may be used to achieve PEEP, and therefore may be referred to as PEEP devices or PEEP valves. Many of these examples describe only airflow resistors or the valve components of an airflow resistor, however it should be understood that these airflow resistors or valves may be used as part of a respiratory device. It should also be understood that a single device may include more than one of these valves.

The valves described herein may be used as part of a PEEP device having a resistance profile similar to that of FIG. 34 (exemplifying a differential resistance devices with a threshold for opening during expiration), and FIG. 35 (exemplifying a differential resistance devices with a threshold for closing during expiration).

A. Differential Resistance Devices with a Threshold for Opening During Expiration In general, differential resistance devices having a threshold for opening during expiration comprise one or more valves that open (or open more fully) to reduce the resistance through the valve only after the pressure across the valve exceeds the threshold for opening. In some variations of these devices, the threshold for opening is determined by a bias which must be overcome before the valve (or valves) can be opened. In particular, a bias may be preloaded, so that the valve cannot be opened until the preloaded force is overcome. Thus, the threshold pressure for opening a valve may be the preloaded force.

One class of resistance devices having a threshold for opening during expiration are valves having nested flaps, where the flaps open in opposite directions, as shown schematically in FIGS. 47A-47C. In particular, nested flap valves may be used for PEEP devices when one of the flaps is biased so that it opens only after the pressure across the valve exceeds a threshold for opening. Thus, a nested flap valve may be configured so that the resistance profile resembles the profile seen in FIG. 34, for example.

The generic nested flap valve shown in FIG. 47A has two flaps, a first flap and a second flap, that are each hinged. In FIG. 47A (during inhalation), the first flap is opened during inhalation, so that air may flow from the top of the valve to the bottom of the valve. Relating this to the resistance curve shown in FIG. 34, during inhalation (negative pressure), the first flap of the valve is easily opened, and has a very low resistance. FIG. 47B shows the valve flap during exhalation. The positive pressure moves the first flap to close off the passageway (the passageway is not shown). At positive pressures (exhalation) below the threshold for opening the second flap, the first flap closes the passageway but the pressure across the valve is not sufficient to open the second valve. Thus, the second flap is biased so that it only opens when the pressure exceeds the threshold pressure for opening. Any appropriate bias may be used. A bias applies force to oppose the opening of the flap. For example, the second flap may be biased by a structural bias (e.g., a spring), an elastomeric material (or region of the valve), or a combination of these. The second flap may be biased because of the material property of the hinge region or the flap itself. Once the pressure across the valve during expiration exceeds the threshold for opening, the second flap opens, allowing airflow through the device during exhalation. This is illustrated in FIG. 47C.

The flaps of a nested flap valve may be oriented in any appropriate orientation. For example, in FIGS. 47A-47C, the flap valve is oriented so that both flaps are hinged in parallel. In some variations, it may be desirable to orient the flaps so that they open in different directions. Thus, the hinges of the nested flaps may be perpendicular, or parallel, or any appropriate angle.

Figure 48B:
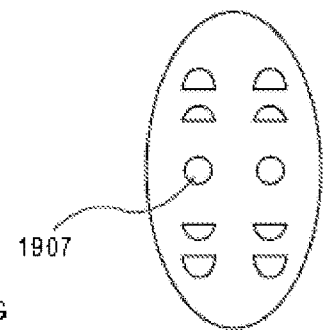

A living hinge may be used with any of the appropriate valves described herein, including flap valves. Thus, in FIGS. 47A-47C, either the first or second flap may be formed (e.g., cut, molded, etc.) from the same material. Thus, the valve may include a living hinge and a region that deflects under pressure, allowing airflow. The size and shape of the opening formed by the deflectable material (as well as the shape and size of the living hinge) may determine the resistance to airflow through the valve. FIG. 48A illustrates an examples of living hinges for a valve similar to the nested valve in FIGS. 47A-47C. FIG. 48A shows four nested flaps 1901 cut into the body of the first flap 1903. The flap also includes holes 1907 (e.g., post holes) for mounting to one or more valve aligners. The nested flaps are shown as semi-circular cutout regions of the flap having a living hinge between the ends of the cutout region. These hinged flaps may allow airflow, and will open when pressure is applied. The amount of pressure required to open these flaps may be effected (or controlled) by the length of the hinge, the size (e.g., area) of the cutout region, the thickness and/or stiffness of the material, the effective moment arm (e.g., the distance from the flap hinge to the effective position of rotational force from the pressure), etc. The living hinge region (the region that is not cut out) may also be shaped by partially shaping or cutting the material forming the hinge region. For example, the hinge region may be undercut or thinned to make opening easier.

FIG. 37A shows another example of a device having nested flap valves. A first ("inspiratory") pair of flap valves (hinged 801 together in the center of the passageway) open easily during inspiration, when pressure is greater from proximal region of the device, shown here towards the top of the device. A second ("expiratory") pair of flap valves 803 is located on each of the inspiratory flap, and hinged 805 to open during expiration, when pressure is greater from distal region of the device, shown here towards the bottom. The flap door of the second pair of flap valves is biased using an elastic spring member, as shown in FIG. 37C in a cross-section though one of the pairs of nested valves. Thus, when pressure across the valve during expiration exceeds the threshold for opening which is set by the elastic spring member, the valve will open. FIG. 37D shows a side view of the surface of the inspiratory valve, showing the embedded expiratory valve thereon.

Figure 38A:
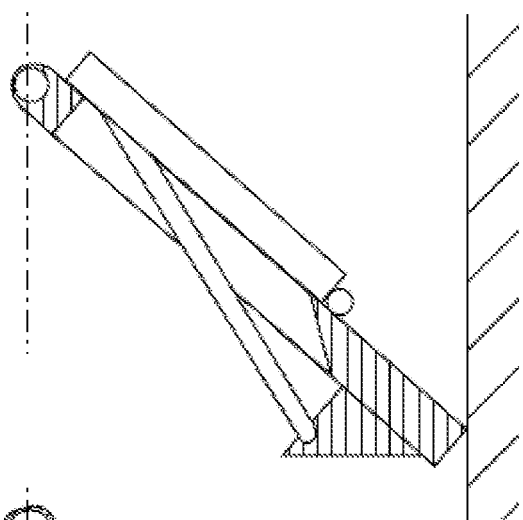
FIGS. 38A, 38B and 38C illustrate the operation of a door-within-a-door valve as described herein.
Figure 38B:
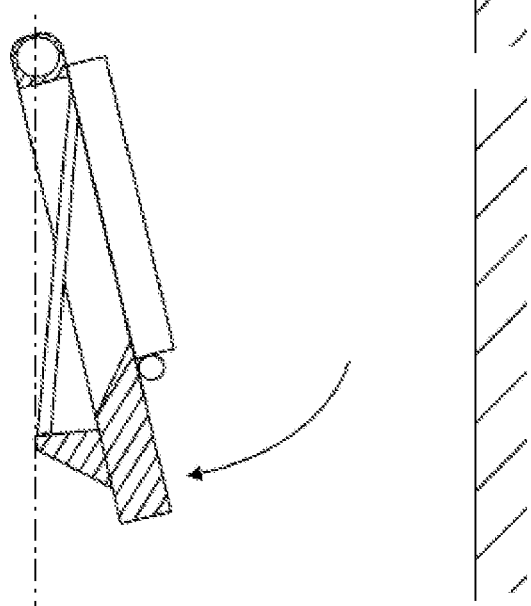
Figure 38C:
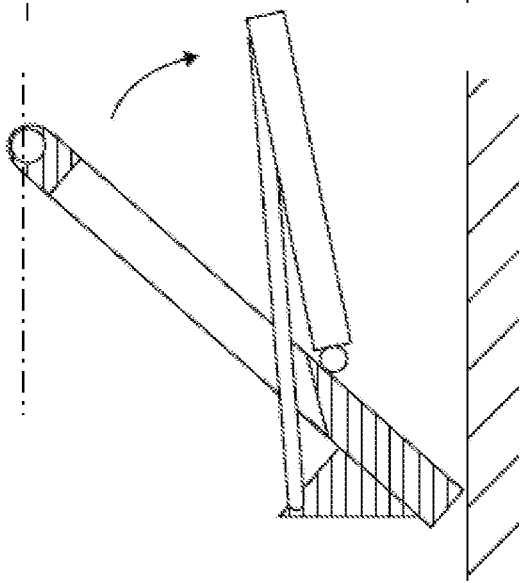

In operation, the valve shown in FIGS. 37A to 37D operates as shown in FIGS. 38A to 39C. At rest, the valve (or pairs of valves) is closed, cutting off flow through the passageway. As shown in FIG. 38B, during inspiration, when air is flowing from the proximal to the distal (e.g., shown as top to bottom) ends of the device, the inspiratory flap valve(s) opens to allow airflow through the passageway relatively unobstructed. The valves in FIGS. 37 and 38 are relatively stiff flap valves, so that the valves do not collapse during normal operation. During expiration, the inspiratory flap valve closes, and the force applied by the subject during expiration acts across the expiratory valve, which is biased by the elastic spring member (or any appropriate bias). If the pressure across the valve is greater than the force applied by the elastic spring member, then the expiratory valve opens, as shown in FIG. 38C.

As mentioned briefly above, the force applied by the spring member in FIGS. 37A to 38C corresponds to the threshold pressure for opening. Thus, the threshold pressure for opening can be adjusted or predetermined based on the bias element characteristics, including the attachment of the bias element (here, the spring member) to the valve.

FIGS. 39A to 39C illustrates the effect of bias position on the threshold pressure for opening. In FIG. 39A, the valve stays closed until a predetermined pressure is reached across the valve (a threshold pressure for opening), and then the valve opens, allowing maximum outflow until the pressure decrease below the threshold. This variation comprises a single flap valve that is in communication with the walls of the passageway, and is hinged or otherwise flexibly (movably) connected at one end. This valve may be incorporated into a device such as the device shown in FIGS. 37A to 38D.

In FIG. 39A, the valve is shown in cross section as a stiff valve 1001, connected to a bias 1003 (e.g., a spring, elastomeric material, etc.). In FIG. 39A, the biasing force applied by the spring as the valve is opened is likely to decrease slightly as the valve leaf (flap) is deflected open by pressure across the valve. Thus, the placement of the bias may affect the amount of force required to open the valve completely or partially. FIGS. 39B and 39C show arrangements of the bias element 1003 which may result in an almost constant force, adding little additional resistance to completely open the valve once initial pressure is exceeded. Thus, the placement of a biasing element may be chosen so that the threshold pressure required to fully open the valve remains constant, or increases as resistance through the device decreases (as the valve opens).

Another variation of a nested flap valve is shown in FIGS. 40A and 40B. In FIG. 40A the valve includes an inspiratory door 1103 (flap) portion that opens during inspiration, and an expiratory door 1101 portion built into the inspiratory door, that may open during expiration. Both the inspiratory door and the expiratory door are stiff members, and both are rectangular when viewed perpendicular to their faces, as shown in the top view of FIG. 40B. The passageway may be adapted to have a rectangular cross-section so that the valve can seat within the passageway and obstruct airflow through the passageway unless the doors are open. The dashed lines indicated by 1105 show the open position of the valve during inspiration. During inspiration, when the valves open, both the upper and lower flap valves open and move together. During expiration, only the nested expiratory door opens when the expiratory pressure across the door is greater than the threshold for opening, as indicated by the dashed lines 1107.

FIGS. 41A-F show another variation of the door-within-a-door type (e.g., nested) valve described in FIG. 40. This variation may be fabricated from an elastomeric material. In some variations, the doors of the valve are hinged using a living hinge as described, where the hinge regions are cut into the hinge shape to allow flexion. FIG. 41A shows a top view of the airflow resistor including this valve through the passageway. FIG. 41B shows a cross-section through the side of the airflow resistor, and FIG. 41C shows a bottom view from within the airflow resistor. An alternative top view is shown in FIG. 41D, in which a sealing face or ledge 4101 is included for the door to seal or rest against. FIG. 41E shows a cross-sectional view of the airflow resistor shown in FIG. 41D, and FIG. 41F shows a bottom view of the same airflow resistor.

Figure 49B:
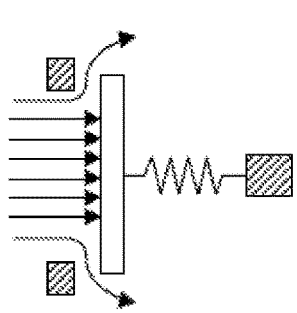
FIGS. 49A and 49B illustrate the operation of a rigid plate valve.
Figure 49A:
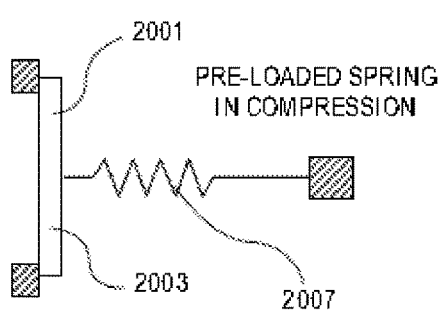
Figure 49C:
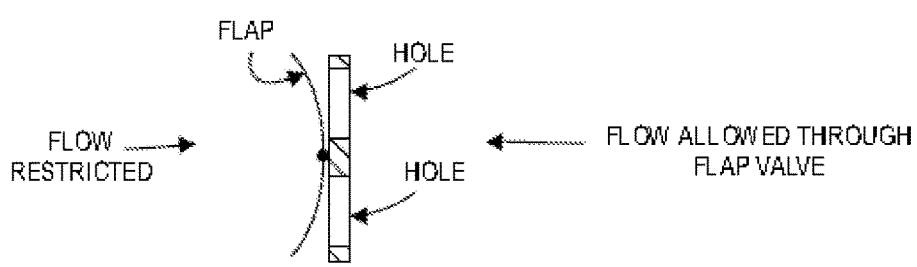
FIG. 49C shows a flap valve compatible for use with a plate valve.
Figure 49D:
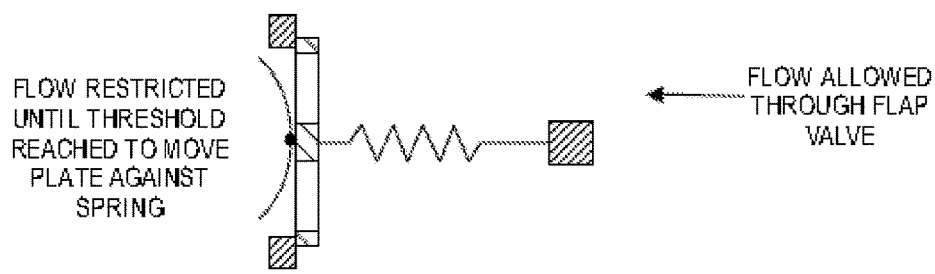
FIG. 49D shows a hybrid rigid plate and flap valve configured for use with a PEEP device, as described herein.

FIGS. 49A to 49D show an example of a valve appropriate for an airflow resistor of a PEEP device in which a flap valve is combined with a rigid valve. In FIG. 49A a rigid valve 2001 is biased against a valve seal region 2003. The bias 2005 is preloaded in compression so that it tends to hold the rigid valve against the valve seal. When the pressure acting on the rigid valve exceeds the force applied by the bias (e.g., the preloaded compressive force), the rigid valve is pushed away from the seal, opening to allow the passage of air around the rigid valve, as shown in FIG. 49B. Thus, in this example, the preloaded compressive force establishes the threshold pressure for opening. FIG. 49C shows a dual flap valve having two flaps covering two openings (holes). This flap valve is combined with the rigid and biased valve shown in FIGS. 49A and 49C to form a valve that may be configured to create PEEP, as shown in FIG. 49D.

Figure 49E:
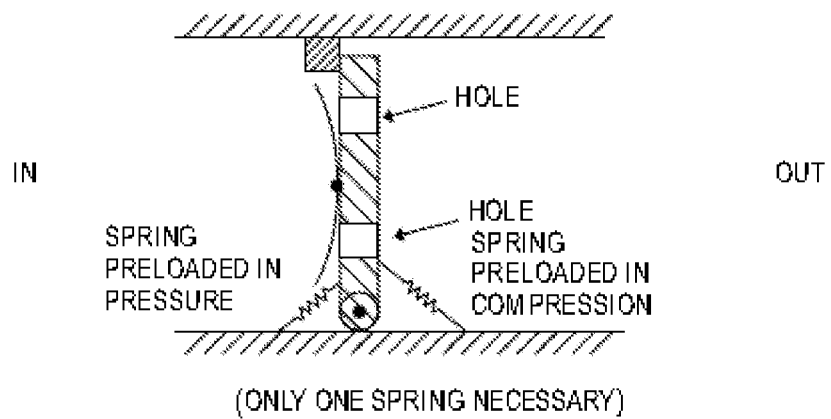
FIGS. 49E, 49F and 49G illustrate different variations of a hybrid rigid and flap valve similar to the valve shown in FIG. 49D.
Figure 49F:
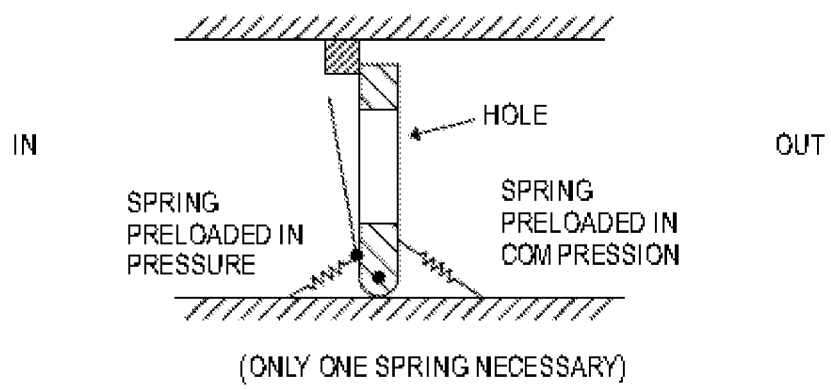
Figure 49G:
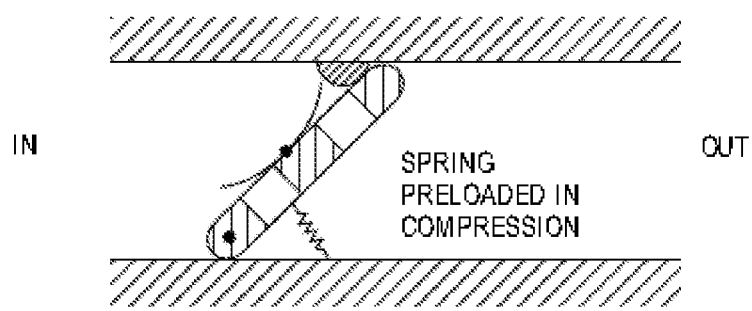

FIGS. 49E-49G show different variations of airflow resistors comprising valves that may be used as part of a PEEP device, similar to the biased flap valve shown in FIG. 49D. For example, in FIG. 20E, the rigid region of the valve is not biased at its center, but is instead biased so that it opens like a door (on one side). The rigid region of the valve also includes two biases, a bias for compression as well as tension. The combination of different biases may be used to more accurately control the resistance profile of the valve, and in particular, may be used to set the threshold for opening during expiration (e.g., flow 'out' of the device, as indicated by the 'in' and 'out' directions).

In FIG. 49F, the flap valve is also shown as a side-hinged valve. In general, a flap valve rotates around a fixed point when force is applied at some distance from that point, causing deflection of the flap relative to the point and/or mechanical deformation of the flap. Thus, a flap may be more easily opened by increasing the distance between the force applied to the flap and the flap attachment point (e.g., the moment arm). The moment arm may be increased (as shown in FIG. 49B) by increasing the movable area of the flap. In some variations the length of the moment arm may also be increased by increasing the distance between the hinge and the opening through which the force is applied. This may be achieved, for example, by building the flap valve so that it sits at an angle with respect to the passageway.

Figure 42A:
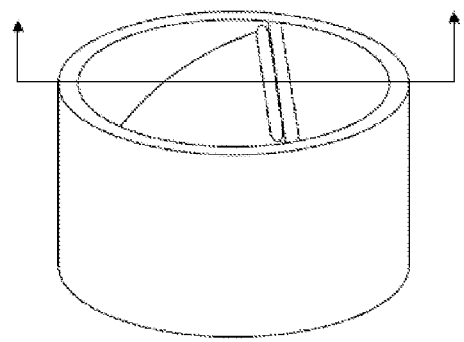
FIGS. 42A and 42B show perspective and cross-sectional views of a region of a respiratory device having two passageways.
Figure 42B:
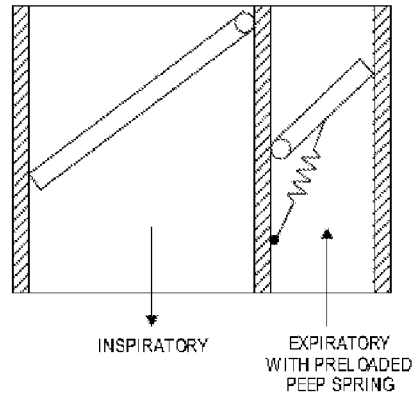

In some variations, the PEEP device may comprise more than one passageway, in which each passageway includes a valve. In this example, one passageway is used for inspiration, and one is used for expiration. For example, FIG. 42A shows a perspective view of a PEEP device having two passageways. A cross-sectional view is shown in FIG. 42B. The inspiratory side of the device includes a flap valve that readily opens during inspiration, but remains closed during expiration. The cross-sectional area of either passageway may be equal, or one of them may be bigger than the other (e.g., the expiratory passageway may be smaller than the inspiratory passageway). The expiratory side includes a biased valve (similar to the valves described above), which is set to open when the pressure across the device exceeds the threshold for opening. The bias 1301 shown in FIG. 42B is schematically indicated. One embodiment of this bias includes an elastomeric band (e.g., spring), as shown in FIGS. 43A-43D.

Figure 43A:
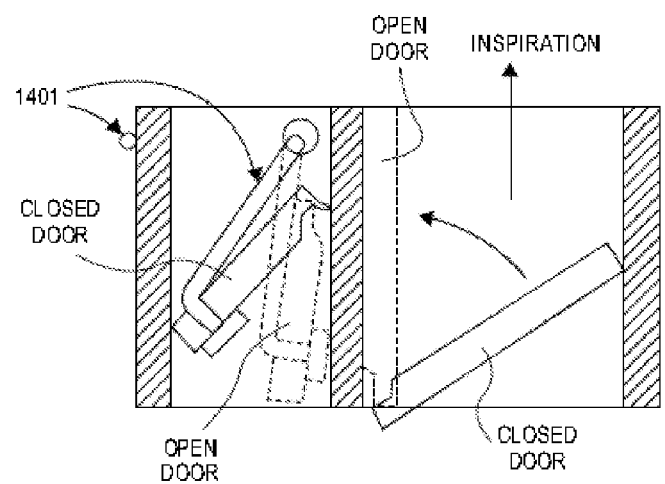
FIG. 43A shows a cross-sectional view of a region of a respiratory device having two passageways, as described.

In FIGS. 43A-C, the PEEP device includes two chambers, as shown in the cross section shown in FIG. 43A. The elastomeric element 1401 (shown in FIG. 43B) is wrapped around the outside of the passageway after passing through holes on either side of the passageway to connect to the flap and bias it within the expiratory passageway. This is shown in FIG. 43C, in a top view of the closed expiratory valve. In this variation, the elastomeric element is attached by passing through a hole in the flap, where it anchors on the opposite side of the flap.

FIGS. 44A, 44B and 44C show alternative ways to anchor the bias (e.g., a spring or elastomeric element) to the expiratory flap valve shown in FIGS. 43A-43C. In FIG. 44A a spring is anchored (e.g., via a hook) thorough a hole fabricated on the flap. In FIG. 44B, the bias is a wire that passes through the flap and anchors beneath it. In FIG. 44C, the bias connects to a loop of wire that is pushed through a hole in the door (flap).

Figure 53A:
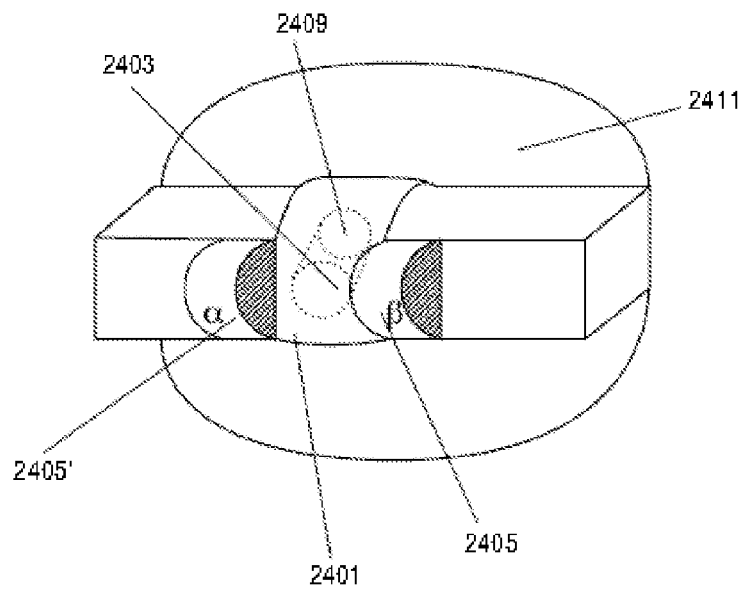
FIG. 53A illustrates another variation of a valve that may be included as part of a two or more passageway PEEP device.
Figure 53B:
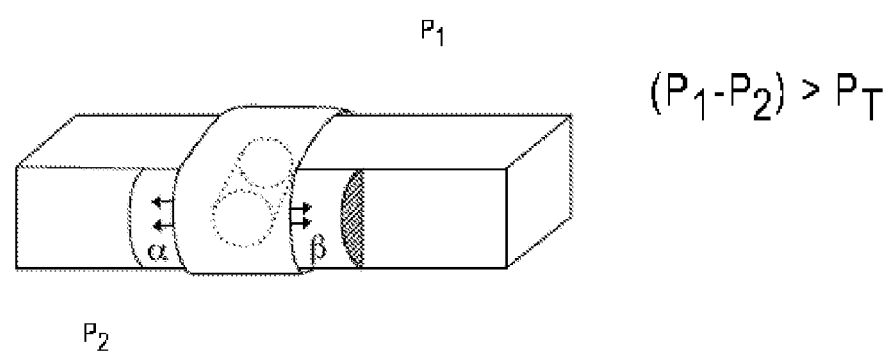
FIG. 53B illustrates another variation of the valve shown in FIGS. 53A and 53B.

Another variation of a valve that may be included as part of a two or more passageway PEEP device is shown in FIGS. 53A and B. In FIG. 53A, an elastomeric membrane 2401 is positioned over only one end of a passageway 2409, and other passageways may be substantially blocked off by an occlusive wall 2411 (for convenience, not shown in the additional FIGS. 53B to 53D). The membrane 2401 is positioned so that a threshold pressure (PT) is required to displace the membrane from over an opening 2403. Airflow is therefore blocked until the elastomeric membrane is deflected, as shown in FIG. 53B. Thus, when the pressure differential (P1-P2) is reached in this variation, the membrane stretches beyond the reach of the structures 2405, 2405' conforming to the expansion path of the elastomeric membrane (e.g., the accommodating path surface). The threshold pressure may be determined by the membranes stiffness and the geometry of the airflow pathway, including the accommodating path surface, as described in more detail below. FIGS. 53C and 53D illustrate another variation of the valve shown in FIGS. 53A and 53B.

Figures 50A, 50B:
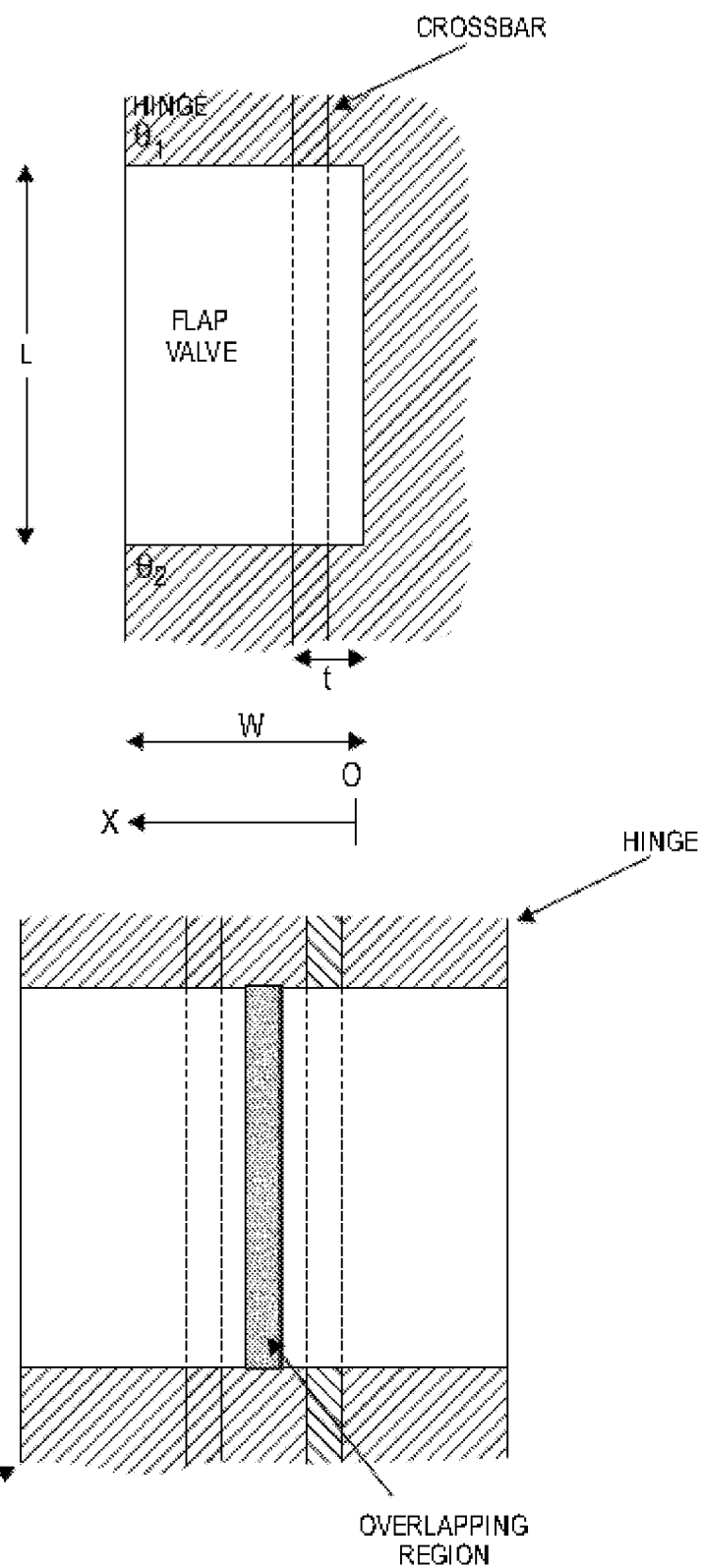
FIG. 50A shows a flap valve configured to have a pressure profile as shown in FIG. 61.
FIG. 50B shows another flap valve configured to have a pressure profile as shown in FIG. 61.

FIG. 50A shows one example of a valve that is not typically configured for PEEP, but that may be used in combination with a bias or with another valve to achieve PEEP. FIG. 50A shows a flap valve that is hinged on one side, and is constrained from opening during expiration (e.g., into the page), by a crossbar. During inspiration, the valve bends (out of the page), permitting airflow. In some variations, the flap valve bends everywhere along the length of the valve (e.g., $0 \leq x \leq w$). In other variations, bending during inspiration is focused on the area near the hinge (e.g., x approximately equal to w), and the flap may be reinforced elsewhere, or may comprise a more rigid material or greater thickness. The valve may be relatively easily opened during inhalation because of the relatively large surface area of the flap, and the large moment arm. During exhalation, the valve is constrained for easily opening by the crossbar, however, since there is no "preload" (e.g., bias) on the distal region of the flap, it will simply open a little with a little pressure, and more with greater pressure, resulting in a pressure profile similar to the profile shown in FIG. 61. In one variation, the flap is stiff, and the crossbar is an elastomeric material. Thus, the crossbar yields during exhalation to open the valve.

FIG. 50B illustrates another variation of a valve which may be used as part of a PEEP configured device. Two or more flaps (e.g., such as the flap shown above in FIG. 50A) may be arranged to overlap to provide a resistance profile having a threshold for opening. For example, in FIG. 50B two flaps are hinged, and each valve is constrained from opening during exhalation by a crossbar, similar to FIG. 2A. The flaps are arranged in an overlapping saloon-door configuration, so that there is an overlapping region between the crossbars. The flaps may open easily during inspiration, as described above for the variation shown in FIG. 50A. During expiration, the distal region of each flap (furthest from the hinge region) is constrained from opening at the region past the crossbar by overlapping region. The flaps may be continuously flexible (so that they can bend everywhere along their length) or relatively stiff. Thus, a PEEP resistance profile may result, since the two doors need to move a certain distance (providing a preload) before air can get by them.

Figure 51:
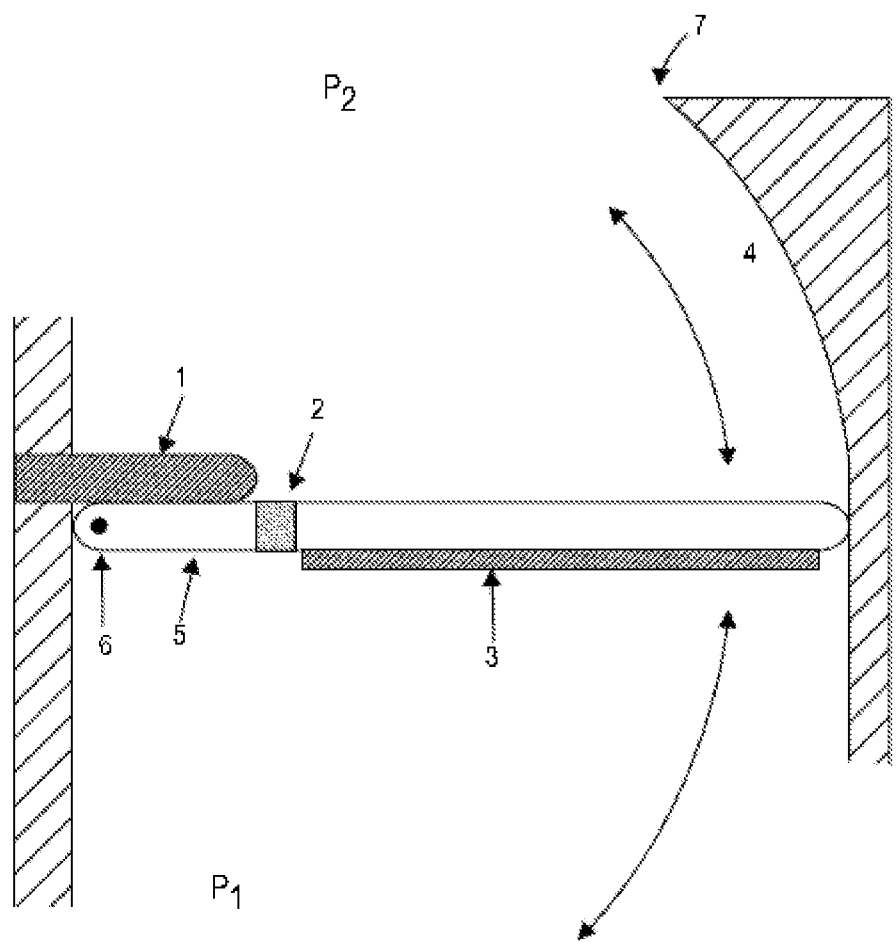
FIG. 51 shows another variation of a PEEP device having a resistance profile similar to that in FIG. 63.
Figure 63:
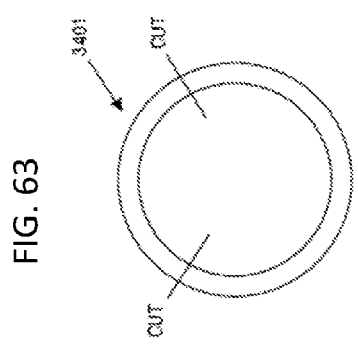
FIG. 63 illustrates one method of making a bistable valve, as described herein.

FIG. 51 shows another variation of an airflow resistor including a valve that is configured to operate as part of a PEEP device having a resistance profile similar to that in FIG. 63. The valve includes a door 5 that is hinged 6 so that during inhalation, the door opens without much resistance (inhalation is airflow towards the distal direction, e.g., P2>P1). During exhalation, stopper 1 prevents the door 5 from rotating open beyond the set position. Further rotation of the door 5 in the direction of the exhalation (e.g., the proximal direction), requires bending around a hinge region 2 that is part of the door. This second hinge region 2 may resist bending because of material stiffness of the door, and/or contact between the door and the surface of the passageway region opposite of the door 4. The surface of the passageway opposite the door 4 in the proximal direction of the passageway (e.g., in the proximal direction) may be configured to prevent opening of the valve during exhalation as the door bends in the distal direction. Thus, in FIG. 51, the surface of the passage 4 is curved to prevent airflow during exhalation until the pressure across the valve (the pressure differential P1−P2) is large enough to push the end of the door 5 past the curvature of the wall 7 at the end of the curved surface 4. In the variation shown in FIG. 51, the door is augmented with a support 3 that stiffens it so that the door does not readily bend in this region. The support 3 may therefore help localize bending to the hinge regions, which may help prevent flow thorough the device until the door has passed the end of the shaped region of the passageway 4. The threshold for opening during expiration for this device may therefore be controlled by the flexibility of the second hinge region 2, the surface area of the door 5, and the geometry of the shaped region of the passageway 4. The shaped region is a path-accommodating surface that may interact with the flap or door of the valve. Thus, in this example, the valve is biased in the exhalation direction (P1>P2) by the stiffness of the second hinge region 2, which must bend a preset amount (along the curved passageway 4) before the valve can open.

The device shown in FIG. 51 is also adjustable. In particular, the threshold for opening during exhalation is adjustable. For example, the stopper 1 maybe adjusted by moving it further into or out of the passageway. In one variation, the stopper is threaded so that it may be screwed further into or out of the passageway. Adjusting the length of the stopper within the passageway may affect the ability of the door 5 to deflect during exhalation. For example, adjusting the length of the stopper may reduce or increase the curvature of that the door bends with, which may increase or decrease interference around the shaped region of the passageway 4. The stopper length may also determine how much of the second hinge region 2 is available to bend.

Figure 52A:
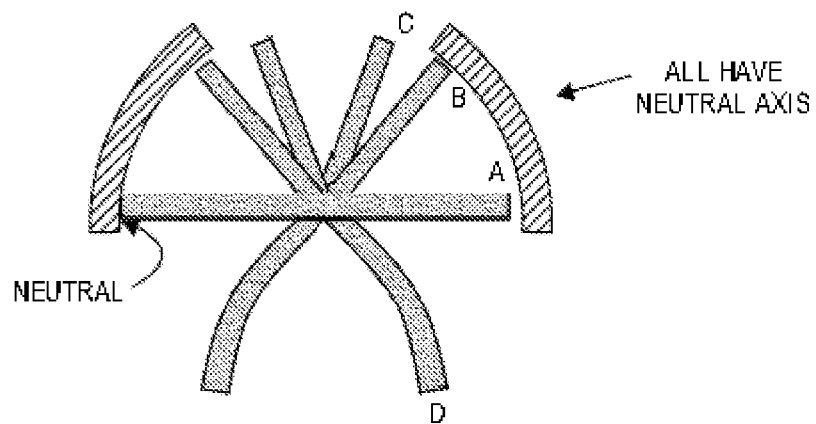
FIGS. 52A and 52B illustrate a portion of a valve having a path accommodating surface that helps to regulate the resistance profile of the valve similar to that in FIG. 63.

FIG. 52A illustrates the general use of a path accommodating surface to regulate the resistance profile of a valve. In FIG. 52A, a cross-section though a flap and path accommodating surface shows that the flap in four positions. In the first (neutral position), indicated by position A, the flap blocks off both inhalation (by convention, in the downward or distal direction of the figure as drawn), and exhalation (by convention, upward or proximal in the figure as drawn). During inhalation the valve readily moves out of the way, forming a space between the wall of the passage in the distal direction, and the valve through which air may flow, as shown in position D. However, during exhalation, the walls of the pathway conform to the movement path of the valve in the proximal direction. Thus, the space between the flap(s) and the wall is limited, as shown in position B, until the flaps pass the conforming region, shown in position C. When the flaps are in position C, air may pass through the device during exhalation. Thus, a valve having an accommodating path surface may have resistance profile similar to that shown in FIG. 63.

Figure 52B:
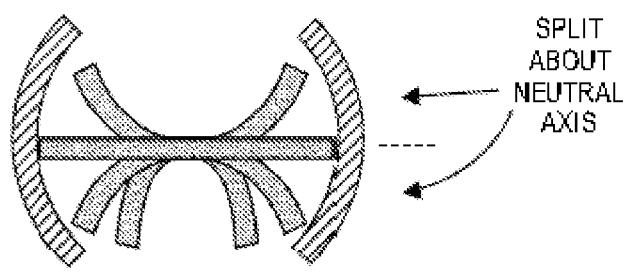

An accommodating path surface may also be adjusted by adjusting the distance between the path (e.g., wall) surface and the flap, as well as the extent to which the wall is an accommodating path surface. FIG. 52B shows a variation in which the accommodating path wall surface has been split around the neutral position, as shown.

Figure 46A:
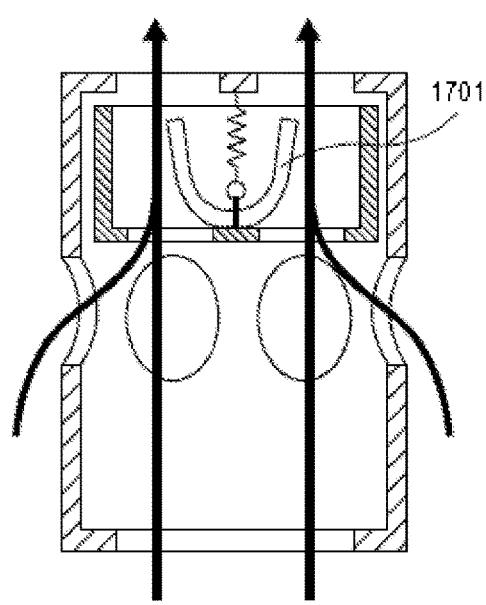
FIGS. 46A, 46B, 46C and 46D illustrate the operation of a respiratory device configured for PEEP.
Figure 46B:
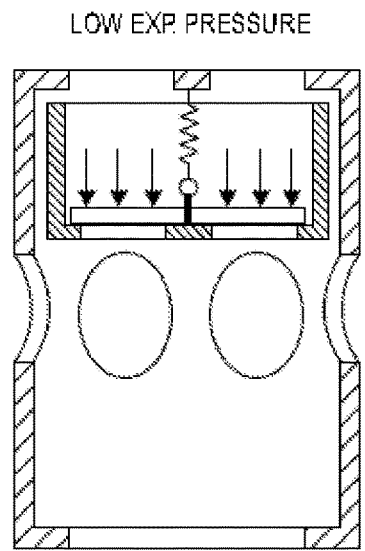
Figure 46C:
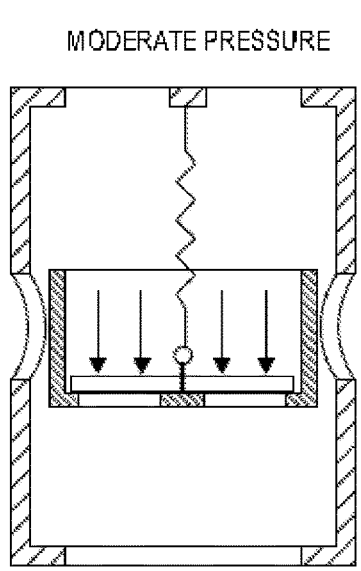
Figure 46D:
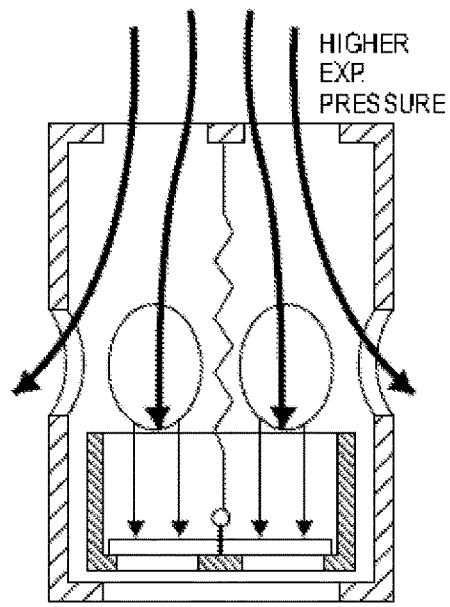

FIGS. 46A-46D show another variation of a PEEP device. This PEEP device includes an airflow resistor that comprises a platform that moves based on expiratory pressure against a bias. The bottom of the platform comprises a flap valve that is open during inspiration, but closed during exhalation. For example, FIG. 46A show the valve during inhalation, in which the flap valve 1701 (e.g., a silicone flap valve) is open as air is drawn up the valve. In the neutral position, or during very low pressure exhalation, the flap valve 1701 is closed, and the platform is biased (e.g., by the spring or elastomeric material) so that expiratory flow does not pass (e.g., from the top of the figure down). At moderate expiratory pressure the platform moves against the bias as shown in FIG. 46C, however the platform walls block the exit holes through the passageway, so airflow is still not possible. Once the expiratory pressure across the device is greater than the threshold for opening the valve (determined in part by the bias and the geometry of the platform), the valve opens, allowing respiratory airflow, as shown in FIG. 46D. FIG. 46E shows a side view of what this device might look from while in a subject's nostril.

Any of the respiratory devices described herein (including the PEEP configured devices) may be dual-nostril devices that cover both nasal cavities, or they may be configured for use in a single nostril. If they are configured for use in a single nostril, each device may include one or more valves to control airflow, as described above. In many variations, it may be beneficial to configure the respiratory device so that both nostrils are combined into a common lumen through which respiratory airflow is regulated. There is a limited cross-sectional area within each nostril with which to provide low resistance during inhalation and higher resistance during exhalation using the valves and vents as described herein. The effective cross-sectional area may be increased by extending the device to the region just outside of the nostril and/or combining the nostril passageway into one effective passageway. This passageway could span the area between the nares of each nostril, above the subject's lip.

For example, a respiratory device combining airflow through both nostrils is illustrated in FIG. 54. This device is configured for PEEP, and includes a hybrid flap valve 2501 and a biased rigid disc 2503. The device is shown inserted into both nasal passageways. During inhalation, the flaps 2501 of the flap valve move from a neutral position (B) to a flap open position (C) allowing air to flow from the outside environment into the nasal cavity with very low resistance. The rigid valve 2503 (to which the flap valve is shown attached) is biased against a valve seal (or seat) by a biasing element 2505. For example the biasing element may be a spring such as a compression or leaf spring made of metal or plastic. During expiration at low pressure, the device is sealed. At high expiratory pressures, the disc lifts, e.g., moving from the neutral position (B) to an open position (A), allowing airflow through the device. In this example, since the airflow into and out of the valve is centrally located, only one valve (e.g., one hybrid valve) is required, instead of one per nostril.

FIGS. 58 to 61 show additional examples of valves that may be incorporated into a PEEP configured device, because they can have resistance profiles similar to the resistance profile in FIG. 63, which has a low resistance to airflow during inspiration and a threshold for opening during expiration.

Figure 58:
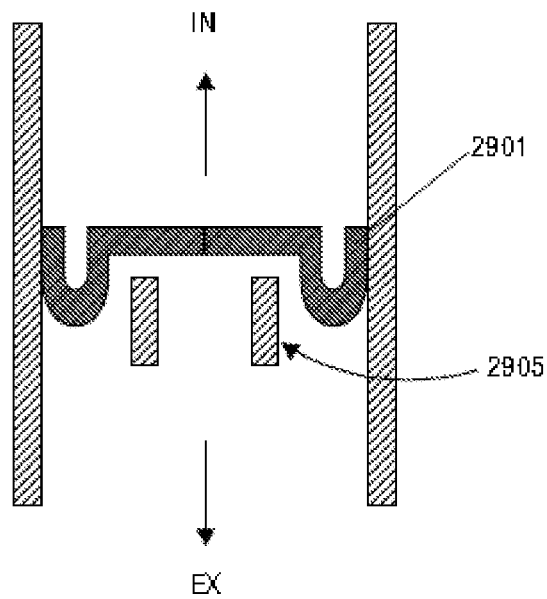
FIG. 58 shows a variation of an airflow resistor having a rolling hinge for use with any of the devices described herein.

FIG. 58 shows a valve having a rolling web or hinge. The valve is shown in the neutral position. During inhalation (indicated by the upward arrow), the pressure across the valve opens the flaps forming the rolling hinge 2901 allowing airflow with relatively low resistance. During exhalation, the flaps are closed, and the rolling hinge and flaps are propelled down (shown by arrow labeled "Ex") until the flaps contact the brace or braces 2905. When the pressure of exhalation exceeds the threshold for opening, the flaps bend to allow airflow across the valve. In some variations, the brace 2905 shown is not needed.

Figure 59:
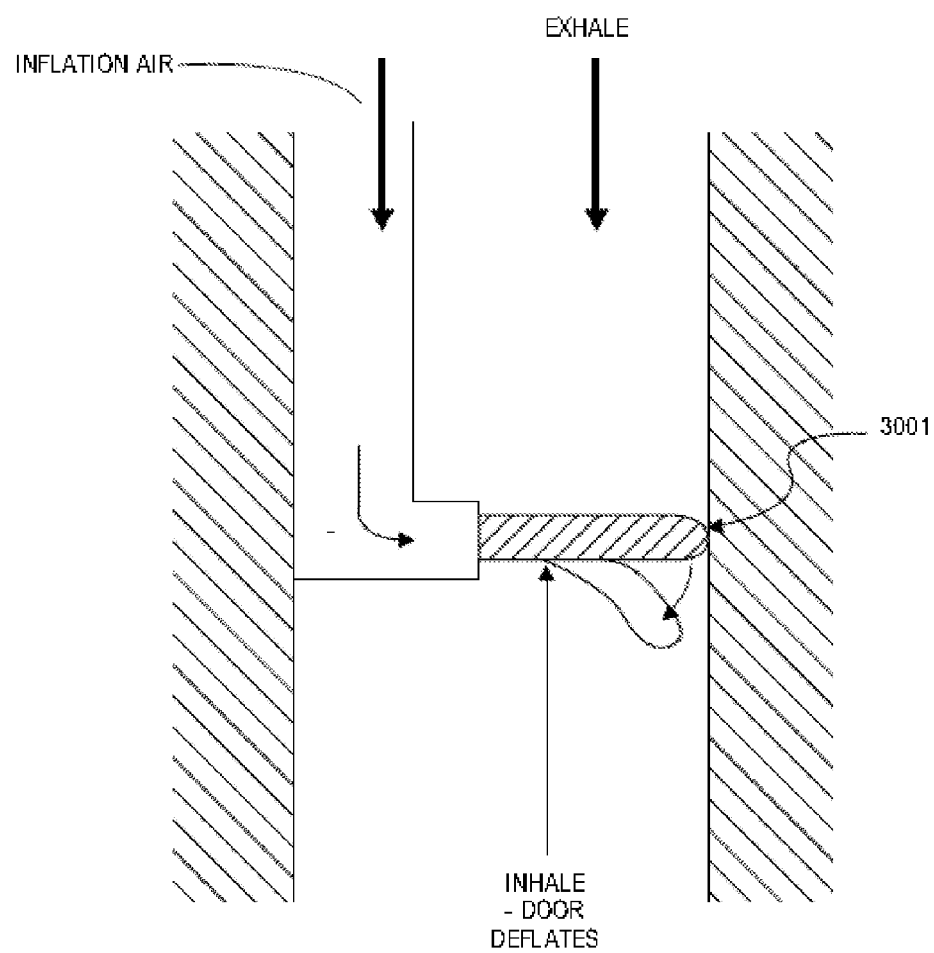
FIG. 59 shows a variation of an airflow resistor having an inflatable flap for use with any of the devices described herein.

The device shown in FIG. 59 includes an inflatable flap 3001 that is inflated during exhalation. During inhalation the flap is substantially un-inflated, and loose, and therefore readily moves to allow airflow. During exhalation, pressure from the distal end of the device (from a subject's lungs) moves down the passageway, and also down the inflation passageway shown on the left side of the passageway. Low pressure exhalation may be sufficient to inflate the bladder-like flap (which may comprise a thin elastomeric material, for example), causing it to extend across the passageway, preventing airflow. Although the flap is extended at higher pressure exhalation as well, at a threshold for opening, the pressure across the valve will cause the inflated flap to bend, allowing airflow with lower resistance. In some variations, the inflatable flap also includes a bias assisting it to inflate across the passageway.

Figure 60:
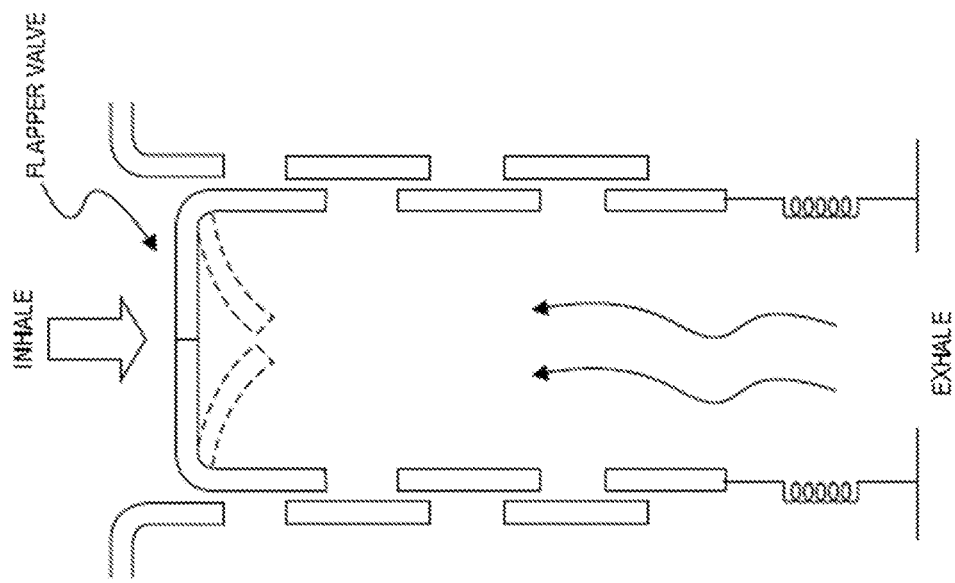
FIG. 60 shows another variation of an airflow resistor for use with any of the devices described herein.

FIG. 60 shows a valve device similar to the device shown in FIG. 46. The valve includes a combination flap valve (which opens during inhalation to permit airflow, but is closed during exhalation), and a sliding member attached to a bias. The sliding member includes holes along the sides. During low-pressure exhalation, the bias prevents the sliding member from sliding within the passageway. Higher pressure exhalation (e.g., pressure exceeding the threshold for opening) moves the sliding member up (as shown in the figure), allowing the holes in the sliding member to overlap with holes through the passage. Air may therefore flow through these holes to exit the device.

Figure 61:
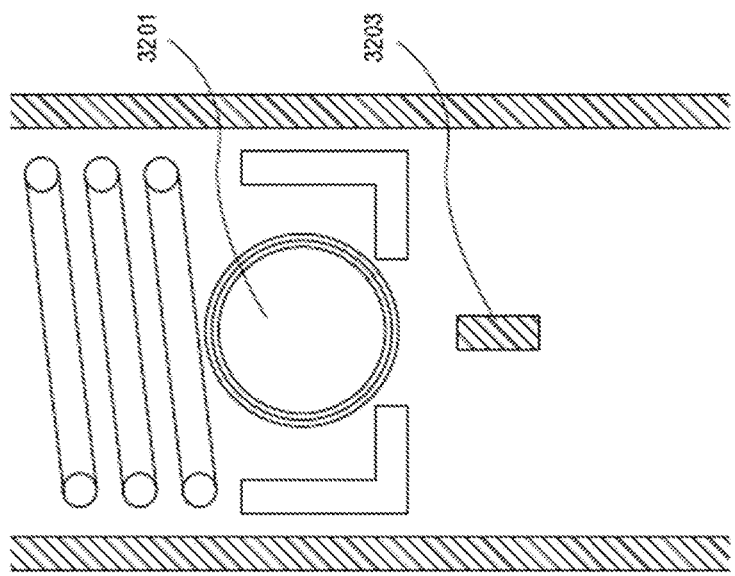
FIG. 61 shows a variation of an airflow resistor having ball valve and a slider, for use with any of the devices described herein.

Another variation of a sliding device is shown in FIG. 61. The PEEP device shown in FIG. 61 includes an airflow resistor that combines a ball valve with a biased slider. During inhalation the ball valve 3201 is displaced out of the way, permitting air to flow with low resistance through the passageway. During exhalation at low pressure, the ball 3201 blocks the opening in the passageway and the slider element is prevented from moving forward by a biasing element (shown as a spring in cross-section), so that there is little substantial airflow. At higher pressure exhalation (again, when the pressure across the valve exceeds the threshold for opening the valve) the slider moves against the bias towards the post 3203 in the central region of the passageway. The ball 3201 is eventually pushed out of the way by the post 3203 as the slider is pushed further forward, opening the passageway so that airflow may pass around the ball during high pressure exhalation.

Although these examples show airflow resistors including valves and devices that may be configured for use as a PEEP device having a resistance profile similar to the profile shown in FIG. 63, additional devices and variations of these devices may also be used. Furthermore, device having both a threshold for opening during exhalation, as well as a threshold for closing during exhalation may also be used. These devices may have a resistance profile similar to that shown in FIG. 35.

B. Differential Resistance Devices with a Threshold for Closing During Expiration Devices having both a threshold for opening during exhalation and a threshold for closing during exhalation may also be used as part of a PEEP device. In particular, these devices may include bistable valves. Bistable valves are valves that have more than one (e.g., two) 'stable' or neutral positions. Force or pressure may convert these devices between neutral positions. Thus, a valve may be configured with a bistable element so that the first stable portion regulates airflow during inhalation, and the bistable element in the second position regulates airflow during expiration. An example of this general concept is shown in FIGS. 62A-62D.

Figure 62A:
FIGS. 62A, 62B, 62C and 62D illustrate the operation of a bistable valve.
Figure 62B:
Figure 62C:
Figure 62D:

In FIG. 62A, a valve comprising a bistable flap is shown in the neutral position (e.g., between inspiration and expiration). The flap is shown as a curved surface. During inhalation, the curve may be further bent with very low resistance, so that airflow may occur during inhalation with very low resistance, as shown in FIG. 62B. During low pressure exhalation (shown in FIG. 62C), the flap remains in the curved position similar or identical to the position shown in FIG. 62A. Once the pressure increases to a predetermined point (e.g., the threshold for opening, the bistable flap opens, converting to a new stable position, as shown in FIG. 62D, opening to allow airflow therethrough. Once the flap is opened, however, it does not automatically return to the initial stable configuration (e.g., the neutral position shown in FIG. 62A or 62C). If the pressure across the valve falls below the threshold for opening. Instead, the flap may remain in the second stable position (e.g., open) until the pressure falls below a second threshold (e.g., the threshold for closing the valve during exhalation). As describe above, this relationship is described by a pressure profile similar to the on shown in FIG. 6.

Typical bistable elements include relatively stiff or pre-biased materials and shapes. For example, a pre-curved stiff metallic or polymeric material may be suitable as a bistable flap. FIG. 63 shows one example of a how a bistable flap may be easily produced. In FIG. 63, a cylindrical material is cut to form a flap for use as part of a bistable valve 3401. Any appropriate material may be used to form these flaps, particularly material having some inherent or structural stiffness.

Figure 45A:
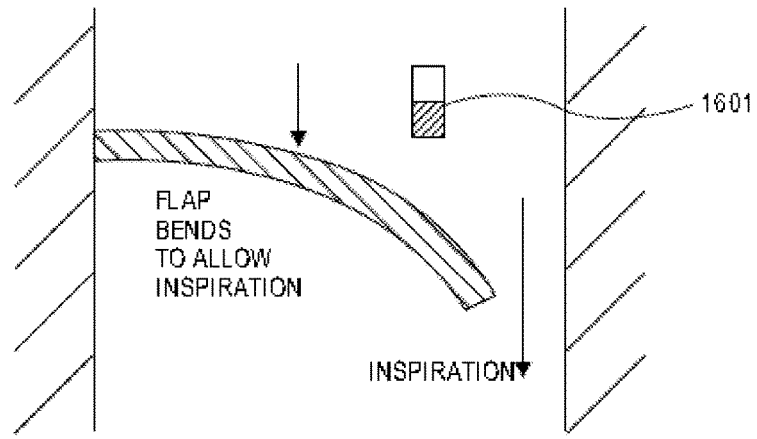
FIGS. 45A, 45B and 45C illustrate the operation of one variation of a device configured for PEEP.
Figure 45B:
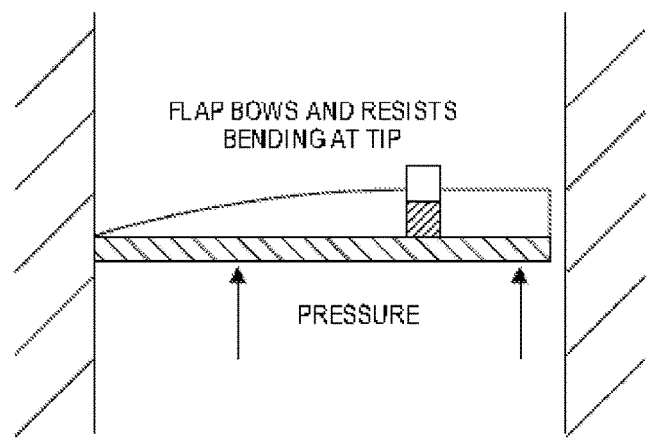
Figure 45C:
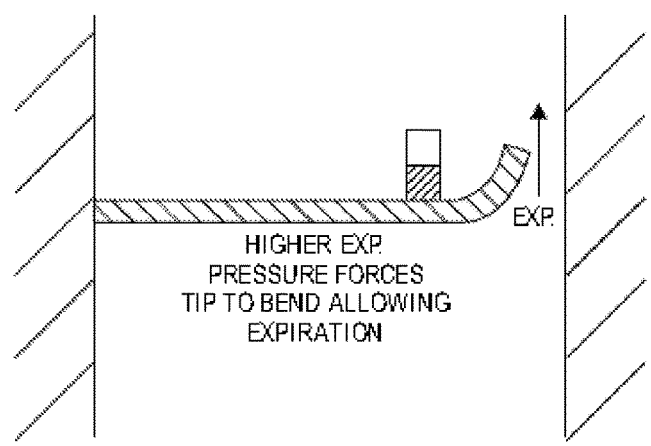
Figure 64:
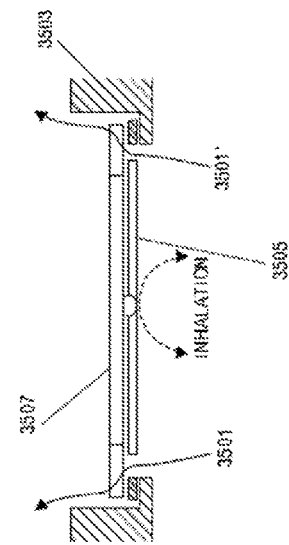
FIG. 64 shows a variation of a valve for use with any of the devices described herein.

A PEEP device may achieve a resistance profile similar to that shown in FIG. 64, when the valve includes a bistable flap. FIGS. 45A-C show one variation of such a device having a resistive profile similar to that shown in FIG. 64. The valve comprises a bistable flap that is free to open during inhalation (shown here in FIG. 45A as a downward bending). At rest the flap is flat. During exhalation at low pressure (up in FIG. 45B), the flap may have a curvature (somewhat like a fingernail) when it is forced against the crossbeam 1601 (also called a cross strut), as shown in FIG. 45B. During exhalation at low pressure (up in FIG. 45B), the flap valve is prevented from opening by both the crossbeam 1601 and because the flap has a predetermined stiffness. This stiffness may arise because of a combination of the material stiffness for the material from which the flap is formed (e.g., a stiff elastomeric material), as well as the shape into which the material is formed (such as a curved structure). Bistable shapes are described in greater detail below. In FIGS. 45A-45C, it is difficult to bend the region of the flap distal from the hinge region and the crossbeam. In order to open, the valve must bend over the beam as shown in FIG. 45C (shown as upward bending).

Figure 55:
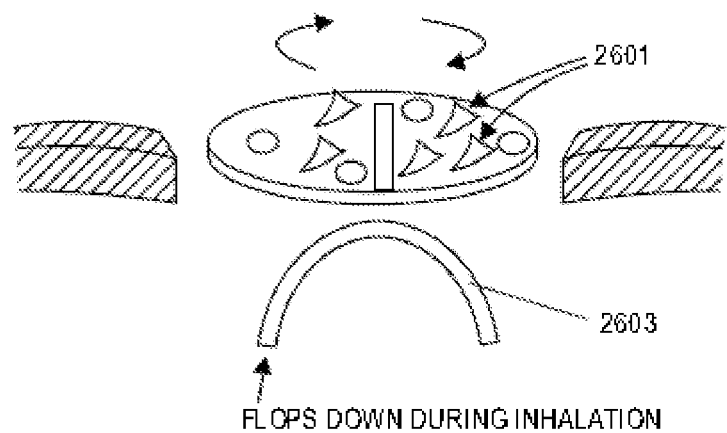
FIG. 55 shows another variation of an airflow resistor for use with any of the devices described herein.

In addition to bistable valves, other valves may also have both a threshold for opening during exhalation and a threshold for closing during exhalation. For example, FIG. 55 illustrates a valve that includes a flap 2603 that opens during inhalation allowing air to pass through holes on the plate 2601, and rotating the plate (configured as a disk) to move it down into a seal or seat. During exhalation, the flaps seal against the disk, and the pressure of the exhalation drives the disk 2601 to rotate in the opposite direction it rotated during inhalation. Rotation is driven by the high-resistance airflow passing along the edge of the disk or through channels on the disk. As the disk rotates it moves up (during exhalation, or down during inhalation). Once the disk reaches a predetermined height, the resistance to airflow during exhalation decreases, since air is allowed to pass around the sides of the disk more easily. Inhalation resets the disk by rotating it back down.

Figure 56:
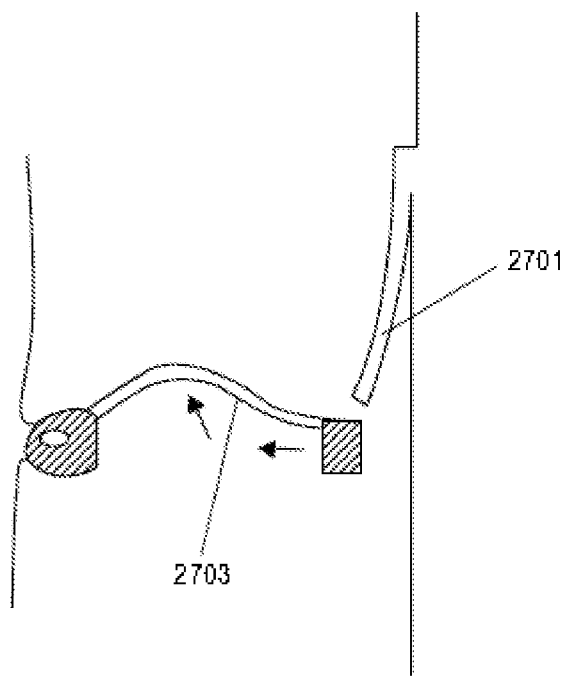
FIG. 56 shows another variation of an airflow resistor for use with any of the devices described herein.
Figure 65:
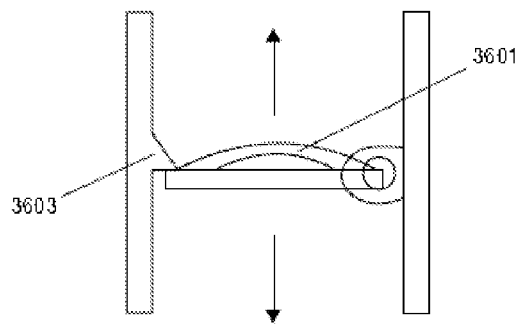
FIG. 65 shows another variation of an airflow resistor for use with any of the devices described herein.

FIG. 56 show a valve with a threshold for opening and a threshold for closing, and a profile similar to the resistance profile shown in FIG. 64. In FIG. 56, the valve is a flap 2703 that moves easily during inhalation to allow airflow at low resistance. The flap may be hinged at one end. In some variations, the flap is flexible (and may therefore bend over its entire length), while in other variations the flap is relatively stiff and bends most easily at the hinge region. During exhalation, the edge region of the flap is constrained from opening (e.g., in the upward direction in FIG. 56) by the rim or edge 2701 (e.g., shown as a projection 2701 in FIG. 56) along one side. When the pressure across the flap is strong enough to move the flap past this edge 2701 (the threshold for opening), the flap bends upwards, allowing flow across the valve. In the variation shown in FIG. 56, as the pressure across the valve during expiration falls, the edge of the flap contacts the rim 2701, again cutting off flow through the valve (at the threshold for closing). The valve is fully reset by inhalation, which may drive the valve flap behind the edge 2701 once again. Another variation of the valve shown in FIG. 56 is shown in FIG. 65.

Figure 57:
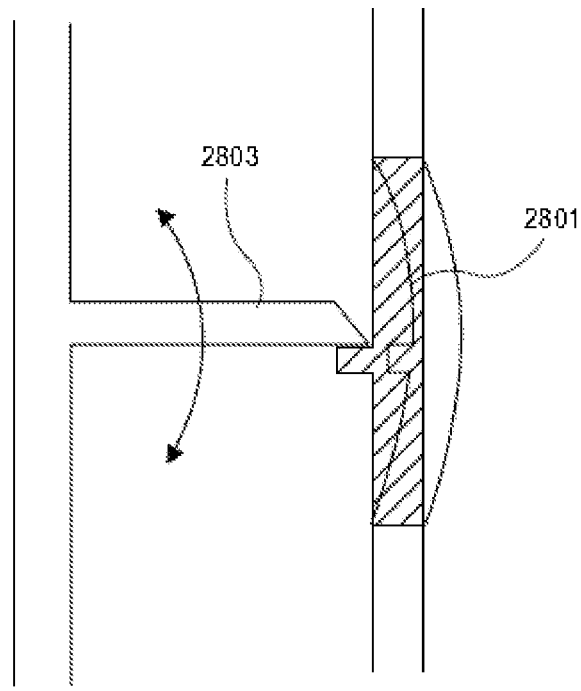
FIG. 57 shows a variation of an airflow resistor having an expandable wall for use with any of the devices described herein.

In FIG. 57, a flap valve 2803 is anchored to one side of the passageway. In this variation, the flap is relatively rigid (or stiff) across the length of the flap. The valve allows the passage of airflow with low-resistance during inhalation, because the flap moves upward, permitting air to pass. During exhalation at low pressure, the flap rest or is seated on a lip or rim on the opposite side of the passageway from where the flap is hinged. The portion of the passageway wall 2801 attached to this lip comprises a flexible or expandable material (e.g., an elastomeric material) and is configured to be unconstrained (e.g., not covered by a holdfast) so that the outside of the elastomeric region of the passageway 2801 is exposed to atmospheric pressure. As the pressure across the portion of the passageway wall 2801 increases during exhalation, the expandable region of the passageway 2801 is forced outwards, moving the lip or rim away from the flap, and permitting the flap to open (at the threshold for opening). Once the flap has opened, the flap will remain open even at relatively low pressures, unless there is an additional bias opposing the opening of the valve during expiration. If this bias is included (not shown), it would set the threshold for closing, as shown in FIG. 64. Otherwise, the valve would not be reset until inhalation drove the flap back past the lip or rim 2801. In this case, the resistance profile may resemble that of FIG. 65.

FIG. 64 shows another example of a valve having a threshold for opening and a threshold for closing during exhalation. In FIG. 64, the valve comprises a flap 3505 and a plate 3507. As described in many of the devices above, the flap valve opens with low resistance during inhalation so that air may flow through holes on the plate 3507 and thus through the device. During exhalation the flap closes, preventing substantial airflow through the holes. Instead, pressure across the valve pushes the rigid plate 3507 upwards. A similar design was seen for the valve in FIGS. 49A-49D, however the rigid plate in that valve was biased to prevent movement at low pressure during exhalation. In FIG. 64, the rigid plate includes an adhesive or magnetic force that must be overcome before the plate can be moved upwards, allow airflow though the device. FIG. 64 shows a magnetic or otherwise adhesive region 3503 between the rigid plate 3507 and the lip or seal region of the device on which the rigid plate 3507 rests. During high-pressure exhalation the adhesion (e.g., magnetic adhesion) between the plate and the rim is ruptured, allowing the plate to move upwards, opening a low-resistance pathway for airflow 3501, 3501'. This device may have a resistance profile similar to the profile shown in FIG. 65, for example.

Time Dependency of the Device

As mentioned briefly above, the devices described herein may also be configured to have a time-dependent response. For example, it may be desirable to delay the response of the change in resistance based on the time point of the respiratory cycle. In one variation, a PEEP device may delay closing the valve after switching from inhalation to exhalation, even though the respiratory pressure is relatively low across the valve. Delaying switching to high resistance may allow the user to accommodate to the device more easily, enhancing comfort, and possibly aiding with compliance. In some variations, the devices described herein are configured so that airflow through the device is not substantially inhibited until some set time (e.g., less than 0.1 sec, less than 0.2 sec, less than 0.3 sec., less than 0.5 sec., less than 1 sec., etc.) or some percentage through a portion of the respiratory cycle. For example, the device may not provide a high resistance to low-pressure exhalation until approximately one-third or halfway through the expiration cycle (or 5% through the expiration cycle, 10% through the expiration cycle, 15% through the expiration cycle, 30% through the expiration cycle, 40% through the expiration cycle, 50% through the expiration cycle, 60% through the expiration cycle, 70% through the expiration cycle). The expiration cycle may be determined individually for a particular user, or an average (e.g., population) expiration cycle may be determined.

A respiratory device having a time-delay for the onset of resistance to low-expiratory pressure may include electronic (e.g., timing) components, including counters, clocks, sensors and the like. In some variations, a respiratory device includes a non-electronic timer, such as a mechanical delay which is initiated upon a change in the direction of airflow from inspiration to expiration. For example, a mechanical delay may comprise a dashpot or damper which prevents one or more of the valves within the device from closing after inhalation. The damper may include a pre-set delay before closing completely. In some variations, opening is substantially undampened.

Operation of the Respiratory Device

The airflow resistor may be oriented in any direction. In one variation, a respiratory device may be used in one nostril in an opposite orientation to a respiratory device in the other nostril, which may alternate through which nostril resistive inspiration or expiration occurs.

In some versions, the respiratory device is shaped so that the direction of the airflow resistor is immediately evident. For example, the respiratory device may be of a different shape or size on one end, or may include a visual indication. In one version, the respiratory device may be shaped so that it fits securely into a respiratory orifice only in one orientation (e.g., so that the airflow resistor inhibits the expiration more than it inhibits inhalation). For example, a flange or other mechanical stop may be used to insure proper orientation, while simultaneously preventing migration of the device further into the respiratory orifice.

In many embodiments, the PEEP-configured device provides some level of resistance to expiration, particularly at low pressure. It may be preferable to have little if any effect on resistance to inspiration, though in some cases, some degree of inspiratory restriction may be beneficial. In some versions of the device, both inspiration and expiration may be inhibited by the airflow resistor.

The device may also be adapted for comfort. Any device placed either in or around the oral cavity or in or around the nose should not be painful, and if possible not very noticeable by the patient. Thus, the holdfast may be shaped to conform to the attachment site in or around the respiratory orifice. In some versions, the holdfast comprises a flexible or shapeable material (e.g., a foam or other soft shape-memory material). In some versions, the entire respiratory device comprises a soft material.

When using devices that feature a foam on the portion of the device that fits within or otherwise communicates with the inside of a nostril, the device may be inserted by the patient or healthcare provider foam end first. It may be helpful to insert a corner of the device into the nostril and then rotate the device into place. The device may then be gently pulled outward (without removing the device from the nostril) so that it rests in the correct position and provides a seal between the periphery of the device and the nasal cavity or nostril.

The user may be instructed to breathe through his/her/its mouth or nose, whichever is more comfortable. If the device is going to be worn by a subject during sleep, the user may be instructed to breathe primarily or relatively primarily through his mouth while he is still awake. This may make the sensation of expiratory resistance and pressure easier to tolerate. It is expected that when the patient goes to sleep, he will revert primarily or at least partly to nose breathing, thus promoting the beneficial effects of the device. The subject devices may also be used with any commercially available device that promotes closure of the mouth during sleep, including but not limited to straps, mouth guards, tape and the like.

In some cases, a nasal cannula or other means of monitoring nasal airflow (such as a thermistor) may be attached, fixed, or non-fixably positioned within or near the device to allow various diagnostic parameters to be measured. In some cases, the nasal cannula or other diagnostic device may be held in place with tape (on the face for example, near the chin or cheek). By attaching the diagnostic device to the device, it is less likely that inadvertent or undesired motion will shift or displace the device while sleeping or otherwise during use. In some cases, the subject device may be extended or otherwise altered or changed to allow the placement of the nasal cannula.

In other cases, an intranasal pressure probe or sensor may be placed beyond the device (deeper within the nasal cavity or nostril) to provide a pressure reading for the airways, nose, and other respiratory pathways.

Furthermore, the device may be adapted so that it is more or less visible to others. In some cases, the device may be configured to be placed high enough within the nostrils to make it difficult for others to see. Furthermore, the device may be of any color and/or pattern that help to camouflage it. In other versions, it may be useful to include colors and patterns that stand out, including ones that are fluorescent or otherwise offer increased visibility during the night or other setting where ambient light is reduced.

In some versions, the respiratory device may be "one size fits all", so that it may be used with any patient (or any patient of approximately the same size), despite differences in shapes and sizes of their nose/nostrils, oral cavity, teeth and other relevant anatomic features. In one version, the devices may conform to a range of sizes, for example "small," "medium," and "large" (or any other appropriate range, such as, e.g., a numerical range). Alternatively, the devices may involve a custom fit of the device or devices to the patient.

Custom fitting may improve patient comfort and potentially improve performance by improving the seal between the device and the patient's oral cavity, mouth, nasal cavity and nostrils, for example. In some versions, custom fitting may involve the placement of a device in warm or cold liquid or air with subsequent placement in the patient's nose or mouth. This process is meant to "prime" the materials in the device (e.g., particularly the materials of the holdfast), so that when the holdfast is secured to the patient, the device permanently assumes a shape or configuration corresponding to a portion of the patients anatomy.

In some cases, the device may be over the counter (OTC) and in other cases, it may require a prescription. Some possible indications for the device will include but not be limited to sleep apnea, snoring and upper airway resistance syndrome. In other cases, the device may be used to improve athletic performance, heart or lung function, or improve oxygenation. In some cases, the devices will be reusable. In some cases, the devices will be disposable after one or more uses. The devices may be modular; for example, at least one component or subassembly of the device may be reusable and at least one component or subassembly may be disposable.

In some version of the devices described herein, an airflow resistor may fit within a larger structure (such as the passageway) so that some airflow through or around the airflow resistor is always allowed. For example, there might be a constant opening between the airflow resistor and the anchor that secures the airflow filter in communication with the passageway. This may ensure that expiratory and/or inspiratory airflow is never completely occluded. In some versions, the airflow resistor comprises a "hole" or opening. As described above, the device may include one or more holes or air leak paths even in the closed position, so that some air may pass through the device even if the holdfast forms a relatively tight seal with the nasal cavity. For example, the airflow resistor (e.g., flap valve) may include one or more holes providing an air leak path. The size of the holes may be configured to allow a predetermined rate of airflow through the holes when a certain pressure is applied (e.g., by the user's breathing). For example holes may be small (e.g., having diameters of 0.030 inches±0.010 inches). In some variations, multiple holes are used.

The devices described herein may create a PEEP effect by differentially changing the resistance to airflow in one direction based on the pressure applied against the device, as described above. For example, in some designs, expiratory airflow is subjected to resistance by the airflow resistor (or valve) until a certain threshold pressure differential or level of airflow is achieved; below that threshold, a more complete closure of the airflow resistor occurs (potentially completely occluding airflow through the device). The desired levels of PEEP are on the order of about 0.1 to about 30 cm H2O and more preferably about 1 to about 15 cm H2O pressure. Similarly, the differential resistance may also be triggered at very high pressures across the valve. For example, above a typically high threshold of pressure or level of airflow, the airflow resistor (e.g., valve) may open to decrease the resistance due to the airflow resistor, as when a patient coughs, sneezes, or blows his or her nose.

In some cases, the device may offer a variable resistance that is lower during the start of expiration (to promote comfort and tolerance) and that continues to increase (in a stepwise or more gradual fashion) for the remainder of expiration. In many cases, at the end of expiration, PEEP will be maintained. In still other cases, there will not be PEEP at the end of exhalation. In some respiratory devices described herein, when expiratory airflow and/or expiratory airway pressures fall below a threshold (one that is too low to keep an airflow resistor mechanism open), expiration airflow will be stopped, leading to PEEP. As a result, normal inspiration, normal expiration, and PEEP are accommodated while offering potential benefits to the patient, including clinical benefits.

In some cases, the device may feature a fixed orifice during expiration (e.g., a fixed leak path). Thus, the size of the hole(s) within the airflow resistor remains substantially or significantly equal for all, most or substantially most of the expiratory cycle. Such a device may allow the "average" and peak pressures in the airway to be different during supine positioning, lateral (left or right) positioning and prone position during sleep. Preferred peak airway pressures during exhalation, regardless of positioning, may be between 0.1 to 70 cm H2O, more preferably between 0.5 and 25 cm H2O and most preferably between 1 and 20 cm H2O pressure during sleep. Supine pressures may on average be greater than pressures while in lateral and prone positions during sleep.

The optimal level of expiratory resistance or PEEP provided by the device may vary from patient to patient. In some versions, adequate expiratory resistance or PEEP is created to offer the desired benefits, but not providing too much expiratory resistance or PEEP so that the patient preferentially begins breathing (e.g., inspiring and/or expiring) through the mouth. In some cases, the user may test the device or devices while being monitored by a healthcare provider, a camera, a polysomnograph, or any other device that will help to assess the optimal level of resistance or therapy provided by the subject devices. As described in more detail below, the devices described herein may be adjustable. In particular, the threshold pressure for opening the valve during exhalation may be adjustable, for example by the subject or a healthcare provider. In some variations, the threshold pressure for closing the valve may also be adjustable, for example by the subject or a healthcare provider.

The use of an airflow resistor may also alter the inspiratory time:expiratory time ratio (I:E ratio), which is defined as the ratio of inspiratory time to expiratory time. The desired I:E ratio will be between about 3:1 and about 1:10 and more preferably about 1:1 to about 1:4 depending on the needs of the individual patient. In some versions, the desired ratio is approximately about 1:2.

In some versions, the device comprises an insertion, adjustment, or removal mechanism. In some cases, this mechanism involves any appropriate rigid or non-rigid positioner that facilitates removal or positioning of the device. Non-rigid positioners include but are not limited to cables, chains, wires, strings, chains, sutures, or the like. Rigid positioners include knobs, handles, projections, tabs, or the like. A user may grasp or otherwise manipulate the positioner to facilitate insertion, re-adjustment, or removal of the device. Furthermore, various applicators or other insertion devices may be used. For example, a tubular applicator holding a respiratory device adapted for insertion into a nasal cavity may be advanced into the nasal respiratory orifice (e.g., nostril) to insert the respiratory device.

In some cases, the device may be oversized, or larger than the cavity it is inserted into, for example to prop open the nasal valve. Oversizing the device may reduce resistance in one or more direction of airflow. In some versions, the passageway through the device is oversized. In some versions, an outer portion of the device that contacts the respiratory orifice is oversized. Thus, the respiratory device may exert pressure against the nasal cavity of a user. In patients with obstructive sleep apnea or snoring, for example, increasing the size of a respiratory device configured to be inserted into one or more nostrils may prevent the more distal tissues of the airway, tongue, and nasopharynx from being sucked in or closed during inspiration. Moreover, airflow through an oversized passageway may assume a less turbulent flow profile, resulting in a decreased propensity for noise production in the case of snoring, for example. Similarly, the respiratory device passageway may be shaped so as to decrease turbulence of airflow. Likewise, the shape and activity of the airflow resistor may be chosen to minimize turbulence and, therefore, sound or vibration.

In operation, the user may be asked to clean his or her nose, trim or clip his or her nose hairs, and remove all or substantially all nasal mucus or boogers. The device, especially if it is at least partly composed of foam or other deformable material, may be squeezed to reduce its size prior to insertion into the nasal cavity or nostril. In some cases, the deformable material may expand or swell over time, providing a comfortable fit and/or seal. In some cases, water or water vapor may facilitate or expedite said swelling or increase in size. In some cases, water or other liquids may fill in holes within open cell foam, therefore improving seal.

In some cases, an active or inactive ingredient may be added into (or onto the surface of) at least one component of the device. For example, an odorant such as menthol, phenol, eucalyptus, or other fragrance may be used. Alternatively, a lubricant or moisturizer (on the surface of the holdfast, for example) or the like may find use to improve patient comfort, seal, etc. Any commonly or uncommonly used substance or ingredient that is used in over-the-counter and/or prescription healthcare products may find use.

The respiratory devices may be manufactured and assembled using any appropriate method. Representative manufacturing methods that may be employed include machining, extruding, stamping, and the like. Assembling methods may include press-fitting, gluing, welding, heat-forming, and the like.

A holdfast may be attached to the outer portion of the tubular body, particularly the distal region of the tubular body. In many of the exemplary devices described herein, the holdfast is polyurethane foam. The foam may be pre-molded into the appropriate shape, or it may be cut (e.g., die cut, water jet cut, laser cut, etc.) into a ring or other appropriate shape and attached to the tubular body. For example, the foam may be attached via an adhesive (e.g., tape, glue, etc.). In one variation, the foam is cut from a strip of foam that is attached around the tubular body. The foam may be any appropriate size so that the device is secured within a subject's nasal cavity. In some variations, the foam is between about ¼ and ⅛ of an inch thick. The thickness of the foam holdfast may vary around the diameter of the device. For example, the foam holdfast may be thicker at the ends of an elliptical cross-section so that it conforms better to the shape of a subject's nasal cavity, particularly in the region immediately within the subject's nose, past the nares.

Figure 66:
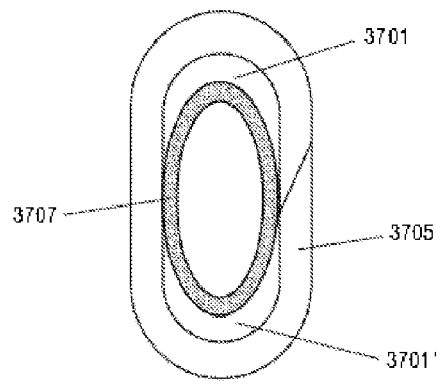
FIG. 66 shows a cross-section through the holdfast of a device as described herein.

FIG. 66 shows one variation of a foam holdfast attached to the outer surface of distal region of the tubular body 3705. The holdfast in FIG. 66 includes two regions that are applied with adhesive. The first region 3701 includes the two narrower ends (e.g., shown as the upper and lower ends) of the tubular body cross-section. In some variations, tapered strips (e.g., cut to be approximately 0.22 inches wide, by approximately 0.6 inches long) are attached at these narrow ends, and then a third strip (approximately 0.22 inches long) is applied on top of them, as shown in FIG. 66. The outer strip 3705 is then trimmed to create a relatively smooth outer surface. This configuration augments the ends of the valve body, which may provide a better nostril fit and seal. In some variations, the outer diameter of the tubular body may also be adjusted (e.g., to make the two end foam pieces 3701, 3701' unnecessary, for example).

As described above, any appropriate foam may be used. For example, Microbaisan 100 foam produced by Lendell Manufacturing is a medical-grade, biocompatible sponge foam that may be used. This foam has a relatively low air permeability.

The holdfast may be adjustable by a practitioner or the user, so that it more comfortably and/or securely fit a particular user. For example, in variations for use within a user's nasal cavity, the holdfast may consist of selectively removable layers of foam that may be removed (e.g., onion-skin like) until a comfortable size is achieved. In some variations, the layers may be coded (e.g., color coded, numbered, etc.) to indicate each "level" of holdfast. Thus, once a user determines a particular configuration for the holdfast that comfortably fits his nose, he may easily set each subsequent device to that configuration.

Figure 67:
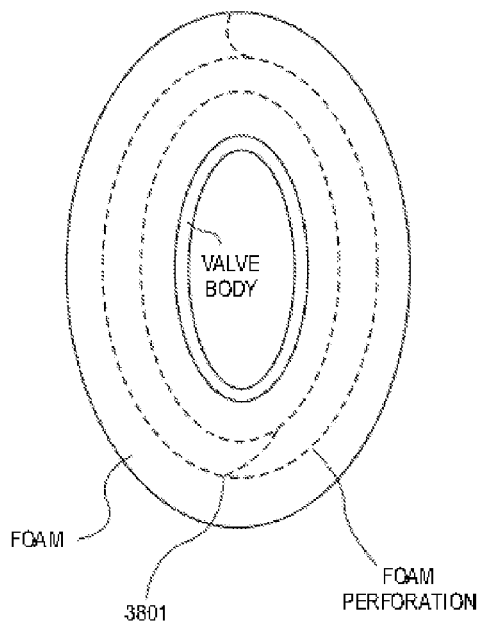
FIG. 67 shows one variation of an adjustable holdfast, as described herein.

FIG. 67 illustrates one variation of an adjustable holdfast, as described herein. In FIG. 67, foam surrounds the outer surface of the tubular body. The foam is divided up into layers, as shown by the dotted lines. Layers may be formed either by applying the foam in layers, or by cutting a relatively thick layer of foam into different layers 3801 (e.g., perforating the foam by laser, etc.). Thus, the shape of the holdfast can be changed by removing one, a portion of one, or multiple layers of foam from the device. For example, in FIG. 67, the outermost layer of foam may be removed by peeling the layer off in a clockwise direction, and the second layer may be removed by peeling the layer off in a counterclockwise direction. Changing the direction of removing each layer may prevent unintentionally removing too much of the holdfast.

Figure 68A:
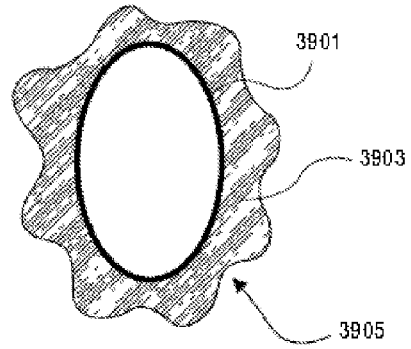
FIGS. 68A and 68B show cross-sections through a holdfast of a device configured for use within a subject's nose.
Figure 68B:
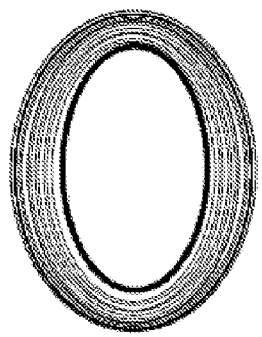

The holdfast may also be configured to expand to fit within the subject's nasal cavity. Nasal tissues may swell during sleep or when a subject is lying prone. This swelling may allow the user to insert a respiratory device that is relatively loose fitting before lying down, permitting easier breathing. Thus, before a subject falls asleep the more loosely fitting device can help the user breath more easily, and any nasal swelling that occurs would gradually help the subject sleep better. FIGS. 68A and 68B illustrate a device configured to take advantage of this swelling.

In FIG. 68A, the holdfast 3903 surrounds the outer surface of the passageway-forming body 3901, and consists of a soft, biocompatible material that has a scalloped shaped profile. When the device is inserted into a subject's nostril, there may initially be gaps 3905 that form between the holdfast and the walls of the subject's nasal cavity. As the walls of the nostril swell (e.g., during sleep, etc.), and the inner diameter of the nostril decreases, these gaps may disappear, so that the device is comfortably sealed within the nasal cavity, as shown in FIG. 68B. Swelling and reduction of the inner diameter of the nostril may also compress the holdfast (e.g., a compliant foam holdfast), advantageously reducing the air permeability of the holdfast.

In some variations, the foam may be configured to expand within the nasal cavity. As mentioned briefly above, the foam may be configured to swell because of the increased moisture (e.g., in exhaled air), thereby enhancing fit or the seal within the nasal cavity. In some variations, the holdfast is configured to expand in the presence of the subject's body heat. Thus, heat transfer from the subject to the device causes the holdfast to swell and thus better fit the nostril.

Although most of the devices described herein are configured for nasal use, devices may also be configured for oral use (e.g., within the oral cavity). For example, an oral device for inducing positive end-expiratory pressure may be secured in communication with an oral cavity (e.g. over, at least partially over, within, or at least partially within the subject's mouth) and may include a passageway, an airflow resistor in communication with the passageway, wherein the airflow resistor is configured to have a non-zero threshold pressure for opening during expiration so that the airflow resistor is closed during expiration when the pressure across the airflow resistor is below the threshold pressure for opening, but the airflow resistor opens during expiration when the pressure across the airflow resistor exceeds the threshold pressure for opening during expiration; and a holdfast configured to secure the airflow resistor in communication with the oral cavity but not the subject's nose in some cases.

In some variations, the holdfast is configured as a mouthpiece that fits at least partially within the subject's mouth. An oral respiratory device may extend the jaw (e g, mandible) and/or the tongue to further facilitate respiration. These oral respiratory devices may also include one or more valves to help regulate respiration. In general, these devices may fit within or partially within the subject's oral cavity and displace or extend the subject's mandible and/or tongue, as well as provide a pathway for airflow that may be regulated by one or more valves or airflow resistors. Any portion of the device may also extend out from the subject's oral cavity.

Figure 69:
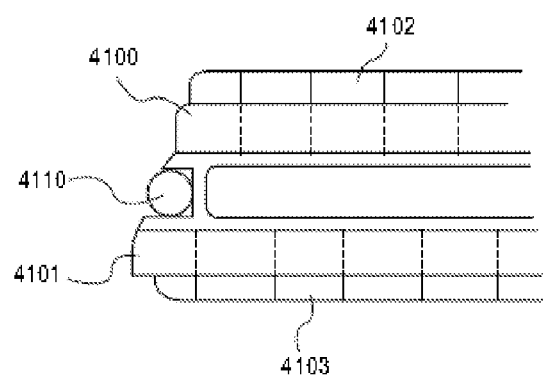
FIG. 69 shows one variation of an oral device including mandible displacement, as described herein.

FIG. 69 shows one variation of an oral device that may allow the benefits of expiratory resistance (with or without PEEP) in addition to the benefit of advancing the mandible (which increases the size of the upper airway). Upper jaw anchor 4100 and lower jaw anchor 4101 serve to secure the device to the upper jaw 4102 and lower jaw 4103 respectively in such a manner that the lower jaw 4103 (mandible) is pushed forward while slightly opening the jaw. The device offers an opening in or around the space between the jaws through which air may flow, and a resistor 4110 may be placed in this location. At least some of the subject's airflow must pass through the resistor in one or more directions. Any resistor, including those described herein, may be used, including resistors that offer preferential expiratory resistance, with or without PEEP. Examples of additional airflow resistors that may be used with this device are included in U.S. patent application Ser. No. 11/298,640, filed Dec. 8, 2005 and U.S. Provisional patent application titled "NASAL RESPIRATORY DEVICE," filed May 23, 2006, each of which was previously incorporated by reference in its entirety. The device may be made of any appropriate hard or soft materials, including those described herein. In some variations, the degree of lower jaw advancement may be adjusted.

Figure 70:
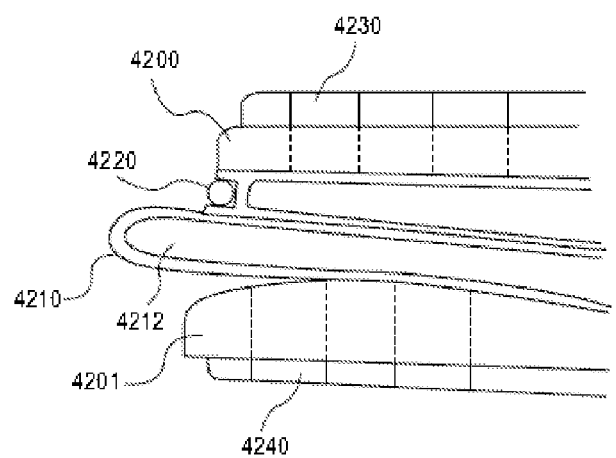
FIG. 70 shows another example of an oral device as described herein.

FIG. 70 shows another variation of an oral device that may provide expiratory resistance (with or without PEEP) and may advance the tongue to an anterior position (which increases the size of the upper airway) through the use of suction. In FIG. 70, upper jaw anchor 4200 and lower jaw anchor 4201 serve to secure the device to the upper jaw 4230 and lower jaw 4240 respectively, and suction cavity 4210 is positioned between jaw anchors 4200 and 4201 to receive and retain the tongue 4212 during use. Thus, the tongue may be pulled (via the suction) toward the anterior direction (e.g., out of the mouth). The device may have an airflow opening at any location between jaw anchors 4200 and 4201, where resistor 4220 may be positioned. At least some of the subject's airflow must pass through the resistor in one or more directions. Any appropriate resistor may be used, including those described above (e.g., resistors that offer preferential expiratory resistance, with or without PEEP). The device may be made of any appropriate materials, particularly those suitable for oral use, including hard or soft materials. In some embodiments, the devices in FIG. 69 may be coupled with some lower jaw advancement as described in FIG. 70.

In some variations, it may also be desirable to occlude the nostrils of a user wearing an oral device (including the mandibular or tongue displacement devices described above). Thus, a second device may be used in conjunction with an oral device to plug the nose so that airflow is restricted to the mouth. In some variations, the oral device may include a nostril-occluding region integral to the oral device. Restricting airflow to the subject's mouth may enhance the effects of any of the various oral resistance devices (with or without PEEP) described herein.

Uses of the Respiratory Devices

The respiratory devices and methods described herein may be used for a variety of therapeutic and non-therapeutic purposes, particularly uses in which PEEP would be helpful. A description of some of these uses is given below. The respiratory devices and methods described herein may be used in other ways as well, and these examples are not to be considered exhaustive.

Generally, the respiratory devices described herein may improve the respiratory and cardiovascular function of a person in need thereof (e.g., a patient). Thus, these respiratory devices may be used therapeutically, for example, to cure, treat or ameliorate the symptoms of a variety of medical disease states. Furthermore, the respiratory devices may be useful in generally improving the health and well-being of any person.

Disease states which may be treated by the devices and methods described herein include but are not limited to: heart failure (right-sided and/or left-sided), COPD, pulmonary edema, sleep apnea (obstructive and/or central), sleep-disordered breathing, Cheyne-Stokes respiration, insomnia, snoring and other sleep disorders, asthma, bronchomalacia, acute lung injury, ARDS, cystic fibrosis, hypoxemic respiratory failure, gastroesophageal reflux disease, hiatal hernia, heartburn, hypertension, myocardial infarction, arrhythmia, cardiomyopathy, cardiac valve disease (either stenosis or regurgitation of the mitral, aortic, tricuspid, or pulmonic valves), stroke, transient ischemic attack, increased cerebral pressure, a variety of inflammatory diseases, and degenerative neurologic conditions. Moreover, the devices may be beneficial for patients being weaned off mechanical ventilation, as well as post-operative patients.

The increased pressure within the airways may reduce the amount and frequency of pulmonary edema, a common consequence of heart failure. Afterload and preload on the heart may also be affected; for example, afterload and preload may be decreased in patients with heart failure. Filling pressures may be increased or, more likely, decreased. Decreasing filling pressure may potentially benefit patients with failing hearts. Gas exchange may improve in many cases, leading to increases in $pO_2$ and decreases in $pCO_2$. In some cases, the level of $pCO_2$ may actually increase or become more stable and less likely to fluctuate. This increase in the stability of $pCO_2$ levels may lead to profound benefits in patients with central sleep apnea and in patients with Cheyne-Stokes breathing, for example. Oxygen saturation levels may improve. Oxygen desaturations which may result from apneas or hypopneas may no longer drop as far. For example there may be fewer oxygen desaturations to the 80-89% range. Fewer oxygen desaturations may drop below 90%. Duration of desaturations may also be reduced. The use of the device to reduce oxygen desaturations (perhaps leading to performance enhancement) while awake or asleep may represent a viable market opportunity for the device.

In some cases, the use of a expiratory resistor will interfere with loop gain, and will thus promote more stable breathing. In other cases, the device will reduce the amplitude, duration, and frequency of snoring.

Any location within the body that is exposed to respiratory airflow (including but not limited to the upper airway, trachea, bronchi, nasopharynx, oropharynx, nasal cavity, oral cavity, vocal cords, larynx, tonsils and related structures, back of the tongue, sinuses, and turbinates) may benefit from the increased airway pressure and increased duration of expiratory airflow. In some cases, there will be a reduction in swelling and edema in these locations, leading to increased diameters of the airways and conduits in which the airflow passes. This leads to less of a tendency for these structures to collapse upon inhalation. Moreover, these structures may be less prone to create noise on inspiration or expiration, thereby reducing the quantity and/or quality of snoring. Put another way, the reduction of edema in the airways may make it less likely that these structures will collapse and may reduce the volume and frequency of snoring, apnea, or hypopnea. Furthermore, reduction in swelling and edema and improved lymphatic flow due to these positive pressures may reduce nasal congestion, inflammation, and sinusitis for example.

The respiratory device may also increase lung compliance. For example, lung compliance may increase partly if fluid which might otherwise be in the lung and alveoli is driven away by the increased airway pressure. This increased lung compliance may make it easier to breathe and may require less effort and force on the part of the patient to displace the diaphragm a certain distance to achieve a certain tidal volume. Moreover, increased lung compliance may decrease the pressure differential between the alveoli and mouth. As this pressure differential decreases, it becomes less likely that an inhalation attempt will induce a collapse of the upper airway. Thus, an increase in lung compliance may herald a reduction in the frequency or severity of obstructive sleep apnea or hypopnea episodes. Similarly, snoring frequency and severity (volume) may be reduced for similar reasons.

The respiratory device may also improve ejection fraction. This effect may be mediated via increases in intra-thoracic pressure and alterations in transmural pressures and the beneficial effects on preload and afterload on the failing heart. In addition to left-sided benefits to the heart, there may also be benefits afforded to the right side of the heart. Improving ejection fraction with the respiratory devices described herein may result in positive short- and long-term changes to the energetics and biologic properties of the heart tissue. Some of these positive changes may mimic the positive remodeling changes seen in hearts treated with various complicated cardiac support devices such as those developed by Acorn Cardiovascular (St. Paul, Minn.) and Paracor Medical (Sunnyvale, Calif.). These expiratory resistors use the patient's own intra-thoracic pressure to "support" the patient's heart. Moreover, because the support potentially provided by the respiratory devices described herein is not limited to just the ventricle, it may support the atria, which can also be severely affected by heart failure and other cardiac or pulmonary diseases. There may be reductions in left ventricular and left atrial sizes, both in the shorter and longer term. Furthermore, cardiac sympathetic activation may be reduced, and cardiac output may be increased or decreased depending on the nature of the resistance provided.

There are a variety of other beneficial effects of enhanced expiratory resistance and increases in intra-thoracic pressure that may be achieved with the respiratory devices described herein. Examples include decreased heart rate and blood pressure. There may be a reduction in the number of arrhythmias, including but not limited to atrial/supraventricular and ventricular fibrillation, atrial/supraventricular and ventricular tachycardias, heart block, and other common arrhythmias. Thus, the respiratory devices described herein may also reduce the incidence of sudden cardiac death and other cardiac disorders. Furthermore, coronary perfusion may be expected to increase. Further, expiratory resistance and increased intra-thoracic pressures may lead to improvements in gastroesophageal reflux disease (i.e., heartburn), gastritis, Barrett's esophagus, esophageal cancer, hiatal hernia, and other causes of diaphragmatic hernia. This effect may be mediated by the compression of the esophagus located within the thorax due to the increased intra-thoracic pressures. As a result, food and other stomach contents may no longer be able to reflux superiorly into the esophagus, which is otherwise common when patients are lying down. Furthermore, hernias (primarily hiatal) may be reduced and pushed back into the abdomen by the increased intra-thoracic pressure. The use of these respiratory devices may have beneficial effects on other gastroenterologic conditions beyond those already described.

Cardiac valve disease, including but not limited to mitral, tricuspid, pulmonic and aortic regurgitation, and mitral, tricuspid, pulmonic and aortic stenosis may also benefit from the respiratory devices described herein. In particular, the respiratory device may affect mitral regurgitation and may help prevent further annular dilatation (a byproduct of heart failure and generalized heart dilation).

Use of the respiratory devices described herein will result in a reduction in respiratory rate, which may be very helpful in diseases such as COPD, asthma, hyperventilation, and anxiety disorders including panic attacks, among others. The ratio of inspiratory time to expiratory time (I:E ratio) may be decreased with the device. Tidal volumes may increase as well. For example, in COPD, the increased resistance may facilitate improved expiratory function. This may also allow the patient to benefit from larger tidal volumes and increased minute ventilation. In still other cases, respiratory rate may be increased and in other cases, minute ventilation may be decreased.

The amount of PEEP (or resistance generated by the device) may overcome some, or all, of the intrinsic PEEP that is common in patients with COPD. In patients with COPD or other pulmonary disorders, or even patients without disease, gas exchange may improve. In this case, gas exchange refers to the removal of CO2 from the body and addition of O2 into the blood stream from inspired air. Thus, pO2 may increase and pCO2 may decrease, particularly in patients with COPD, but more generally in all patients treated with the device. Moreover, oxygen saturation may increase, reflecting an increase of oxygen binding to hemoglobin.

Other benefits offered by the respiratory device may include a reduction in diaphragm fatigue and improved efficiency of the accessory muscles of inspiration. This may make breathing significantly easier in patients with pulmonary disease, and more specifically COPD and cystic fibrosis.

As previously mentioned, the respiratory devices described herein may decrease respiratory rate. It has been shown that slowed breathing techniques can lead to a reduction in blood pressure. Thus, the device may reduce blood pressure in a patient, including patients with hypertension (systemic and pulmonary). The reduction in blood pressure may be systolic and/or diastolic. Reductions in blood pressure may be on the order of 1-70 mm Hg systolic or diastolic. This may bring the patient to normal (<140/80 mm Hg) or near normal (<160/100 mm Hg) levels. In patients who are being treated for hypertension, the device could be used as an adjunctive therapy to drugs or as a stand-alone therapy in some patients. In some versions, a respiratory device as described herein may be used for short periods (minutes, hours, or longer) over a span of days to weeks to months to offer longer term benefits for weeks or months after the cessation of therapy. Treatments may last 15 seconds to 24 hours and may be repeated over a regular or irregular interval, for example, on the order of hours to days. The devices may be worn at night or day, while awake or during sleep, to slow respiratory rate. A reduction in blood pressure and/or heart rate may be seen while the device is in place, or after the device has been removed. This may be due to hormonal influences whose effects last longer than the period in which the device is in place. More specifically, the device may work though either a sympathetic or parasympathetic pathway.

Expiratory resistance may also prolong expiratory time, which may reduce the respiratory rate. Thus, the devices described herein may be used to reduce respiratory rate. This may have benefits in treating insomnia, since it may promote a sense of relaxation in the user, through increased parasympathetic stimulation, decreased sympathetic simulation, and/other hormonal and non-hormonal effects. This may also promote a sense of wellbeing or relaxation that may allow the user to fall asleep easier and quicker and improve sleep quality and quantity. Thus, the respiratory devices described herein represent a novel non-pharmacologic method of treating insomnia and promoting relaxation. The device may be used throughout the day and/or night to promote said relaxation and wellbeing.

The respiratory devices described herein may also be used to treat or ameliorate disorders characterized by ineffective, non-productive, or otherwise disturbed inspiration (including but not limited to obstructive sleep apnea or restrictive pulmonary disease). For example, with the device in place, a patient may be more likely to have slightly elevated lung volumes after exhalation. Put another way, more air than normal may be present in the lungs after exhalation when using some versions of the device. Fewer alveoli may be collapsed; thus inhalation may be easier because it will require less effort to re-open the alveoli during the subsequent breath. Moreover, pulmonary congestion and pulmonary edema may also be reduced, so compliance may be improved. As a result, it may require less effort for patients to inhale. It follows that a smaller pressure differential (between the alveoli and the mouth) will be required. The smaller the pressure differential, the less likely that the patient's conducting airways (including the upper airways and pharyngeal tissues) will collapse, thus reducing the likelihood of obstructive sleep apnea, hypopnea, and snoring.

Infectious diseases may also benefit from the respiratory devices described herein. These diseases include but are not limited to pneumonia (community and hospital acquired), tuberculosis, bronchitis, HIV, and SARS.

The respiratory devices may also be useful in pulmonary or cardiac rehabilitation. For example, the device may find use in patients with chronic pulmonary disease including but not limited to chronic bronchitis, emphysema, asthma, pulmonary fibrosis, cystic fibrosis, and pulmonary hypertension. Alternatively, the devices may benefit patients with cardiac disease, including but not limited to: angina, myocardial infarction, right or left sided heart failure, cardiomyopathy, hypertension, valve disease, pulmonary embolus, and arrhythmia.

Patients with obesity may also benefit from the use of the respiratory devices described herein. Obesity can contribute to exercise intolerance partly because it increases the metabolic requirement during activity and alters ventilatory mechanics by reducing functional residual capacity (FRC) and promoting atelectasis. Obesity may also reduce cardiac reserve, since a higher than normal cardiac output response is required during physical activity. This in turn may cause systemic hypertension, which increases left ventricular afterload. Thus, the device, through its potential reduction in atelectasis and beneficial effects on FRC, cardiac output, and blood pressure may be useful in patients with obesity.

It has been suggested that expiratory positive airway pressure (as induced by the subject devices) may increase neural drive to the muscles that serve to maintain upper airway patency. Furthermore, FRC increases may improve length-tension relationships of the inspiratory muscles, allowing inspiratory pressures to decrease. This reduction of inspiratory pressure would thus make it less likely for the upper airway to obstruct, presumably due to a reduction in the transmural pressure gradient. As previously suggested, positive end expiratory pressure may improve ventilation-perfusion relationships which may improve oxygen saturation.

Furthermore, it is known that the upper airway partially or completely occludes during the expiratory phase of the breaths preceding an occlusive apnea. It is this narrowing of the upper airway at end-expiration that sets the stage for total occlusion during the next inspiration as subatmospheric pressures are generated within the airway. Expiratory positive airway pressure may therefore prevent airway narrowing during expiration, thus reducing the propensity toward total occlusion during inspiration. The phenomena of lung hysteresis may also provide therapeutic benefit.

The subject devices are also expected to improve sleep quality, duration and architecture. For example, there may be increased REM, slow wave, deep and/or stage 3 and 4 sleep and reduced light and/or stage 1 and 2 sleep. Sleep fragmentation may be improved with reduced transitions between sleep stages. There may be fewer arousals and/or awakenings. Subjects may experience REM or slow wave sleep rebound when the device is used. Subjects may have reduced central sleep apnea including central sleep apneas associated with sleep onset. Furthermore, subjects may experience more restful sleep and may awake more refreshed.

The respiratory devices may also be used by athletes, for example, during both aerobic and non-aerobic activities, partially because of the potentially beneficial direct effects on the heart and on gas exchange. In some versions, the respiratory device may be oversized, to increase the amount of inspiratory airflow, potentially increasing the amount of oxygen transmitted to the lungs for gas exchange.

The respiratory devices described herein may also be used for therapeutic and non-therapeutic effects on sleep. Sleep quality may be improved, with more slow-wave sleep, fewer arousals, and improved REM sleep. The user may have more productive sleep and may be less tired during the day. Furthermore, the beneficial effects of the device may extend beyond the period of use, and into the daytime as well, even when the device's use is limited to the night (e.g., when the user is sleeping). In some cases, sympathetic discharge may be reduced and/or parasympathetic discharge may be increased. Thus, the device may have positive benefits on the autonomic nervous system. This may offer beneficial systemic effects as well as local effects, some of which have already been described.

The respiratory devices described herein may also be used in other locations besides the nasal and oral cavities. Indeed, any location in the body that serves as an entry or exit location for respiratory airflow or serves as a conducting airway or conduit for airflow may benefit from the use of the devices described herein. For example, a device may be used within, on the external surface of, or near a stoma site (e.g., for use in a patient after a tracheostomy). Alternatively, devices may be adapted for use in ventilatory circuits within ventilators and other positive pressure breathing means (invasive and non-invasive) and in portable breathing devices such as Ambu-bags and the like.

Inflammation (which is present in a variety of disease states) may also be reduced using the respiratory device, possibly via the aforementioned parasympathetic or sympathetic mediated effects and/or effects of the vagus nerve and its stimulation. The treatment of any condition mediated by an inflammatory cytokine cascade is within the scope of the devices and methods described herein. In some embodiments, the respiratory device is used to treat a condition where the inflammatory cytokine cascade is affected through release of pro-inflammatory cytokines from a macrophage. The condition may be one where the inflammatory cytokine cascade causes a systemic reaction, such as with septic shock. Alternatively, the condition may be mediated by a localized inflammatory cytokine cascade, as in rheumatoid arthritis. Examples of conditions which may be usefully treated using the respiratory devices described herein include, but are not limited to: appendicitis, peptic, gastric or duodenal ulcers, peritonitis, pancreatitis, ulcerative, pseudomembranous, acute or ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Bane syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, diabetes, ankylosing spondylitis, Berger's disease, Retier's syndrome, or Hodgkins disease.

Furthermore, the respiratory devices and methods of using them may be used by or applied to a variety of different types of animals. Representative animals with which the methods and devices find use include, but are not limited to: canines; felines; equines; bovines; ovines; etc. and primates, particularly humans. The respiratory devices described herein may also be packaged for use. For example, the respiratory devices may be packaged individually or as a set (e.g., in sets of pairs, particularly in variations in which an individual device is used with each nostril). Furthermore, the packaging may be sterile, sterilizable, or clean.

The respiratory devices described herein may also be provided as part of a kit that includes at least one of the devices. Examples of kits may include a respiratory device and instructions for how to use the device. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. The instructions may take any form, including complete instructions on how to use the device, or references, directing a user to using additional sources for instructions (e.g., a website address with which instructions posted on the world wide web).

The device may be used in a clinical study, wherein said clinical study involves comparing sleep data from a patient with the device in place to sleep data from the same patient without the device in place. Any duration of the sleep study shall suffice, from minutes to hours.

The device may be used in patients who have already undergone ENT surgery to help their sleep apnea and/or snoring. This combination of surgery and use of the device may thus reduce AHI, snoring and other relevant parameters. Similarly, the use of weight reduction or sleep position therapy may find use in conjunction with this device.

As mentioned above, a respiratory device adapted for use in the nasal cavity may be placed into one or both of a subject's nostrils by medical personnel or by the subject himself. The respiratory device may be secured in place in the subject's nostrils by the interaction between the nostril cavity and the holdfast of the device. The device may be worn during the night or day, while the patient is awake or sleeping. In some cases, the device may be worn around the clock. For example, the device may be worn at night to prevent snoring.

Figure 71:
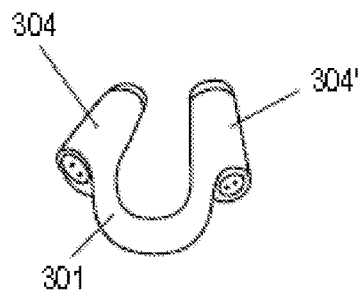
FIG. 71 shows another variation of whole-nose nasal devices.
Figure 72:
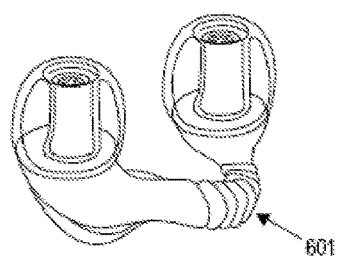
FIG. 72 shows another variation of a whole-nose nasal device.

FIGS. 71 and 72 illustrate example of whole-nose nasal devices as described above. FIG. 71 shows a whole-nose nasal device including a first holdfast region 304 and second holdfast region 304' that each include a rigid or adjustable rim forming a passage. Airflow resistors (e.g., a first airflow resistor and a second airflow resistor, not visible) are each positioned within each rim/holdfast. A bridging connector 301 connect the two. In the example shown in FIG. 72, the connector 601 connecting the two rims/holdfasts is adjustable.

Figures 73A, 73B, 73C, 73D:
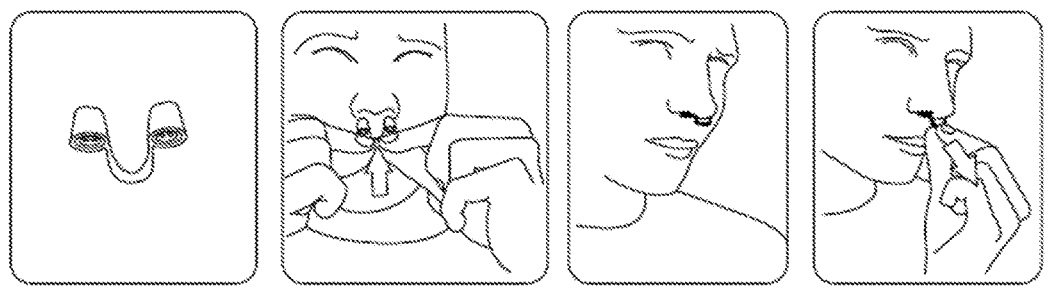
FIGS. 73A, 73B, 73C and 73D illustrate the application of one variation of a whole-nose nasal device.

FIGS. 73A-73D illustrate one method of inserting a whole-nose device such as the one shown in FIG. 71 into a subject's nose. FIG. 73A shows the whole-nose nasal device that may be adjusted by pushing or pulling on the connector, and/or by rotating the individual body regions forming the passageways (holding the airflow resistors). For example, the adjustable connector may include a bend region (e.g., a ductile wire surrounded by foam and/or polymer). In some variations, the adjustable connector includes a hinge joint near the center of the adjustable connector (in this figure, the hinge is surrounded by a foam or polymeric material, providing a protective layer that can protect the subject from pinching by the hinge); this hinge can be opened or closed to adjust the nasal device. After adjusting the whole-nose device, it may be initially inserted into the nose, as shown in FIG. 73B, and further adjusted so that it fits comfortably and snugly.

The whole-nose nasal device shown in FIGS. 73A-73D includes a rim/holdfast region surrounding each of the passageways that are placed in communication with each nostril. In this variation, the whole-nose nasal device is inserted into the subject's nose, and the holdfast (which may be, for example, a compressible foam) secures the device therein. This is shown in FIG. 73C. In some variations, the connector may also help hold the device in the subject's nose. For example, the adjustable connector may be adjusted so that the spacing between the passageways is slightly smaller than the spacing of the subject's nostrils, resulting in the device exerting a slight pressure on the septal region of the nose, helping to hold it is place (e.g., using an adjustable connector that is also flexible). In other variations, the holdfast region includes an adhesive holdfast that helps hold the device in position. The device may be further adjusted for comfort. After use, the device may be removed, as shown in FIG. 73D. In some variations, the adjustable connector may also help prevent the device from being inserted too far into the subject's nostril.

Other examples of whole-nose nasal devices as generally described herein are shown in U.S. patent application Ser. No. 11/941,915, filed Nov. 16, 2007 (now U.S. Pat. No. 8,240,309), herein incorporated by reference in its entirety.

All publications and patent applications cited in this specification are herein incorporated by reference in their entirety, as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A whole-nose nasal respiratory device configured to engage both of a subject's nostrils, the device comprising:
   a first holdfast comprising a first rim forming a first passageway;
   a first airflow resistor within the first passageway, the first airflow resistor comprising a first flap valve that inhibits exhalation through a first nostril more than inhalation through the first nostril when the first holdfast is worn in the first nostril;
   a second holdfast comprising a second rim forming a second passageway;
   a second airflow resistor within the second passageway, the second airflow resistor comprising a second flap valve that inhibits exhalation through a second nostril more than inhalation through the second nostril when the second holdfast is worn in the second nostril; and
   a connector connecting the first rim to the second rim.

2. The device of claim 1, further comprising one or more leak paths, the one or more leak paths allowing air to flow through the device even when air is restricted by the first and the second airflow resistors.

3. The device of claim 2, wherein the one or more leak paths comprise at least one aperture or channel through the first flap valve, the at least one aperture or channel being open even when the first flap valve is closed.

4. The device of claim 1, wherein the first holdfast is configured to form a seal between the respiratory device and the first nostril, and wherein the second holdfast is configured to form a seal between the respiratory device and the second nostril.

5. The device of claim 1, wherein the first and the second holdfast comprise a compliant material.

6. The device of claim 1, wherein the connector is a clip.

7. The device of claim 1, wherein the connector is one or more of: a clip, a tether, a strap, a band, a chain, and a string.

8. The device of claim 1, wherein the first rim and the second rim are oval.

9. The device of claim 1, wherein the first and second holdfast comprises silicone.

10. The device of claim 1, wherein the first and second rim comprises a compressible material.

11. The device of claim 1, wherein the first and second rim comprises a silicone rubber.

12. The device of claim 1, further comprising a filter within either the first or second passageway.

13. A whole-nose nasal respiratory device configured to engage both of a subject's nostrils, the device comprising:
    a first rim forming a first passageway, wherein the first rim is compressible;
    a first airflow resistor within the first passageway, the first airflow resistor comprising a first flap valve that inhibits exhalation through a first nostril more than inhalation through the first nostril;
    a second rim forming a second passageway, wherein the second rim is compressible;
    a second airflow resistor within the second passageway, the second airflow resistor comprising a second flap valve that inhibits exhalation through a second nostril more than inhalation through the second nostril;
    a connector comprising a clip connecting the first rim to the second rim.

14. The device of claim 13, further comprising one or more leak paths, the one or more leak paths allowing air to flow through the device even when air is restricted by the first and the second airflow resistors.

15. The device of claim 14, wherein the one or more leak paths comprise at least one aperture or channel through the first flap valve, the at least one aperture or channel being open even when the first flap valve is closed.

16. The device of claim 13, wherein the first and second rim are oval.

17. The device of claim 13, further comprising a therapeutic agent that is configured to come into contact with the subject's nostrils when the nasal respiratory device is worn.

18. The device of claim 13, wherein the first and second rim comprises a compressible material.

19. The device of claim 13, wherein the first and second rim comprises a silicone rubber.

20. A whole-nose nasal respiratory device configured to engage both of a subject's nostrils, the device comprising:
    a first rim forming a first passageway;
    a first airflow resistor within the first passageway, the first airflow resistor comprising a first flap valve that inhibits exhalation through a first nostril more than inhalation through the first nostril;
    a first holdfast on the first rim, the first holdfast configured to secure the first rim in communication with the first nostril when the device is worn;
    a second rim forming a second passageway;
    a second airflow resistor within the second passageway, the second airflow resistor comprising a second flap valve that inhibits exhalation through a second nostril more than inhalation through the second nostril;
    a second holdfast on the second rim, the second holdfast configured to secure the second rim in communication with the second nostril when the device is worn; and
    a connector connecting the first rim to the second rim.

* * * * *